(12) United States Patent
Karschnik et al.

(10) Patent No.: US 11,844,433 B2
(45) Date of Patent: Dec. 19, 2023

(54) BED WITH FOOT WARMING SYSTEM

(71) Applicant: Sleep Number Corporation, Minneapolis, MN (US)

(72) Inventors: Kody Lee Karschnik, Maple Grove, MN (US); Omid Sayadi, San Jose, CA (US); Wade Daniel Palashewski, Andover, MN (US); Ramazan Demirli, San Jose, CA (US); Eric Rose, Piedmont, SC (US); Saurabh Chhaparwal, Plymouth, MN (US)

(73) Assignee: Sleep Number Corporation, Minneapolis, MN (US)

( * ) Notice: Subject to any disclaimer, the term of this patent is extended or adjusted under 35 U.S.C. 154(b) by 60 days.

(21) Appl. No.: 17/091,094

(22) Filed: Nov. 6, 2020

(65) Prior Publication Data

US 2021/0289947 A1   Sep. 23, 2021

Related U.S. Application Data

(63) Continuation of application No. 15/337,034, filed on Oct. 28, 2016, now Pat. No. 10,827,846.

(51) Int. Cl.
*A47C 21/04* (2006.01)
*A61G 7/05* (2006.01)
*A47C 27/00* (2006.01)
*A47C 27/15* (2006.01)
*A47C 31/00* (2006.01)

(Continued)

(52) U.S. Cl.
CPC .......... *A47C 21/048* (2013.01); *A47C 27/002* (2013.01); *A47C 27/15* (2013.01); *A47C 31/001* (2013.01); *A47C 31/008* (2013.01);
*A61B 5/4809* (2013.01); *A61B 5/6892* (2013.01); *A61G 7/05* (2013.01); *A61M 21/02* (2013.01);
(Continued)

(58) Field of Classification Search
CPC ..... A47C 21/048; A47C 31/001; A47C 27/15; A61M 21/02; A61M 2021/0066; A61B 5/4809; A61G 2210/90
See application file for complete search history.

(56) References Cited

U.S. PATENT DOCUMENTS

| 1,486,412 A | 3/1924 | Biddlecom |
| 2,313,864 A | 3/1943 | Crise |

(Continued)

FOREIGN PATENT DOCUMENTS

WO   WO 2010/107724   9/2010

OTHER PUBLICATIONS

U.S. Appl. No. 14/819,630, Nunn et al., filed Aug. 6, 2015.
(Continued)

*Primary Examiner* — Eric J Kurilla
(74) *Attorney, Agent, or Firm* — Fish & Richardson P.C.

(57) ABSTRACT

A bed can include a mattress and a foot warming system. The mattress can include a mattress cover and a support structure that is positioned under and covered by the mattress cover. The foot warming system can include a heating unit an envelope, a power source, and an electrical connector electrically connecting the heating unit to the power source. The heating unit can be positioned inside the envelope between the envelope top and the envelope bottom. The heating unit and the envelope can be positioned at a foot of the bed under mattress cover between the support structure and the mattress cover.

21 Claims, 26 Drawing Sheets

(51) Int. Cl.
  *A61B 5/00* (2006.01)
  *A61M 21/02* (2006.01)
  *G16H 10/60* (2018.01)
  *A61M 21/00* (2006.01)

(52) U.S. Cl.
  CPC . *A61G 2210/90* (2013.01); *A61M 2021/0066* (2013.01); *G16H 10/60* (2018.01)

(56) References Cited

U.S. PATENT DOCUMENTS

| | | | |
|---|---|---|---|
| 2,708,234 A | 5/1955 | Kerr | |
| 2,850,617 A | 9/1958 | Coldren | |
| 3,423,574 A | 1/1969 | Shomphe et al. | |
| 4,044,221 A | 8/1977 | Kuhn | |
| 4,162,393 A * | 7/1979 | Balboni | H05B 3/36 |
| | | | 219/217 |
| 4,423,308 A | 12/1983 | Callaway et al. | |
| 4,766,628 A | 8/1988 | Greer et al. | |
| 4,788,729 A | 12/1988 | Greer et al. | |
| D300,194 S | 3/1989 | Walker | |
| 4,829,616 A | 5/1989 | Walker | |
| 4,890,344 A | 1/1990 | Walker | |
| 4,897,890 A | 2/1990 | Walker | |
| 4,908,895 A | 3/1990 | Walker | |
| D313,973 S | 1/1991 | Walker | |
| 4,991,244 A * | 2/1991 | Walker | A47C 27/082 |
| | | | 5/713 |
| 5,033,136 A * | 7/1991 | Elkins | A47C 21/048 |
| | | | 5/500 |
| 5,144,706 A | 9/1992 | Walker et al. | |
| 5,170,522 A | 12/1992 | Walker | |
| 5,433,223 A | 7/1995 | Moore-Ede et al. | |
| 5,484,983 A | 1/1996 | Roell | |
| D368,475 S | 4/1996 | Scott | |
| 5,509,154 A | 4/1996 | Shafer et al. | |
| 5,564,140 A | 10/1996 | Shoenhair et al. | |
| 5,642,546 A | 6/1997 | Shoenhair | |
| 5,652,484 A | 7/1997 | Shafer et al. | |
| 5,765,246 A | 6/1998 | Shoenhair | |
| 5,833,884 A | 11/1998 | Child | |
| 5,903,941 A | 5/1999 | Shafer et al. | |
| 5,904,172 A | 5/1999 | Gifft et al. | |
| 5,948,303 A | 9/1999 | Larson | |
| 6,037,723 A | 3/2000 | Shafer et al. | |
| 6,108,844 A | 8/2000 | Kraft et al. | |
| 6,145,143 A * | 11/2000 | Hicks | A61G 7/05784 |
| | | | 5/691 |
| 6,161,231 A | 12/2000 | Kraft et al. | |
| 6,163,907 A | 12/2000 | Larson | |
| 6,202,239 B1 | 3/2001 | Ward et al. | |
| 6,397,419 B1 | 6/2002 | Mechache | |
| 6,483,264 B1 | 11/2002 | Shafer et al. | |
| 6,527,715 B2 | 3/2003 | Balkin et al. | |
| 6,579,233 B2 | 6/2003 | Hursh | |
| 6,686,711 B2 | 2/2004 | Rose et al. | |
| 6,708,357 B2 | 3/2004 | Gaboury et al. | |
| 6,763,541 B2 | 7/2004 | Mahoney et al. | |
| 6,804,848 B1 | 10/2004 | Rose | |
| 6,832,397 B2 | 12/2004 | Gaboury | |
| D502,929 S | 3/2005 | Copeland et al. | |
| 6,883,191 B2 | 5/2005 | Gaboury et al. | |
| 7,120,951 B2 | 10/2006 | Augustine et al. | |
| 7,180,032 B2 | 2/2007 | Child et al. | |
| 7,207,938 B2 | 4/2007 | Hursh | |
| 7,389,554 B1 | 6/2008 | Rose | |
| 7,631,377 B1 * | 12/2009 | Sanford | A47C 21/044 |
| | | | 5/413 R |
| 7,701,332 B2 | 4/2010 | Anderson | |
| 7,827,637 B2 | 11/2010 | Defranks | |
| 7,865,988 B2 | 1/2011 | Koughan et al. | |
| 8,015,942 B2 | 9/2011 | Koskey, Jr. | |
| 8,179,270 B2 | 5/2012 | Rai et al. | |
| 8,282,452 B2 | 10/2012 | Grigsby et al. | |
| 8,336,369 B2 | 12/2012 | Mahoney | |
| 8,444,558 B2 | 5/2013 | Young et al. | |
| 8,484,153 B2 | 7/2013 | Mott et al. | |
| D691,118 S | 10/2013 | Ingham et al. | |
| 8,578,527 B2 | 11/2013 | Lachenbruch et al. | |
| D697,874 S | 1/2014 | Stusynski et al. | |
| D698,338 S | 1/2014 | Ingham | |
| D701,536 S | 3/2014 | Sakal | |
| 8,672,853 B2 | 3/2014 | Young | |
| 8,769,747 B2 | 7/2014 | Mahoney et al. | |
| 8,812,428 B2 | 8/2014 | Mallicone et al. | |
| 8,931,329 B2 | 1/2015 | Mahoney et al. | |
| 8,948,861 B2 | 2/2015 | Rai et al. | |
| 8,966,689 B2 | 3/2015 | McGuire et al. | |
| 8,973,183 B1 | 3/2015 | Palashewski et al. | |
| 8,984,687 B2 | 3/2015 | Stusynski et al. | |
| 9,066,601 B1 | 6/2015 | Aminy et al. | |
| D737,250 S | 8/2015 | Ingham et al. | |
| 10,245,177 B2 | 4/2019 | Harvis | |
| 2001/0020303 A1 * | 9/2001 | Endo | A61F 7/00 |
| | | | 5/421 |
| 2003/0218003 A1 | 11/2003 | Ellis et al. | |
| 2006/0053558 A1 * | 3/2006 | Ye | A47C 27/18 |
| | | | 5/689 |
| 2007/0257018 A1 * | 11/2007 | Huang | H05B 1/0272 |
| | | | 219/217 |
| 2007/0272673 A1 | 11/2007 | Keane | |
| 2008/0077020 A1 | 3/2008 | Young et al. | |
| 2010/0170043 A1 * | 7/2010 | Young | A61B 5/4806 |
| | | | 600/534 |
| 2010/0192299 A1 * | 8/2010 | Schermel | A47C 27/085 |
| | | | 5/717 |
| 2011/0034811 A1 | 2/2011 | Naujokat et al. | |
| 2011/0125330 A1 * | 5/2011 | Huber | A61G 7/05776 |
| | | | 700/12 |
| 2011/0144455 A1 | 6/2011 | Young et al. | |
| 2012/0210513 A1 | 8/2012 | Chestakov et al. | |
| 2012/0273475 A1 | 11/2012 | An | |
| 2012/0279953 A1 | 11/2012 | Augustine et al. | |
| 2013/0139315 A1 | 6/2013 | Pimenta | |
| 2014/0182061 A1 * | 7/2014 | Zaiss | A61G 7/05792 |
| | | | 5/423 |
| 2014/0250597 A1 | 9/2014 | Chen et al. | |
| 2014/0257571 A1 | 9/2014 | Chen et al. | |
| 2014/0259417 A1 | 9/2014 | Nunn et al. | |
| 2014/0259418 A1 | 9/2014 | Nunn et al. | |
| 2014/0259431 A1 | 9/2014 | Fleury | |
| 2014/0259433 A1 | 9/2014 | Nunn et al. | |
| 2014/0259434 A1 | 9/2014 | Nunn et al. | |
| 2014/0277611 A1 | 9/2014 | Nunn et al. | |
| 2014/0277778 A1 | 9/2014 | Nunn et al. | |
| 2014/0277822 A1 | 9/2014 | Nunn et al. | |
| 2014/0312027 A1 | 10/2014 | Augustine et al. | |
| 2015/0007393 A1 | 1/2015 | Palashewski | |
| 2015/0025327 A1 | 1/2015 | Young et al. | |
| 2015/0026896 A1 | 1/2015 | Fleury et al. | |
| 2015/0157137 A1 | 6/2015 | Nunn et al. | |
| 2015/0157519 A1 | 6/2015 | Stusynski et al. | |
| 2015/0182033 A1 | 7/2015 | Brosnan et al. | |
| 2015/0182397 A1 | 7/2015 | Palashewski et al. | |
| 2015/0182399 A1 | 7/2015 | Palashewski et al. | |
| 2015/0182418 A1 | 7/2015 | Zaiss | |
| 2015/0290059 A1 | 10/2015 | Brosnan et al. | |
| 2015/0366366 A1 | 12/2015 | Zaiss et al. | |
| 2015/0374137 A1 | 12/2015 | Mahoney et al. | |
| 2016/0066701 A1 | 3/2016 | Diller et al. | |
| 2016/0073788 A1 | 3/2016 | Franceschetti et al. | |
| 2016/0100696 A1 | 4/2016 | Palashewski et al. | |
| 2016/0165970 A1 | 6/2016 | Jost et al. | |
| 2019/0341147 A1 * | 11/2019 | Lord | A61B 5/4848 |

OTHER PUBLICATIONS

U.S. Appl. No. 14/885,751, Palashewski et al., filed Oct. 16, 2015.
U.S. Appl. No. 29/577,797, Karschnik et al., filed Sep. 15, 2016.
International Search Report and Written Opinion in International Application No. PCT/US2017/058055, dated Mar. 22, 2018, 20 pages.

(56) References Cited

OTHER PUBLICATIONS

International Preliminary Report in Application No. PCT/US2017/058055, dated Apr. 30, 2019, 11 pages.

\* cited by examiner

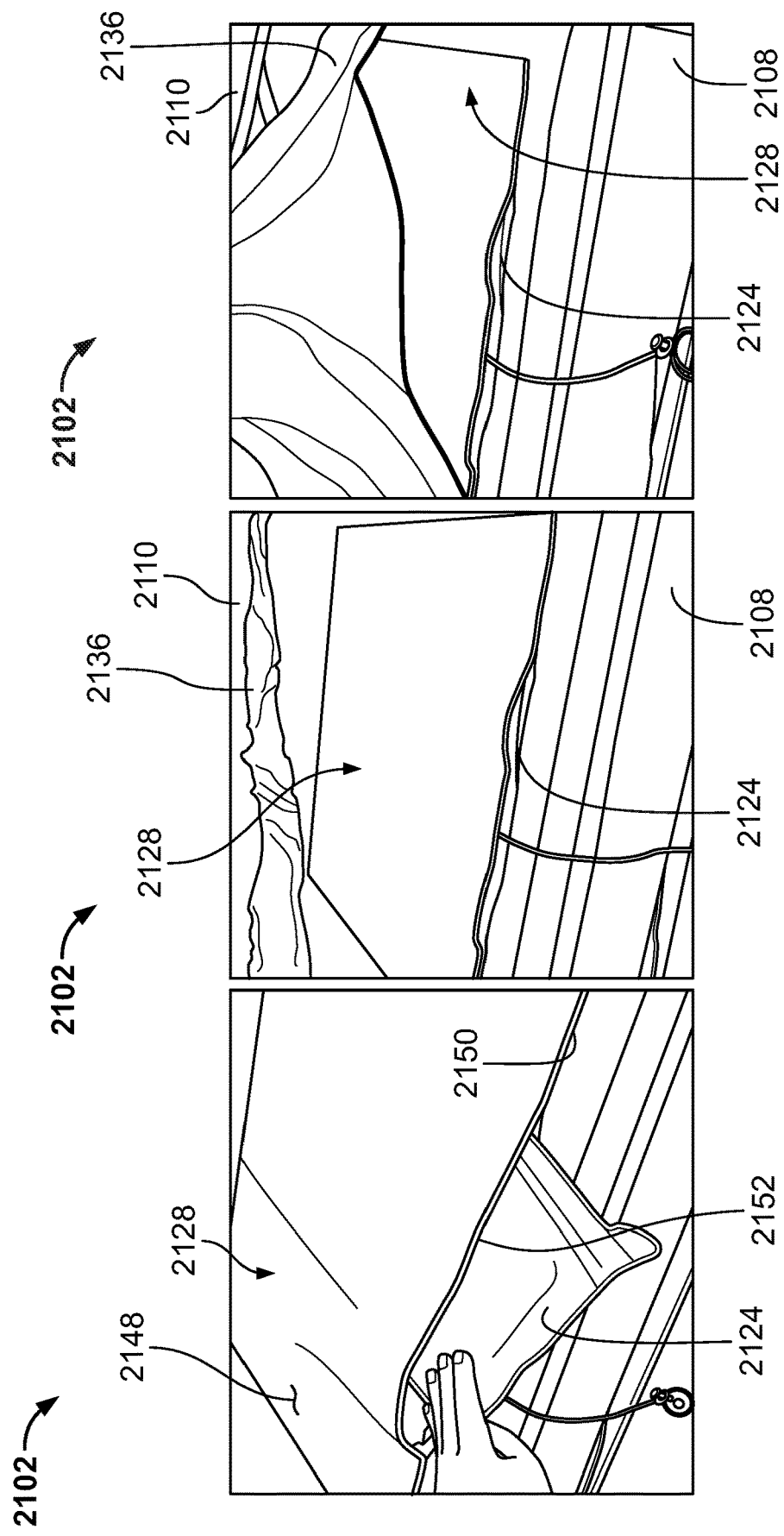

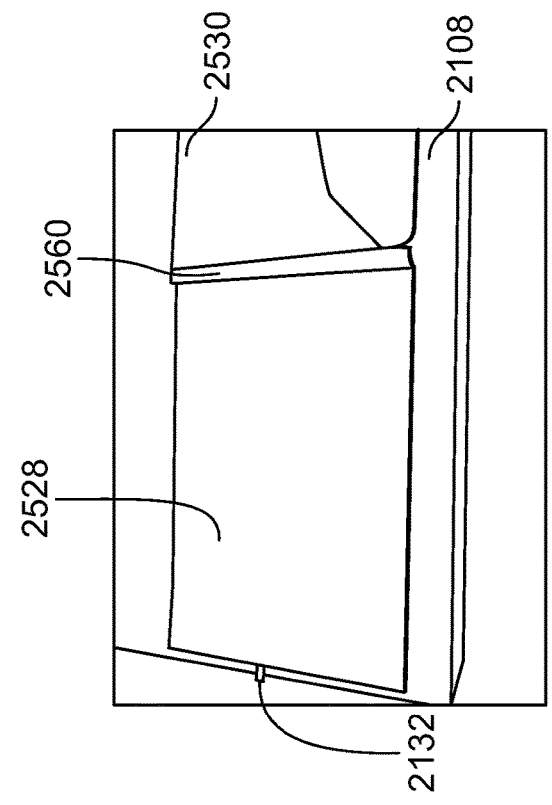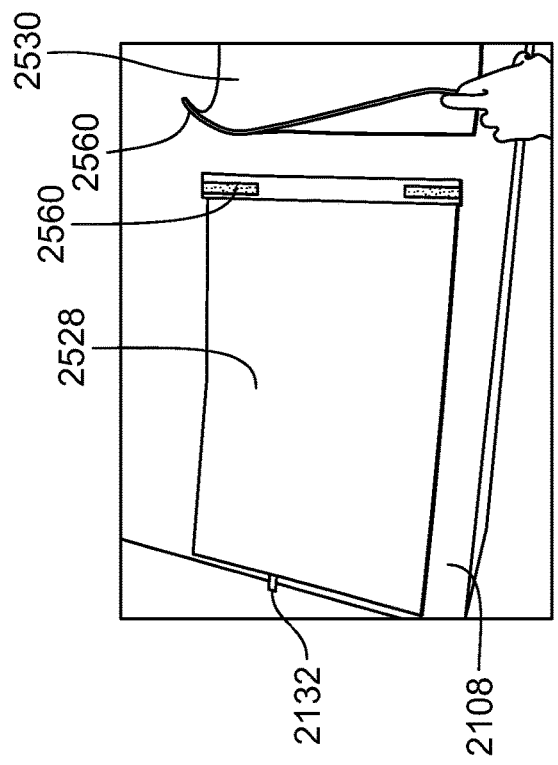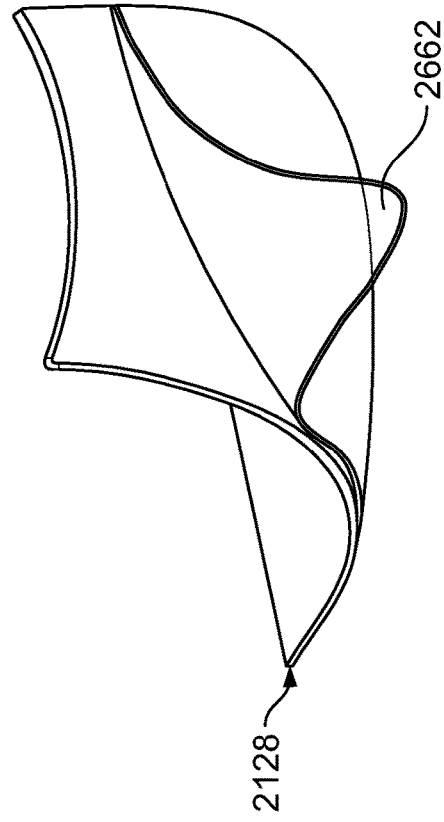

BED WITH FOOT WARMING SYSTEM

CROSS-REFERENCE TO RELATED APPLICATIONS

This application claims the benefit of U.S. application Ser. No. 15/337,034, filed Oct. 28, 2016. The disclosure of the prior application is considered part of (and is incorporated by reference in) the disclosure of this application.

The present invention relates to beds, and more particularly to bed warming.

BACKGROUND

In general, a bed is a piece of furniture used as a location to sleep or relax. Many modern beds include a soft mattress on a bed frame. The mattress may include springs, foam material, and/or an air chamber to support the weight of one or more occupants. In some cases, users can have relatively poor sleep quality using beds that appear comfortable and otherwise suitable.

SUMMARY

Some embodiments of a mattress and related assemblies can include one or more of the features and functions disclosed herein. Some embodiments can include a warming system positioned in the mattress at a foot of a mattress. The warming system can include a heating unit such as an electrically conductive fabric that is relatively thin and flexible for warming the foot of the mattress. The warming system can be configured to warm the feet of the user so as to induce rapid onset of sleep. The warming system can be automatically controlled to achieve desired comfort and sleep quality. Various embodiments can be configured with particular functions and features.

In one aspect, A bed can include a mattress and a foot warming system. The mattress can include a mattress cover and a support structure that is positioned under and covered by the mattress cover. The foot warming system can include a heating unit, a power source, and an electrical connector electrically connecting the heating unit to the power source. The heating unit can be positioned inside the envelope between the envelope top and the envelope bottom. The heating unit and the envelope can be positioned at a foot of the bed under mattress cover between the support structure and the mattress cover.

Implementations can include any, all, or none of the following features. The support structure can include at least one foam layer. The envelope bottom is attached to the foam layer. The envelope includes a fire resistant material. The bed further includes a fire resistant cap covering the support structure, the envelope, and the heating unit. The envelope top includes a breathable mesh and the envelope bottom comprises a fire resistant material. The heating unit includes a flexible layer of electrically conductive fabric, such as carbon encased in a flexible polymer material. The power source includes a controller configured to selectively power the heating unit to generate heat.

Implementations can also include any, all, or none of the following features. The controller is configured to access historical sleep metrics that represent a sleep quality of a user while the user was sleeping in the bed, access historical sensor data that represent sensor readings that measure environmental conditions affecting the user while the user was sleeping in the bed, identify, in the historical sleep metrics, incidences of low quality sleep experienced by the user, generate a corrective plan that specifies a change to the foot warming system to improve sleep quality, and drive the foot warming system according to the generated corrective plan. The controller is configured to determine an expected bed time for a user of the bed and drive the foot warming system to heat the foot of the bed via the heating unit to reach a target temperature prior to the expected bed time. The controller drives the foot warming system via pulse wave modulation to maintain temperature at the target temperature once the target temperature has been reached. The bed further includes a sensor configured to detect the user entering the bed, wherein the sensor is in communication with the controller and wherein the controller is further configured to reduce power to the heating unit upon the sensor detecting the user entering the bed. The controller stops powering the heating unit as soon as the user is detected entering the bed. The controller reduces power to the heating unit at a predetermined amount of time after the user is detected entering the bed. The foot warming system includes a temperature sensor in communication with the controller and the controller is configured to drive the heating unit as a function of a difference between sensed temperature and target temperature such that the controller supplies more power to the heating unit in response to determining a relatively large difference between the sensed temperature and target temperature and the controller supplies less power to the heating unit in response to determining a relatively small difference between the sensed temperature and target temperature. The controller is configured to determine whether the user is asleep as a function of sensed data and drive the foot warming system as a function of whether the user is determined to be asleep. The controller is further configured to monitor a sleeping routine of the user over multiple days via one or more sensors to determine a learned sleep schedule and drive the foot warming system to heat the foot of the bed via the heating unit as a function of the learned sleep schedule. The support structure of the mattress comprises a first air chamber sized for supporting a first user, a second air chamber sized for supporting a second user, and a foam layer positioned above the first and second chambers, wherein the heating unit comprises a first heating unit connected to the foam layer above the first air chamber and a second heating unit connected to the foam layer above the second air chamber. The first heating unit is attached to the foam layer via the envelope having a first envelope opening and the second heating unit is attached to the foam layer via a second envelope having a second envelope opening, wherein the first and second heating units are removable through the first and second envelope openings, respectively. The heating unit is a relatively thin layer with a width of between 21 inches and 31 inches and a depth of between 10 inches and 20 inches. The heating unit includes a first tinned copper bus bar, a second tinned copper bus bar extending substantially parallel to the first tinned copper bus bar, multiple strips of carbon-based electrically conductive material extending from the first to the second tinned copper bus bar, a temperature sensor, and a plurality of wires electrically connecting the power source to each of the first tinned copper bus bar, the second tinned copper bus bar, and the temperature sensor.

In another aspect, a bed including a mattress and a foot warming system. The mattress includes a mattress cover and a support structure that is positioned under and covered by the mattress cover. The foot warming system includes a heating unit positioned under the mattress cover and comprising a plurality of flexible flat heating elements spaced with gaps between each of the flexible flat heating elements, a power source, and an electrical connector electrically connecting the heating units to the power source.

Implementations can also include any, all, or none of the following features. The support structure includes an air chamber and a foam that defines a pathway through which the electrical connector extends between the heating unit and the power source. The heating unit includes a first tinned copper bus bar, a second tinned copper bus bar extending substantially parallel to the first tinned copper bus bar, a temperature sensor, and a plurality of wires electrically connecting the power source to each of the first tinned copper bus bar, the second tinned copper bus bar, and the temperature sensor, and wherein the flexible flat heating elements are connected in parallel between the first and second tinned copper bus bars.

Other features, aspects and potential advantages will be apparent from the accompanying description and figures.

DESCRIPTION OF DRAWINGS

FIGS. 24A-24C are top perspective views of a foot warming system for use in the beds of FIGS. 21-23.

FIGS. 25A and 25B are top perspective views of envelopes of a foot warming system being attached.

FIG. 26 is a perspective view of a bottom of an envelope of a foot warming system.

Like reference symbols in the various drawings indicate like elements.

DETAILED DESCRIPTION

A bed having a foot warming system can improve sleep quality by warming a user's feet to induce rapid onset of sleep for the user and extend sleep duration. Such a system can include an heating unit placed at a foot of a mattress and within the mattress so as to suitable warm a user's feet without being intrusive for the rest of the sleeping experience. Such a system can be configured such that a user hardly feels or otherwise notices the foot warming system positioned in the mattress except for the warming effect that it generates. Such a system can be driven automatically to improve sleep quality, alone or in conjunction with other features described herein.

Example Airbed Hardware

Figure 1:
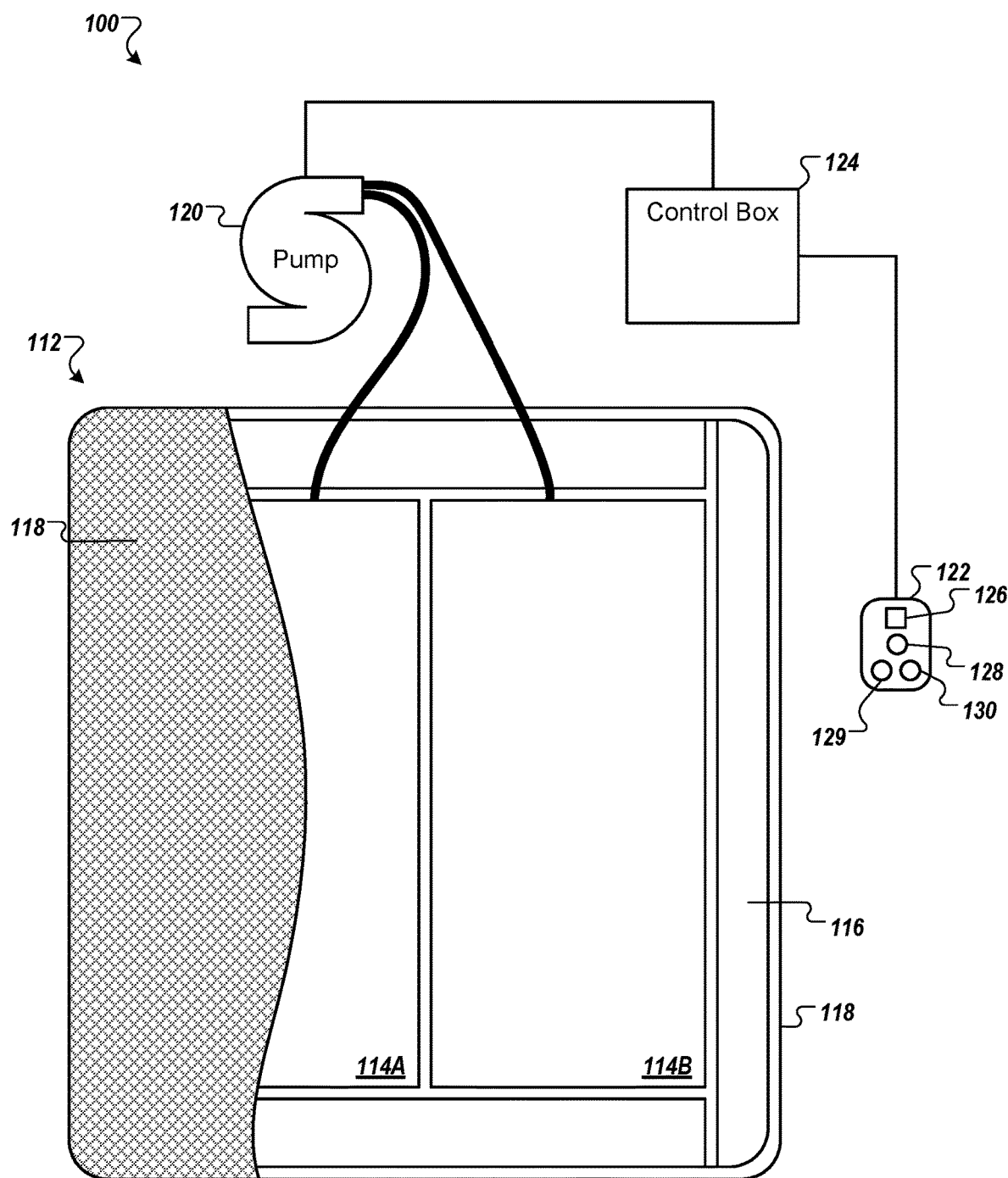
FIG. 1 shows an example air bed system.

FIG. 1 shows an example air bed system 100 that includes a bed 112. The bed 112 includes at least one air chamber 114 surrounded by a resilient border 116 and encapsulated by bed ticking 118. The resilient border 116 can comprise any suitable material, such as foam.

As illustrated in FIG. 1, the bed 112 can be a two chamber design having first and second fluid chambers, such as a first air chamber 114A and a second air chamber 114B. In alternative embodiments, the bed 112 can include chambers for use with fluids other than air that are suitable for the application. In some embodiments, such as single beds or kids' beds, the bed 112 can include a single air chamber 114A or 114B or multiple air chambers 114A and 114B. First and second air chambers 114A and 114B can be in fluid communication with a pump 120. The pump 120 can be in electrical communication with a remote control 122 via control box 124. The control box 124 can include a wired or wireless communications interface for communicating with one or more devices, including the remote control 122. The control box 124 can be configured to operate the pump 120 to cause increases and decreases in the fluid pressure of the first and second air chambers 114A and 114B based upon commands input by a user using the remote control 122. In some implementations, the control box 124 is integrated into a housing of the pump 120.

The remote control 122 can include a display 126, an output selecting mechanism 128, a pressure increase button 129, and a pressure decrease button 130. The output selecting mechanism 128 can allow the user to switch air flow generated by the pump 120 between the first and second air chambers 114A and 114B, thus enabling control of multiple air chambers with a single remote control 122 and a single pump 120. For example, the output selecting mechanism 128 can by a physical control (e.g., switch or button) or an input control displayed on display 126. Alternatively, separate remote control units can be provided for each air chamber and can each include the ability to control multiple air chambers. Pressure increase and decrease buttons 129 and 130 can allow a user to increase or decrease the pressure, respectively, in the air chamber selected with the output selecting mechanism 128. Adjusting the pressure within the selected air chamber can cause a corresponding adjustment to the firmness of the respective air chamber. In some embodiments, the remote control 122 can be omitted or modified as appropriate for an application. For example, in some embodiments the bed 112 can be controlled by a computer, tablet, smart phone, or other device in wired or wireless communication with the bed 112.

Figure 2:
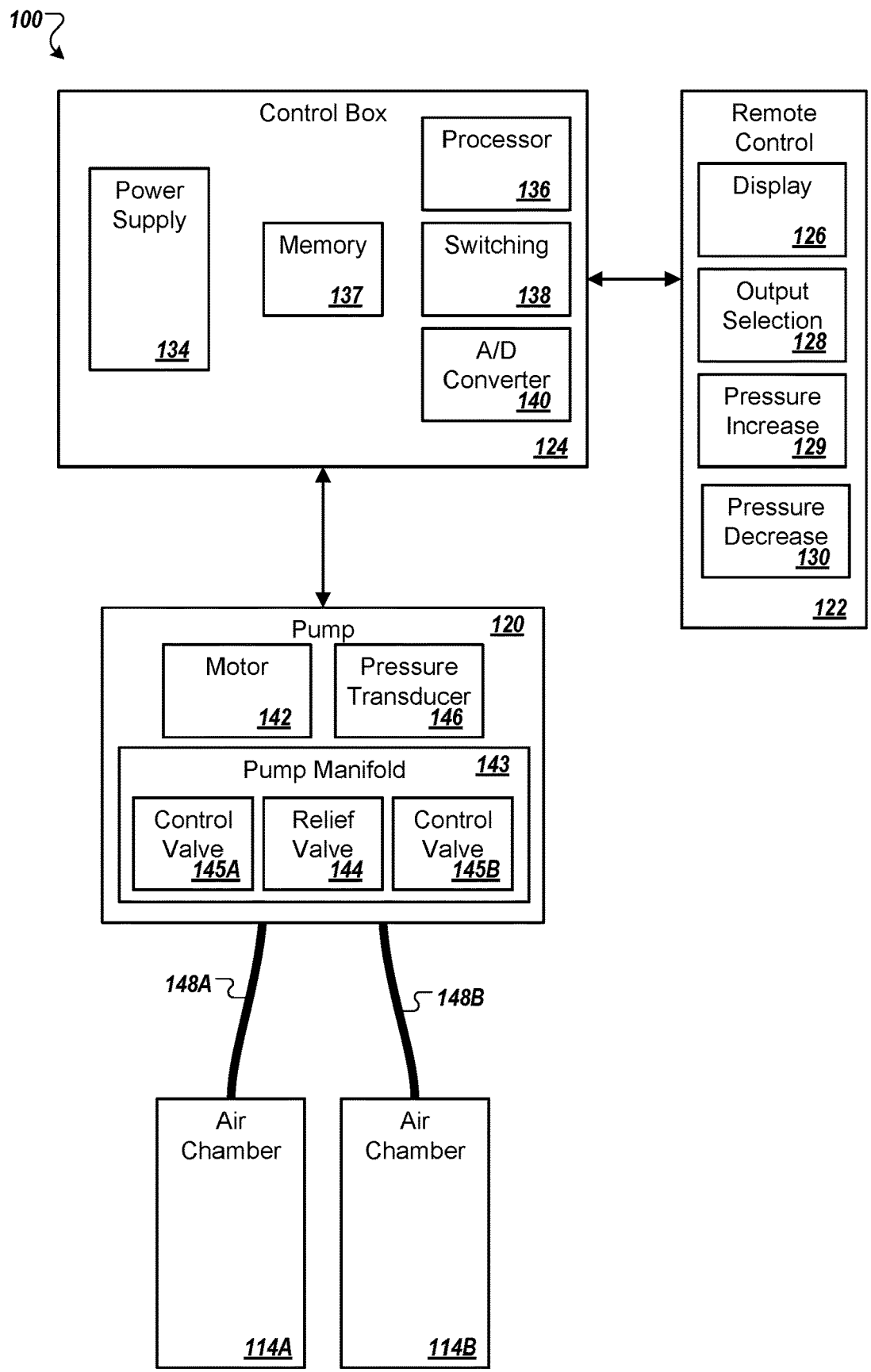
FIG. 2 is a block diagram of an example of various components of an air bed system.

FIG. 2 is a block diagram of an example of various components of an air bed system. For example, these components can be used in the example air bed system 100. As shown in FIG. 2, the control box 124 can include a power supply 134, a processor 136, a memory 137, a switching mechanism 138, and an analog to digital (A/D) converter 140. The switching mechanism 138 can be, for example, a relay or a solid state switch. In some implementations, the switching mechanism 138 can be located in the pump 120 rather than the control box 124.

The pump 120 and the remote control 122 are in two-way communication with the control box 124. The pump 120 includes a motor 142, a pump manifold 143, a relief valve 144, a first control valve 145A, a second control valve 145B, and a pressure transducer 146. The pump 120 is fluidly connected with the first air chamber 114A and the second air chamber 114B via a first tube 148A and a second tube 148B, respectively. The first and second control valves 145A and 145B can be controlled by switching mechanism 138, and are operable to regulate the flow of fluid between the pump 120 and first and second air chambers 114A and 114B, respectively.

In some implementations, the pump 120 and the control box 124 can be provided and packaged as a single unit. In some alternative implementations, the pump 120 and the control box 124 can be provided as physically separate units. In some implementations, the control box 124, the pump 120, or both are integrated within or otherwise contained within a bed frame or bed support structure that supports the bed 112. In some implementations, the control box 124, the pump 120, or both are located outside of a bed frame or bed support structure (as shown in the example in FIG. 1).

The example air bed system 100 depicted in FIG. 2 includes the two air chambers 114A and 114B and the single pump 120. However, other implementations can include an air bed system having two or more air chambers and one or more pumps incorporated into the air bed system to control the air chambers. For example, a separate pump can be associated with each air chamber of the air bed system or a pump can be associated with multiple chambers of the air bed system. Separate pumps can allow each air chamber to be inflated or deflated independently and simultaneously. Furthermore, additional pressure transducers can also be incorporated into the air bed system such that, for example, a separate pressure transducer can be associated with each air chamber.

In use, the processor 136 can, for example, send a decrease pressure command to one of air chambers 114A or 114B, and the switching mechanism 138 can be used to convert the low voltage command signals sent by the processor 136 to higher operating voltages sufficient to operate the relief valve 144 of the pump 120 and open the control valve 145A or 145B. Opening the relief valve 144 can allow air to escape from the air chamber 114A or 114B through the respective air tube 148A or 148B. During deflation, the pressure transducer 146 can send pressure readings to the processor 136 via the A/D converter 140. The A/D converter 140 can receive analog information from pressure transducer 146 and can convert the analog information to digital information useable by the processor 136. The processor 136 can send the digital signal to the remote control 122 to update the display 126 in order to convey the pressure information to the user.

As another example, the processor 136 can send an increase pressure command. The pump motor 142 can be energized in response to the increase pressure command and send air to the designated one of the air chambers 114A or 114B through the air tube 148A or 148B via electronically operating the corresponding valve 145A or 145B. While air is being delivered to the designated air chamber 114A or 114B in order to increase the firmness of the chamber, the pressure transducer 146 can sense pressure within the pump manifold 143. Again, the pressure transducer 146 can send pressure readings to the processor 136 via the A/D converter 140. The processor 136 can use the information received from the A/D converter 140 to determine the difference between the actual pressure in air chamber 114A or 114B and the desired pressure. The processor 136 can send the digital signal to the remote control 122 to update display 126 in order to convey the pressure information to the user.

Generally speaking, during an inflation or deflation process, the pressure sensed within the pump manifold 143 can provide an approximation of the pressure within the respective air chamber that is in fluid communication with the pump manifold 143. An example method of obtaining a pump manifold pressure reading that is substantially equivalent to the actual pressure within an air chamber includes turning off pump 120, allowing the pressure within the air chamber 114A or 114B and the pump manifold 143 to equalize, and then sensing the pressure within the pump manifold 143 with the pressure transducer 146. Thus, providing a sufficient amount of time to allow the pressures within the pump manifold 143 and chamber 114A or 114B to equalize can result in pressure readings that are accurate approximations of the actual pressure within air chamber 114A or 114B. In some implementations, the pressure of the air chambers 114A and/or 114B can be continuously monitored using multiple pressure sensors (not shown).

In some implementations, information collected by the pressure transducer 146 can be analyzed to determine various states of a person lying on the bed 112. For example, the processor 136 can use information collected by the pressure transducer 146 to determine a heart rate or a respiration rate for a person lying in the bed 112. For example, a user can be lying on a side of the bed 112 that includes the chamber 114A. The pressure transducer 146 can monitor fluctuations in pressure of the chamber 114A and this information can be used to determine the user's heart rate and/or respiration rate. As another example, additional processing can be performed using the collected data to determine a sleep state of the person (e.g., awake, light sleep, deep sleep). For example, the processor 136 can determine when a person falls asleep and, while asleep, the various sleep states of the person.

Additional information associated with a user of the air bed system 100 that can be determined using information collected by the pressure transducer 146 includes motion of the user, presence of the user on a surface of the bed 112, weight of the user, heart arrhythmia of the user, and apnea. Taking user presence detection for example, the pressure transducer 146 can be used to detect the user's presence on the bed 112, e.g., via a gross pressure change determination and/or via one or more of a respiration rate signal, heart rate signal, and/or other biometric signals. For example, a simple pressure detection process can identify an increase in pressure as an indication that the user is present on the bed 112. As another example, the processor 136 can determine that the user is present on the bed 112 if the detected pressure increases above a specified threshold (so as to indicate that a person or other object above a certain weight is positioned on the bed 112). As yet another example, the processor 136 can identify an increase in pressure in combination with detected slight, rhythmic fluctuations in pressure as corresponding to the user being present on the bed 112. The presence of rhythmic fluctuations can be identified as being caused by respiration or heart rhythm (or both) of the user. The detection of respiration or a heartbeat can distinguish between the user being present on the bed and another object (e.g., a suit case) being placed upon the bed.

In some implementations, fluctuations in pressure can be measured at the pump 120. For example, one or more pressure sensors can be located within one or more internal cavities of the pump 120 to detect fluctuations in pressure within the pump 120. The fluctuations in pressure detected at the pump 120 can indicate fluctuations in pressure in one or both of the chambers 114A and 114B. One or more sensors located at the pump 120 can be in fluid communication with the one or both of the chambers 114A and 114B, and the sensors can be operative to determine pressure within the chambers 114A and 114B. The control box 124 can be configured to determine at least one vital sign (e.g., heart rate, respiratory rate) based on the pressure within the chamber 114A or the chamber 114B.

In some implementations, the control box 124 can analyze a pressure signal detected by one or more pressure sensors to determine a heart rate, respiration rate, and/or other vital signs of a user lying or sitting on the chamber 114A or the chamber 114B. More specifically, when a user lies on the bed 112 positioned over the chamber 114A, each of the user's heart beats, breaths, and other movements can create a force on the bed 112 that is transmitted to the chamber 114A. As a result of the force input to the chamber 114A from the user's movement, a wave can propagate through the chamber 114A and into the pump 120. A pressure sensor located at the pump 120 can detect the wave, and thus the pressure signal output by the sensor can indicate a heart rate, respiratory rate, or other information regarding the user.

With regard to sleep state, air bed system 100 can determine a user's sleep state by using various biometric signals such as heart rate, respiration, and/or movement of the user. While the user is sleeping, the processor 136 can receive one or more of the user's biometric signals (e.g., heart rate, respiration, and motion) and determine the user's present sleep state based on the received biometric signals. In some implementations, signals indicating fluctuations in pressure in one or both of the chambers 114A and 114B can be amplified and/or filtered to allow for more precise detection of heart rate and respiratory rate.

The control box 124 can perform a pattern recognition algorithm or other calculation based on the amplified and filtered pressure signal to determine the user's heart rate and respiratory rate. For example, the algorithm or calculation can be based on assumptions that a heart rate portion of the signal has a frequency in the range of 0.5-4.0 Hz and that a respiration rate portion of the signal a has a frequency in the range of less than 1 Hz. The control box 124 can also be configured to determine other characteristics of a user based on the received pressure signal, such as blood pressure, tossing and turning movements, rolling movements, limb movements, weight, the presence or lack of presence of a user, and/or the identity of the user. Techniques for monitoring a user's sleep using heart rate information, respiration rate information, and other user information are disclosed in U.S. Patent Application Publication No. 20100170043 to Steven J. Young et al., titled "APPARATUS FOR MONITORING VITAL SIGNS," the entire contents of which is incorporated herein by reference.

For example, the pressure transducer 146 can be used to monitor the air pressure in the chambers 114A and 114B of the bed 112. If the user on the bed 112 is not moving, the air pressure changes in the air chamber 114A or 114B can be relatively minimal, and can be attributable to respiration and/or heartbeat. When the user on the bed 112 is moving, however, the air pressure in the mattress can fluctuate by a much larger amount. Thus, the pressure signals generated by the pressure transducer 146 and received by the processor 136 can be filtered and indicated as corresponding to motion, heartbeat, or respiration.

In some implementations, rather than performing the data analysis in the control box 124 with the processor 136, a digital signal processor (DSP) can be provided to analyze the data collected by the pressure transducer 146. Alternatively, the data collected by the pressure transducer 146 could be sent to a cloud-based computing system for remote analysis.

In some implementations, the example air bed system 100 further includes a temperature controller configured to increase, decrease, or maintain the temperature of a bed, for example for the comfort of the user. For example, a pad can be placed on top of or be part of the bed 112, or can be placed on top of or be part of one or both of the chambers 114A and 114B. Air can be pushed through the pad and vented to cool off a user of the bed. Conversely, the pad can include a heating element that can be used to keep the user warm. In some implementations, the temperature controller can receive temperature readings from the pad. In some implementations, separate pads are used for the different sides of the bed 112 (e.g., corresponding to the locations of the chambers 114A and 114B) to provide for differing temperature control for the different sides of the bed.

In some implementations, the user of the air bed system 100 can use an input device, such as the remote control 122, to input a desired temperature for the surface of the bed 112 (or for a portion of the surface of the bed 112). The desired temperature can be encapsulated in a command data structure that includes the desired temperature as well as identifies the temperature controller as the desired component to be controlled. The command data structure can then be transmitted via Bluetooth or another suitable communication protocol to the processor 136. In various examples, the command data structure is encrypted before being transmitted. The temperature controller can then configure its elements to increase or decrease the temperature of the pad depending on the temperature input into remote control 122 by the user.

In some implementations, data can be transmitted from a component back to the processor 136 or to one or more display devices, such as the display 126. For example, the current temperature as determined by a sensor element of temperature controller, the pressure of the bed, the current position of the foundation or other information can be transmitted to control box 124. The control box 124 can then transmit the received information to remote control 122 where it can be displayed to the user (e.g., on the display 126).

In some implementations, the example air bed system 100 further includes an adjustable foundation and an articulation controller configured to adjust the position of a bed (e.g., the bed 112) by adjusting the adjustable foundation that supports the bed. For example, the articulation controller can adjust the bed 112 from a flat position to a position in which a head portion of a mattress of the bed is inclined upward (e.g., to facilitate a user sitting up in bed and/or watching television). In some implementations, the bed 112 includes multiple separately articulable sections. For example, portions of the bed corresponding to the locations of the chambers 114A and 114B can be articulated independently from each other, to allow one person positioned on the bed 112 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 112 can include more than one zone that can be independently adjusted. The articulation controller can also be configured to provide different levels of massage to one or more users on the bed 112.

Example of a Bed in a Bedroom Environment

Figure 3:
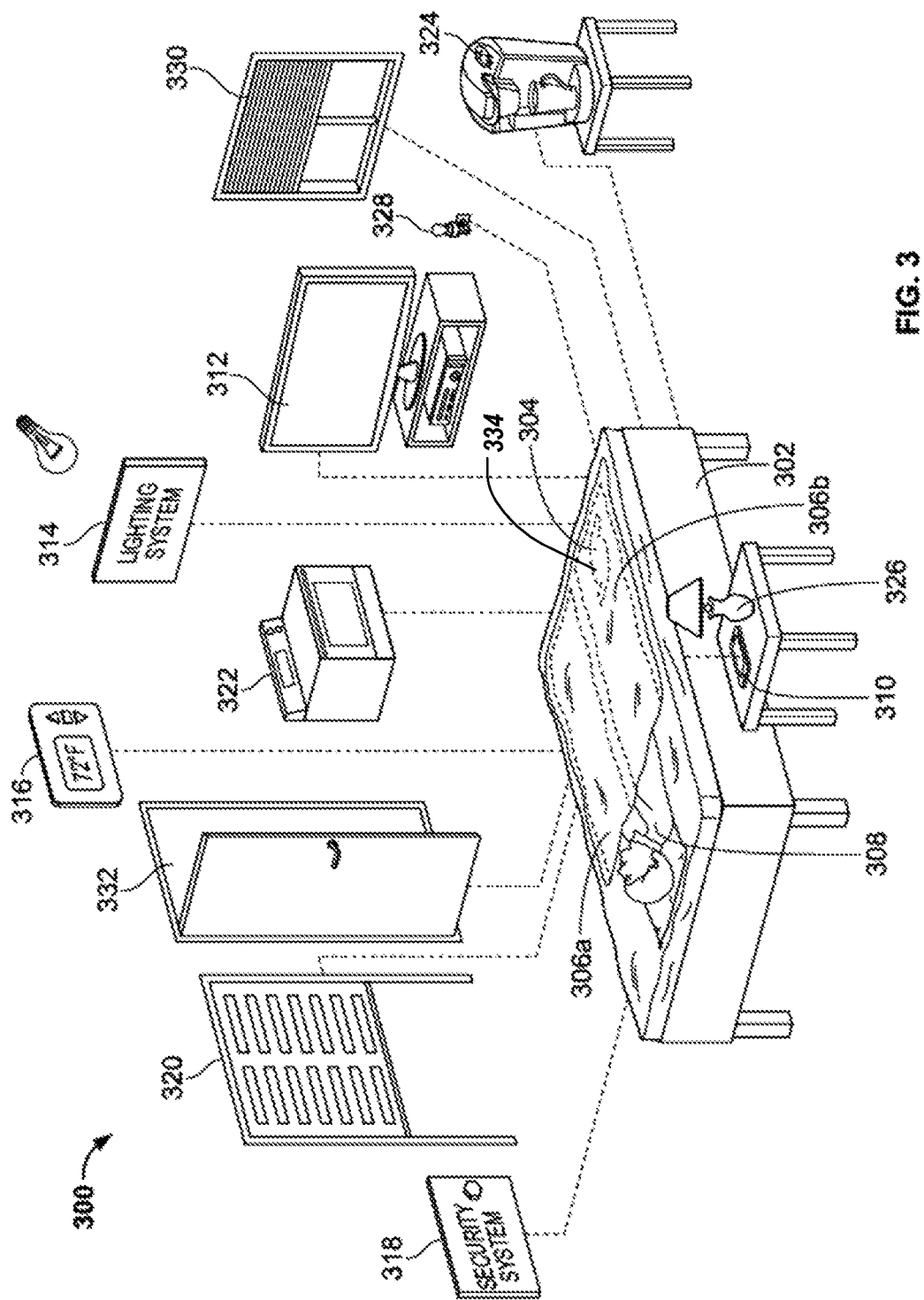
FIG. 3 shows an example environment including a bed in communication with devices located in and around a home.

FIG. 3 shows an example environment 300 including a bed 302 in communication with devices located in and around a home. In the example shown, the bed 302 includes pump 304 for controlling air pressure within two air chambers 306a and 306b (as described above with respect to the air chambers 114A-114B). The pump 304 additionally includes circuitry for controlling inflation and deflation functionality performed by the pump 304. The circuitry is further programmed to detect fluctuations in air pressure of the air chambers 306a-b and used the detected fluctuations in air pressure to identify bed presence of a user 308, sleep state of the user 308, movement of the user 308, and biometric signals of the user 308 such as heart rate and respiration rate. In the example shown, the pump 304 is located within a support structure of the bed 302 and the control circuitry 334 for controlling the pump 304 is integrated with the pump 304. In some implementations, the control circuitry 334 is physically separate from the pump 304 and is in wireless or wired communication with the pump 304. In some implementations, the pump 304 and/or control circuitry 334 are located outside of the bed 302. In some implementations, various control functions can be performed by systems located in different physical locations. For example, circuitry for controlling actions of the pump 304 can be located within a pump casing of the pump 304 while control circuitry 334 for performing other functions associated with the bed 302 can be located in another portion of the bed 302, or external to the bed 302. As another example, control circuitry 334 located within the pump 304 can communicate with control circuitry 334 at a remote location through a LAN or WAN (e.g., the internet). As yet another example, the control circuitry 334 can be included in the control box 124 of FIGS. 1 and 2.

In some implementations, one or more devices other than, or in addition to, the pump 304 and control circuitry 334 can be utilized to identify user bed presence, sleep state, movement, and biometric signals. For example, the bed 302 can include a second pump in addition to the pump 304, with each of the two pumps connected to a respective one of the air chambers 306a-b. For example, the pump 304 can be in fluid communication with the air chamber 306b to control inflation and deflation of the air chamber 306b as well as detect user signals for a user located over the air chamber 306b such as bed presence, sleep state, movement, and biometric signals while the second pump is in fluid communication with the air chamber 306a to control inflation and deflation of the air chamber 306a as well as detect user signals for a user located over the air chamber 306a.

As another example, the bed 302 can include one or more pressure sensitive pads or surface portions that are operable to detect movement, including user presence, user motion, respiration, and heart rate. For example, a first pressure sensitive pad can be incorporated into a surface of the bed 302 over a left portion of the bed 302, where a first user would normally be located during sleep, and a second pressure sensitive pad can be incorporated into the surface of the bed 302 over a right portion of the bed 302, where a second user would normally be located during sleep. The movement detected by the one or more pressure sensitive pads or surface portions can be used by control circuitry 334 to identify user sleep state, bed presence, or biometric signals.

In some implementations, information detected by the bed (e.g., motion information) is processed by control circuitry 334 (e.g., control circuitry 334 integrated with the pump 304) and provided to one or more user devices such as a user device 310 for presentation to the user 308 or to other users. In the example depicted in FIG. 3, the user device 310 is a tablet device; however, in some implementations, the user device 310 can be a personal computer, a smart phone, a smart television (e.g., a television 312), or other user device capable of wired or wireless communication with the control circuitry 334. The user device 310 can be in communication with control circuitry 334 of the bed 302 through a network or through direct point-to-point communication. For example, the control circuitry 334 can be connected to a LAN (e.g., through a Wi-Fi router) and communicate with the user device 310 through the LAN. As another example, the control circuitry 334 and the user device 310 can both connect to the Internet and communicate through the Internet. For example, the control circuitry 334 can connect to the Internet through a WiFi router and the user device 310 can connect to the Internet through communication with a cellular communication system. As another example, the control circuitry 334 can communicate directly with the user device 310 through a wireless communication protocol such as Bluetooth. As yet another example, the control circuitry 334 can communicate with the user device 310 through a wireless communication protocol such as ZigBee, Z-Wave, or another wireless communication protocol suitable for the application. As another example, the control circuitry 334 can communicate with the user device 310 through a wired connection such as, for example, a USB connector or another wired connection suitable for the application.

The user device 310 can display a variety of information and statistics related to sleep, or user 308's interaction with the bed 302. For example, a user interface displayed by the user device 310 can present information including amount of sleep for the user 308 over a period of time (e.g., a single evening, a week, a month, etc.) amount of deep sleep, ratio of deep sleep to restless sleep, time lapse between the user 308 getting into bed and the user 308 falling asleep, total amount of time spent in the bed 302 for a given period of time, heart rate for the user 308 over a period of time, respiration rate for the user 308 over a period of time, or other information related to user interaction with the bed 302 by the user 308 or one or more other users of the bed 302. In some implementations, information for multiple users can be presented on the user device 310, for example information for a first user positioned over the air chamber 306a can be presented along with information for a second user positioned over the air chamber 306b. In some implementations, the information presented on the user device 310 can vary according to the age of the user 308. For example, the information presented on the user device 310 can evolve with the age of the user 308 such that different information is presented on the user device 310 as the user 308 ages as a child or an adult.

The user device 310 can also be used as an interface for the control circuitry 334 of the bed 302 to allow the user 308 to enter information. The information entered by the user 308 can be used by the control circuitry 334 to provide better information to the user or to various control signals for controlling functions of the bed 302 or other devices. For example, the user can enter information such as weight, height, and age and the control circuitry 334 can use this information to provide the user 308 with a comparison of the user's tracked sleep information to sleep information of other people having similar weights, heights, and/or ages as the user 308. As another example, the user 308 can use the user device 310 as an interface for controlling air pressure of the air chambers 306a and 306b, for controlling various recline or incline positions of the bed 302, for controlling temperature of one or more surface temperature control devices of the bed 302, or for allowing the control circuitry 334 to generate control signals for other devices (as described in greater detail below).

In some implementations, control circuitry 334 of the bed 302 (e.g., control circuitry 334 integrated into the pump 304) can communicate with other devices or systems in addition to or instead of the user device 310. For example, the control circuitry 334 can communicate with the television 312, a lighting system 314, a thermostat 316, a security system 318, or other house hold devices such as an oven 322, a coffee maker 324, a lamp 326, and a nightlight 328. Other examples of devices and/or systems that the control circuitry 334 can communicate with include a system for controlling window blinds 330, one or more devices for detecting or controlling the states of one or more doors 332 (such as detecting if a door is open, detecting if a door is locked, or automatically locking a door), and a system for controlling a garage door 320 (e.g., control circuitry 334 integrated with a garage door opener for identifying an open or closed state of the garage door 320 and for causing the garage door opener to open or close the garage door 320). Communications between the control circuitry 334 of the bed 302 and other devices can occur through a network (e.g., a LAN or the Internet) or as point-to-point communication (e.g., using Bluetooth, radio communication, or a wired connection). In some implementations, control circuitry 334 of different beds 302 can communicate with different sets of devices. For example, a kid bed may not communicate with and/or control the same devices as an adult bed. In some embodiments, the bed 302 can evolve with the age of the user such that the control circuitry 334 of the bed 302 communicates with different devices as a function of age of the user.

The control circuitry 334 can receive information and inputs from other devices/systems and use the received information and inputs to control actions of the bed 302 or other devices. For example, the control circuitry 334 can receive information from the thermostat 316 indicating a current environmental temperature for a house or room in which the bed 302 is located. The control circuitry 334 can use the received information (along with other information) to determine if a temperature of all or a portion of the surface of the bed 302 should be raised or lowered. The control circuitry 334 can then cause a heating or cooling mechanism of the bed 302 to raise or lower the temperature of the surface of the bed 302. For example, the user 308 can indicate a desired sleeping temperature of 74 degrees while a second user of the bed 302 indicates a desired sleeping temperature of 72 degrees. The thermostat 316 can indicate to the control circuitry 334 that the current temperature of the bedroom is 72 degrees. The control circuitry 334 can identify that the user 308 has indicated a desired sleeping temperature of 74 degrees, and send control signals to a heating pad located on the user 308's side of the bed to raise the temperature of the portion of the surface of the bed 302 where the user 308 is located to raise the temperature of the user 308's sleeping surface to the desired temperature.

The control circuitry 334 can also generate control signals controlling other devices and propagate the control signals to the other devices. In some implementations, the control signals are generated based on information collected by the control circuitry 334, including information related to user interaction with the bed 302 by the user 308 and/or one or more other users. In some implementations, information collected from one or more other devices other than the bed 302 are used when generating the control signals. For example, information relating to environmental occurrences (e.g., environmental temperature, environmental noise level, and environmental light level), time of day, time of year, day of the week, or other information can be used when generating control signals for various devices in communication with the control circuitry 334 of the bed 302. For example, information on the time of day can be combined with information relating to movement and bed presence of the user 308 to generate control signals for the lighting system 314. In some implementations, rather than or in addition to providing control signals for one or more other devices, the control circuitry 334 can provide collected information (e.g., information related to user movement, bed presence, sleep state, or biometric signals for the user 308) to one or more other devices to allow the one or more other devices to utilize the collected information when generating control signals. For example, control circuitry 334 of the bed 302 can provide information relating to user interactions with the bed 302 by the user 308 to a central controller (not shown) that can use the provided information to generate control signals for various devices, including the bed 302.

Still referring to FIG. 3, the control circuitry 334 of the bed 302 can generate control signals for controlling actions of other devices, and transmit the control signals to the other devices in response to information collected by the control circuitry 334, including bed presence of the user 308, sleep state of the user 308, and other factors. For example, control circuitry 334 integrated with the pump 304 can detect a feature of a mattress of the bed 302, such as an increase in pressure in the air chamber 306b, and use this detected increase in air pressure to determine that the user 308 is present on the bed 302. In some implementations, the control circuitry 334 can identify a heart rate or respiratory rate for the user 308 to identify that the increase in pressure is due to a person sitting, laying, or otherwise resting on the bed 302 rather than an inanimate object (such as a suitcase) having been placed on the bed 302. In some implementations, the information indicating user bed presence is combined with other information to identify a current or future likely state for the user 308. For example, a detected user bed presence at 11:00 am can indicate that the user is sitting on the bed (e.g., to tie her shoes, or to read a book) and does not intend to go to sleep, while a detected user bed presence at 10:00 pm can indicate that the user 308 is in bed for the evening and is intending to fall asleep soon. As another example, if the control circuitry 334 detects that the user 308 has left the bed 302 at 6:30 am (e.g., indicating that the user 308 has woken up for the day), and then later detects user bed presence of the user 308 at 7:30 am, the control circuitry 334 can use this information that the newly detected user bed presence is likely temporary (e.g., while the user 308 ties her shoes before heading to work) rather than an indication that the user 308 is intending to stay on the bed 302 for an extended period.

In some implementations, the control circuitry 334 is able to use collected information (including information related to user interaction with the bed 302 by the user 308, as well as environmental information, time information, and input received from the user) to identify use patterns for the user 308. For example, the control circuitry 334 can use information indicating bed presence and sleep states for the user 308 collected over a period of time to identify a sleep pattern for the user. For example, the control circuitry 334 can identify that the user 308 generally goes to bed between 9:30 pm and 10:00 pm, generally falls asleep between 10:00 pm and 11:00 pm, and generally wakes up between 6:30 am and 6:45 am based on information indicating user presence and biometrics for the user 308 collected over a week. The control circuitry 334 can use identified patterns for a user to better process and identify user interactions with the bed 302 by the user 308.

For example, given the above example user bed presence, sleep, and wake patterns for the user 308, if the user 308 is detected as being on the bed at 3:00 pm, the control circuitry 334 can determine that the user's presence on the bed is only temporary, and use this determination to generate different control signals than would be generated if the control circuitry 334 determined that the user 308 was in bed for the evening. As another example, if the control circuitry 334 detects that the user 308 has gotten out of bed at 3:00 am, the control circuitry 334 can use identified patterns for the user 308 to determine that the user has only gotten up temporarily (for example, to use the rest room, or get a glass of water) and is not up for the day. By contrast, if the control circuitry 334 identifies that the user 308 has gotten out of the bed 302 at 6:40 am, the control circuitry 334 can determine that the user is up for the day and generate a different set of control signals than those that would be generated if it were determined that the user 308 were only getting out of bed temporarily (as would be the case when the user 308 gets out of the bed 302 at 3:00 am). For other users 308, getting out of the bed 302 at 3:00 am can be the normal wake-up time, which the control circuitry 334 can learn and respond to accordingly.

As described above, the control circuitry 334 for the bed 302 can generate control signals for control functions of various other devices. The control signals can be generated, at least in part, based on detected interactions by the user 308 with the bed 302, as well as other information including time, date, temperature, etc. For example, the control circuitry 334 can communicate with the television 312, receive information from the television 312, and generate control signals for controlling functions of the television 312. For example, the control circuitry 334 can receive an indication from the television 312 that the television 312 is currently on. If the television 312 is located in a different room from the bed 302, the control circuitry 334 can generate a control signal to turn the television 312 off upon making a determination that the user 308 has gone to bed for the evening. For example, if bed presence of the user 308 on the bed 302 is detected during a particular time range (e.g., between 8:00 pm and 7:00 am) and persists for longer than a threshold period of time (e.g., 10 minutes) the control circuitry 334 can use this information to determine that the user 308 is in bed for the evening. If the television 312 is on (as indicated by communications received by the control circuitry 334 of the bed 302 from the television 312) the control circuitry 334 can generate a control signal to turn the television 312 off.

The control signals can then be transmitted to the television (e.g., through a directed communication link between the television 312 and the control circuitry 334 or through a network). As another example, rather than turning off the television 312 in response to detection of user bed presence, the control circuitry 334 can generate a control signal that causes the volume of the television 312 to be lowered by a pre-specified amount.

As another example, upon detecting that the user 308 has left the bed 302 during a specified time range (e.g., between 6:00 am and 8:00 am) the control circuitry 334 can generate control signals to cause the television 312 to turn on and tune to a pre-specified channel (e.g., the user 308 has indicated a preference for watching the morning news upon getting out of bed in the morning). The control circuitry 334 can generate the control signal and transmit the signal to the television 312 to cause the television 312 to turn on and tune to the desired station (which could be stored at the control circuitry 334, the television 312, or another location). As another example, upon detecting that the user 308 has gotten up for the day, the control circuitry 334 can generate and transmit control signals to cause the television 312 to turn on and begin playing a previously recorded program from a digital video recorder (DVR) in communication with the television 312.

As another example, if the television 312 is in the same room as the bed 302, the control circuitry 334 does not cause the television 312 to turn off in response to detection of user bed presence. Rather, the control circuitry 334 can generate and transmit control signals to cause the television 312 to turn off in response to determining that the user 308 is asleep. For example, the control circuitry 334 can monitor biometric signals of the user 308 (e.g., motion, heart rate, respiration rate) to determine that the user 308 has fallen asleep. Upon detecting that the user 308 is sleeping, the control circuitry 334 generates and transmits a control signal to turn the television 312 off. As another example, the control circuitry 334 can generate the control signal to turn off the television 312 after a threshold period of time after the user 308 has fallen asleep (e.g., 10 minutes after the user has fallen asleep). As another example, the control circuitry 334 generates control signals to lower the volume of the television 312 after determining that the user 308 is asleep. As yet another example, the control circuitry 334 generates and transmits a control signal to cause the television to gradually lower in volume over a period of time and then turn off in response to determining that the user 308 is asleep.

In some implementations, the control circuitry 334 can similarly interact with other media devices, such as computers, tablets, smart phones, stereo systems, etc. For example, upon detecting that the user 308 is asleep, the control circuitry 334 can generate and transmit a control signal to the user device 310 to cause the user device 310 to turn off, or turn down the volume on a video or audio file being played by the user device 310.

The control circuitry 334 can additionally communicate with the lighting system 314, receive information from the lighting system 314, and generate control signals for controlling functions of the lighting system 314. For example, upon detecting user bed presence on the bed 302 during a certain time frame (e.g., between 8:00 pm and 7:00 am) that lasts for longer than a threshold period of time (e.g., 10 minutes) the control circuitry 334 of the bed 302 can determine that the user 308 is in bed for the evening. In response to this determination, the control circuitry 334 can generate control signals to cause lights in one or more rooms other than the room in which the bed 302 is located to switch off. The control signals can then be transmitted to the lighting system 314 and executed by the lighting system 314 to cause the lights in the indicated rooms to shut off. For example, the control circuitry 334 can generate and transmit control signals to turn off lights in all common rooms, but not in other bedrooms. As another example, the control signals generated by the control circuitry 334 can indicate that lights in all rooms other than the room in which the bed 302 is located are to be turned off, while one or more lights located outside of the house containing the bed 302 are to be turned on, in response to determining that the user 308 is in bed for the evening. Additionally, the control circuitry 334 can generate and transmit control signals to cause the nightlight 328 to turn on in response to determining user 308 bed presence or whether the user 308 is asleep. As another example, the control circuitry 334 can generate first control signals for turning off a first set of lights (e.g., lights in common rooms) in response to detecting user bed presence, and second control signals for turning off a second set of lights (e.g., lights in the room in which the bed 302 is located) in response to detecting that the user 308 is asleep.

In some implementations, in response to determining that the user 308 is in bed for the evening, the control circuitry 334 of the bed 302 can generate control signals to cause the lighting system 314 to implement a sunset lighting scheme in the room in which the bed 302 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 308 to sleep when the control circuitry 334 has determined that the user 308 is in bed for the evening.

The control circuitry 334 can also be configured to implement a sunrise lighting scheme when the user 308 wakes up in the morning. The control circuitry 334 can determine that the user 308 is awake for the day, for example, by detecting that the user 308 has gotten off of the bed 302 (i.e., is no longer present on the bed 302) during a specified time frame (e.g., between 6:00 am and 8:00 am). As another example, the control circuitry 334 can monitor movement, heart rate, respiratory rate, or other biometric signals of the user 308 to determine that the user 308 is awake even though the user 308 has not gotten out of bed. If the control circuitry 334 detects that the user is awake during a specified time frame, the control circuitry 334 can determine that the user 308 is awake for the day. The specified time frame can be, for example, based on previously recorded user bed presence information collected over a period of time (e.g., two weeks) that indicates that the user 308 usually wakes up for the day between 6:30 am and 7:30 am. In response to the control circuitry 334 determining that the user 308 is awake, the control circuitry 334 can generate control signals to cause the lighting system 314 to implement the sunrise lighting scheme in the bedroom in which the bed 302 is located. The sunrise lighting scheme can include, for example, turning on lights (e.g., the lamp 326, or other lights in the bedroom). The sunrise lighting scheme can further include gradually increasing the level of light in the room where the bed 302 is located (or in one or more other rooms). The sunrise lighting scheme can also include only turning on lights of specified colors. For example, the sunrise lighting scheme can include lighting the bedroom with blue light to gently assist the user 308 in waking up and becoming active.

In some implementations, the control circuitry 334 can generate different control signals for controlling actions of one or more components, such as the lighting system 314, depending on a time of day that user interactions with the bed 302 are detected. For example, the control circuitry 334 can use historical user interaction information for interactions between the user 308 and the bed 302 to determine that the user 308 usually falls asleep between 10:00 pm and 11:00 pm and usually wakes up between 6:30 am and 7:30 am on weekdays. The control circuitry 334 can use this information to generate a first set of control signals for controlling the lighting system 314 if the user 308 is detected as getting out of bed at 3:00 am and to generate a second set of control signals for controlling the lighting system 314 if the user 308 is detected as getting out of bed after 6:30 am. For example, if the user 308 gets out of bed prior to 6:30 am, the control circuitry 334 can turn on lights that guide the user 308's route to a restroom. As another example, if the user 308 gets out of bed prior to 6:30 am, the control circuitry 334 can turn on lights that guide the user 308's route to the kitchen (which can include, for example, turning on the nightlight 328, turning on under bed lighting, or turning on the lamp 326).

As another example, if the user 308 gets out of bed after 6:30 am, the control circuitry 334 can generate control signals to cause the lighting system 314 to initiate a sunrise lighting scheme, or to turn on one or more lights in the bedroom and/or other rooms. In some implementations, if the user 308 is detected as getting out of bed prior to a specified morning rise time for the user 308, the control circuitry 334 causes the lighting system 314 to turn on lights that are dimmer than lights that are turned on by the lighting system 314 if the user 308 is detected as getting out of bed after the specified morning rise time. Causing the lighting system 314 to only turn on dim lights when the user 308 gets out of bed during the night (i.e., prior to normal rise time for the user 308) can prevent other occupants of the house from being woken by the lights while still allowing the user 308 to see in order to reach the restroom, kitchen, or another destination within the house.

The historical user interaction information for interactions between the user 308 and the bed 302 can be used to identify user sleep and awake time frames. For example, user bed presence times and sleep times can be determined for a set period of time (e.g., two weeks, a month, etc.). The control circuitry 334 can then identify a typical time range or time frame in which the user 308 goes to bed, a typical time frame for when the user 308 falls asleep, and a typical time frame for when the user 308 wakes up (and in some cases, different time frames for when the user 308 wakes up and when the user 308 actually gets out of bed). In some implementations, buffer time can be added to these time frames. For example, if the user is identified as typically going to bed between 10:00 pm and 10:30 pm, a buffer of a half hour in each direction can be added to the time frame such that any detection of the user getting onto the bed between 9:30 pm and 11:00 pm is interpreted as the user 308 going to bed for the evening. As another example, detection of bed presence of the user 308 starting from a half hour before the earliest typical time that the user 308 goes to bed extending until the typical wake up time (e.g., 6:30 am) for the user can be interpreted as the user going to bed for the evening. For example, if the user typically goes to bed between 10:00 pm and 10:30 pm, if the user's bed presence is sensed at 12:30 am one night, that can be interpreted as the user getting into bed for the evening even though this is outside of the user's typical time frame for going to bed because it has occurred prior to the user's normal wake up time. In some implementations, different time frames are identified for different times of the year (e.g., earlier bed time during winter vs. summer) or at different times of the week (e.g., user wakes up earlier on weekdays than on weekends).

The control circuitry 334 can distinguish between the user 308 going to bed for an extended period (such as for the night) as opposed to being present on the bed 302 for a shorter period (such as for a nap) by sensing duration of presence of the user 308. In some examples, the control circuitry 334 can distinguish between the user 308 going to bed for an extended period (such as for the night) as opposed to going to bed for a shorter period (such as for a nap) by sensing duration of sleep of the user 308. For example, the control circuitry 334 can set a time threshold whereby if the user 308 is sensed on the bed 302 for longer than the threshold, the user 308 is considered to have gone to bed for the night. In some examples, the threshold can be about 2 hours, whereby if the user 308 is sensed on the bed 302 for greater than 2 hours, the control circuitry 334 registers that as an extended sleep event. In other examples, the threshold can be greater than or less than two hours.

The control circuitry 334 can detect repeated extended sleep events to determine a typical bed time range of the user 308 automatically, without requiring the user 308 to enter a bed time range. This can allow the control circuitry 334 to accurately estimate when the user 308 is likely to go to bed for an extended sleep event, regardless of whether the user 308 typically goes to bed using a traditional sleep schedule or a non-traditional sleep schedule. The control circuitry 334 can then use knowledge of the bed time range of the user 308 to control one or more components (including components of the bed 302 and/or non-bed peripherals) differently based on sensing bed presence during the bed time range or outside of the bed time range.

In some examples, the control circuitry 334 can automatically determine the bed time range of the user 308 without requiring user inputs. In some examples, the control circuitry 334 can determine the bed time range of the user 308 automatically and in combination with user inputs. In some examples, the control circuitry 334 can set the bed time range directly according to user inputs. In some examples, the control circuitry 334 can associate different bed times with different days of the week. In each of these examples, the control circuitry 334 can control one or more components (such as the lighting system 314, the thermostat 316, the security system 318, the oven 322, the coffee maker 324, the lamp 326, and the nightlight 328), as a function of sensed bed presence and the bed time range.

The control circuitry 334 can additionally communicate with the thermostat 316, receive information from the thermostat 316, and generate control signals for controlling functions of the thermostat 316. For example, the user 308 can indicate user preferences for different temperatures at different times, depending on the sleep state or bed presence of the user 308. For example, the user 308 may prefer an environmental temperature of 72 degrees when out of bed, 70 degrees when in bed but awake, and 68 degrees when sleeping. The control circuitry 334 of the bed 302 can detect bed presence of the user 308 in the evening and determine that the user 308 is in bed for the night. In response to this determination, the control circuitry 334 can generate control signals to cause the thermostat to change the temperature to 70 degrees. The control circuitry 334 can then transmit the control signals to the thermostat 316. Upon detecting that the user 308 is in bed during the bed time range or asleep, the control circuitry 334 can generate and transmit control signals to cause the thermostat 316 to change the temperature to 68. The next morning, upon determining that the user is awake for the day (e.g., the user 308 gets out of bed after 6:30 am) the control circuitry 334 can generate and transmit control circuitry 334 to cause the thermostat to change the temperature to 72 degrees.

In some implementations, the control circuitry 334 can similarly generate control signals to cause one or more heating or cooling elements on the surface of the bed 302 to change temperature at various times, either in response to user interaction with the bed 302 or at various pre-programmed times. For example, the control circuitry 334 can activate a heating element to raise the temperature of one side of the surface of the bed 302 to 73 degrees when it is detected that the user 308 has fallen asleep. As another example, upon determining that the user 308 is up for the day, the control circuitry 334 can turn off a heating or cooling element. As yet another example, the user 308 can pre-program various times at which the temperature at the surface of the bed should be raised or lowered. For example, the user can program the bed 302 to raise the surface temperature to 76 degrees at 10:00 pm, and lower the surface temperature to 68 degrees at 11:30 pm.

In some implementations, in response to detecting user bed presence of the user 308 and/or that the user 308 is asleep, the control circuitry 334 can cause the thermostat 316 to change the temperature in different rooms to different values. For example, in response to determining that the user 308 is in bed for the evening, the control circuitry 334 can generate and transmit control signals to cause the thermostat 316 to set the temperature in one or more bedrooms of the house to 72 degrees and set the temperature in other rooms to 67 degrees.

The control circuitry 334 can also receive temperature information from the thermostat 316 and use this temperature information to control functions of the bed 302 or other devices. For example, as discussed above, the control circuitry 334 can adjust temperatures of heating elements included in the bed 302 in response to temperature information received from the thermostat 316.

In some implementations, the control circuitry 334 can generate and transmit control signals for controlling other temperature control systems. For example, in response to determining that the user 308 is awake for the day, the control circuitry 334 can generate and transmit control signals for causing floor heating elements to activate. For example, the control circuitry 334 can cause a floor heating system for a master bedroom to turn on in response to determining that the user 308 is awake for the day.

The control circuitry 334 can additionally communicate with the security system 318, receive information from the security system 318, and generate control signals for controlling functions of the security system 318. For example, in response to detecting that the user 308 in is bed for the evening, the control circuitry 334 can generate control signals to cause the security system to engage or disengage security functions. The control circuitry 334 can then transmit the control signals to the security system 318 to cause the security system 318 to engage. As another example, the control circuitry 334 can generate and transmit control signals to cause the security system 318 to disable in response to determining that the user 308 is awake for the day (e.g., user 308 is no longer present on the bed 302 after 6:00 am). In some implementations, the control circuitry 334 can generate and transmit a first set of control signals to cause the security system 318 to engage a first set of security features in response to detecting user bed presence of the user 308, and can generate and transmit a second set of control signals to cause the security system 318 to engage a second set of security features in response to detecting that the user 308 has fallen asleep.

In some implementations, the control circuitry 334 can receive alerts from the security system 318 and indicate the alert to the user 308. For example, the control circuitry 334 can detect that the user 308 is in bed for the evening and in response, generate and transmit control signals to cause the security system 318 to engage or disengage. The security system can then detect a security breach (e.g., someone has opened the door 332 without entering the security code, or someone has opened a window when the security system 318 is engaged). The security system 318 can communicate the security breach to the control circuitry 334 of the bed 302. In response to receiving the communication from the security system 318, the control circuitry 334 can generate control signals to alert the user 308 to the security breach. For example, the control circuitry 334 can cause the bed 302 to vibrate. As another example, the control circuitry 334 can cause portions of the bed 302 to articulate (e.g., cause the head section to raise or lower) in order to wake the user 308 and alert the user to the security breach. As another example, the control circuitry 334 can generate and transmit control signals to cause the lamp 326 to flash on and off at regular intervals to alert the user 308 to the security breach. As another example, the control circuitry 334 can alert the user 308 of one bed 302 regarding a security breach in a bedroom of another bed, such as an open window in a kid's bedroom. As another example, the control circuitry 334 can send an alert to a garage door controller (e.g., to close and lock the door). As another example, the control circuitry 334 can send an alert for the security to be disengaged.

The control circuitry 334 can additionally generate and transmit control signals for controlling the garage door 320 and receive information indicating a state of the garage door 320 (i.e., open or closed). For example, in response to determining that the user 308 is in bed for the evening, the control circuitry 334 can generate and transmit a request to a garage door opener or another device capable of sensing if the garage door 320 is open. The control circuitry 334 can request information on the current state of the garage door 320. If the control circuitry 334 receives a response (e.g., from the garage door opener) indicating that the garage door 320 is open, the control circuitry 334 can either notify the user 308 that the garage door is open, or generate a control signal to cause the garage door opener to close the garage door 320. For example, the control circuitry 334 can send a message to the user device 310 indicating that the garage door is open. As another example, the control circuitry 334 can cause the bed 302 to vibrate. As yet another example, the control circuitry 334 can generate and transmit a control signal to cause the lighting system 314 to cause one or more lights in the bedroom to flash to alert the user 308 to check the user device 310 for an alert (in this example, an alert regarding the garage door 320 being open). Alternatively, or additionally, the control circuitry 334 can generate and transmit control signals to cause the garage door opener to close the garage door 320 in response to identifying that the user 308 is in bed for the evening and that the garage door 320 is open. In some implementations, control signals can vary depend on the age of the user 308.

The control circuitry 334 can similarly send and receive communications for controlling or receiving state information associated with the door 332 or the oven 322. For example, upon detecting that the user 308 is in bed for the evening, the control circuitry 334 can generate and transmit a request to a device or system for detecting a state of the door 332. Information returned in response to the request can indicate various states for the door 332 such as open, closed but unlocked, or closed and locked. If the door 332 is open or closed but unlocked, the control circuitry 334 can alert the user 308 to the state of the door, such as in a manner described above with reference to the garage door 320. Alternatively, or in addition to alerting the user 308, the control circuitry 334 can generate and transmit control signals to cause the door 332 to lock, or to close and lock. If the door 332 is closed and locked, the control circuitry 334 can determine that no further action is needed.

Similarly, upon detecting that the user 308 is in bed for the evening, the control circuitry 334 can generate and transmit a request to the oven 322 to request a state of the oven 322 (e.g., on or off). If the oven 322 is on, the control circuitry 334 can alert the user 308 and/or generate and transmit control signals to cause the oven 322 to turn off. If the oven is already off, the control circuitry 334 can determine that no further action is necessary. In some implementations, different alerts can be generated for different events. For example, the control circuitry 334 can cause the lamp 326 (or one or more other lights, via the lighting system 314) to flash in a first pattern if the security system 318 has detected a breach, flash in a second pattern if garage door 320 is on, flash in a third pattern if the door 332 is open, flash in a fourth pattern if the oven 322 is on, and flash in a fifth pattern if another bed has detected that a user of that bed has gotten up (e.g., that a child of the user 308 has gotten out of bed in the middle of the night as sensed by a sensor in the bed 302 of the child). Other examples of alerts that can be processed by the control circuitry 334 of the bed 302 and communicated to the user include a smoke detector detecting smoke (and communicating this detection of smoke to the control circuitry 334), a carbon monoxide tester detecting carbon monoxide, a heater malfunctioning, or an alert from any other device capable of communicating with the control circuitry 334 and detecting an occurrence that should be brought to the user 308's attention.

The control circuitry 334 can also communicate with a system or device for controlling a state of the window blinds 330. For example, in response to determining that the user 308 is in bed for the evening, the control circuitry 334 can generate and transmit control signals to cause the window blinds 330 to close. As another example, in response to determining that the user 308 is up for the day (e.g., user has gotten out of bed after 6:30 am) the control circuitry 334 can generate and transmit control signals to cause the window blinds 330 to open. By contrast, if the user 308 gets out of bed prior to a normal rise time for the user 308, the control circuitry 334 can determine that the user 308 is not awake for the day and does not generate control signals for causing the window blinds 330 to open. As yet another example, the control circuitry 334 can generate and transmit control signals that cause a first set of blinds to close in response to detecting user bed presence of the user 308 and a second set of blinds to close in response to detecting that the user 308 is asleep.

The control circuitry 334 can generate and transmit control signals for controlling functions of other household devices in response to detecting user interactions with the bed 302. For example, in response to determining that the user 308 is awake for the day, the control circuitry 334 can generate and transmit control signals to the coffee maker 324 to cause the coffee maker 324 to begin brewing coffee. As another example, the control circuitry 334 can generate and transmit control signals to the oven 322 to cause the oven to begin preheating (for users that like fresh baked bread in the morning). As another example, the control circuitry 334 can use information indicating that the user 308 is awake for the day along with information indicating that the time of year is currently winter and/or that the outside temperature is below a threshold value to generate and transmit control signals to cause a car engine block heater to turn on.

As another example, the control circuitry 334 can generate and transmit control signals to cause one or more devices to enter a sleep mode in response to detecting user bed presence of the user 308, or in response to detecting that the user 308 is asleep. For example, the control circuitry 334 can generate control signals to cause a mobile phone of the user 308 to switch into sleep mode. The control circuitry 334 can then transmit the control signals to the mobile phone. Later, upon determining that the user 308 is up for the day, the control circuitry 334 can generate and transmit control signals to cause the mobile phone to switch out of sleep mode.

In some implementations, the control circuitry 334 can communicate with one or more noise control devices. For example, upon determining that the user 308 is in bed for the evening, or that the user 308 is asleep, the control circuitry 334 can generate and transmit control signals to cause one or more noise cancelation devices to activate. The noise cancelation devices can, for example, be included as part of the bed 302 or located in the bedroom with the bed 302. As another example, upon determining that the user 308 is in bed for the evening or that the user 308 is asleep, the control circuitry 334 can generate and transmit control signals to turn the volume on, off, up, or down, for one or more sound generating devices, such as a stereo system radio, computer, tablet, etc.

Additionally, functions of the bed 302 are controlled by the control circuitry 334 in response to user interactions with the bed 302. For example, the bed 302 can include an adjustable foundation and an articulation controller configured to adjust the position of one or more portions of the bed 302 by adjusting the adjustable foundation that supports the bed. For example, the articulation controller can adjust the bed 302 from a flat position to a position in which a head portion of a mattress of the bed 302 is inclined upward (e.g., to facilitate a user sitting up in bed and/or watching television). In some implementations, the bed 302 includes multiple separately articulable sections. For example, portions of the bed corresponding to the locations of the air chambers 306a and 306b can be articulated independently from each other, to allow one person positioned on the bed 302 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 302 can include more than one zone that can be independently adjusted. The articulation controller can also be configured to provide different levels of massage to one or more users on the bed 302 or to cause the bed to vibrate to communicate alerts to the user 308 as described above.

The control circuitry 334 can adjust positions (e.g., incline and decline positions for the user 308 and/or an additional user of the bed 302) in response to user interactions with the bed 302. For example, the control circuitry 334 can cause the articulation controller to adjust the bed 302 to a first recline position for the user 308 in response to sensing user bed presence for the user 308. The control circuitry 334 can cause the articulation controller to adjust the bed 302 to a second recline position (e.g., a less reclined, or flat position) in response to determining that the user 308 is asleep. As another example, the control circuitry 334 can receive a communication from the television 312 indicating that the user 308 has turned off the television 312, and in response the control circuitry 334 can cause the articulation controller to adjust the position of the bed 302 to a preferred user sleeping position (e.g., due to the user turning off the television 312 while the user 308 is in bed indicating that the user 308 wishes to go to sleep).

In some implementations, the control circuitry 334 can control the articulation controller so as to wake up one user of the bed 302 without waking another user of the bed 302. For example, the user 308 and a second user of the bed 302 can each set distinct wakeup times (e.g., 6:30 am and 7:15 am respectively). When the wakeup time for the user 308 is reached, the control circuitry 334 can cause the articulation controller to vibrate or change the position of only a side of the bed on which the user 308 is located to wake the user 308 without disturbing the second user. When the wakeup time for the second user is reached, the control circuitry 334 can cause the articulation controller to vibrate or change the position of only the side of the bed on which the second user is located. Alternatively, when the second wakeup time occurs, the control circuitry 334 can utilize other methods (such as audio alarms, or turning on the lights) to wake the second user since the user 308 is already awake and therefore will not be disturbed when the control circuitry 334 attempts to wake the second user.

Still referring to FIG. 3, the control circuitry 334 for the bed 302 can utilize information for interactions with the bed 302 by multiple users to generate control signals for controlling functions of various other devices. For example, the control circuitry 334 can wait to generate control signals for, for example, engaging the security system 318, or instructing the lighting system 314 to turn off lights in various rooms until both the user 308 and a second user are detected as being present on the bed 302. As another example, the control circuitry 334 can generate a first set of control signals to cause the lighting system 314 to turn off a first set of lights upon detecting bed presence of the user 308 and generate a second set of control signals for turning off a second set of lights in response to detecting bed presence of a second user. As another example, the control circuitry 334 can wait until it has been determined that both the user 308 and a second user are awake for the day before generating control signals to open the window blinds 330. As yet another example, in response to determining that the user 308 has left the bed and is awake for the day, but that a second user is still sleeping, the control circuitry 334 can generate and transmit a first set of control signals to cause the coffee maker 324 to begin brewing coffee, to cause the security system 318 to deactivate, to turn on the lamp 326, to turn off the nightlight 328, to cause the thermostat 316 to raise the temperature in one or more rooms to 72 degrees, and to open blinds (e.g., the window blinds 330) in rooms other than the bedroom in which the bed 302 is located. Later, in response to detecting that the second user is no longer present on the bed (or that the second user is awake) the control circuitry 334 can generate and transmit a second set of control signals to, for example, cause the lighting system 314 to turn on one or more lights in the bedroom, to cause window blinds in the bedroom to open, and to turn on the television 312 to a pre-specified channel.

Examples of Data Processing Systems Associated with a Bed

Described here are examples of systems and components that can be used for data processing tasks that are, for example, associated with a bed. In some cases, multiple examples of a particular component or group of components are presented. Some of these examples are redundant and/or mutually exclusive alternatives. Connections between components are shown as examples to illustrate possible network configurations for allowing communication between components. Different formats of connections can be used as technically needed or desired. The connections generally indicate a logical connection that can be created with any technologically feasible format. For example, a network on a motherboard can be created with a printed circuit board, wireless data connections, and/or other types of network connections. Some logical connections are not shown for clarity. For example, connections with power supplies and/or computer readable memory may not be shown for clarities sake, as many or all elements of a particular component may need to be connected to the power supplies and/or computer readable memory.

Figure 4A:
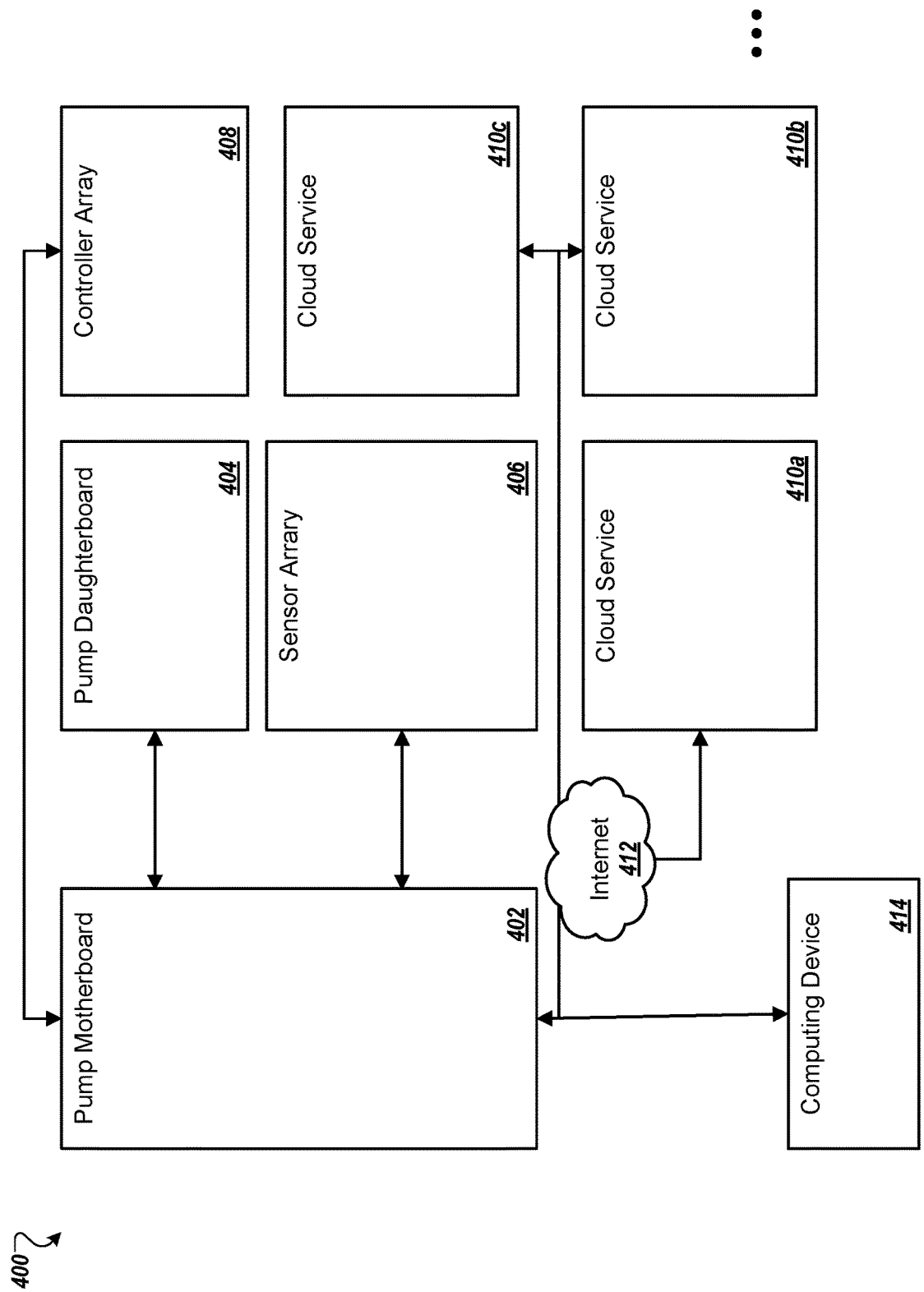
FIGS. 4A and 4B are block diagrams of example data processing systems that can be associated with a bed.

FIG. 4A is a block diagram of an example of a data processing system 400 that can be associated with a bed system, including those described above with respect to FIGS. 1-3. This system 400 includes a pump motherboard 402 and a pump daughterboard 404. The system 400 includes a sensor array 406 that can include one or more sensors configured to sense physical phenomenon of the environment and/or bed, and to report such sensing back to the pump motherboard 402 for, for example, analysis. The system 400 also includes a controller array 408 that can include one or more controllers configured to control logic-controlled devices of the bed and/or environment. The pump motherboard 400 can be in communication with one or more computing devices 414 and one or more cloud services 410 over local networks, the Internet 412, or otherwise as is technically appropriate. Each of these components will be described in more detail, some with multiple example configurations, below.

In this example, a pump motherboard 402 and a pump daughterboard 404 are communicably coupled. They can be conceptually described as a center or hub of the system 400, with the other components conceptually described as spokes of the system 400. In some configurations, this can mean that each of the spoke components communicates primarily or exclusively with the pump motherboard 402. For example, a sensor of the sensor array may not be configured to, or may not be able to, communicate directly with a corresponding controller. Instead, each spoke component can communicate with the motherboard 402. The sensor of the sensor array 406 can report a sensor reading to the motherboard 402, and the motherboard 402 can determine that, in response, a controller of the controller array 408 should adjust some parameters of a logic controlled device or otherwise modify a state of one or more peripheral devices. In one case, if the temperature of the bed is determined to be too hot, the pump motherboard 402 can determine that a temperature controller should cool the bed.

One advantage of a hub-and-spoke network configuration, sometimes also referred to as a star-shaped network, is a reduction in network traffic compared to, for example, a mesh network with dynamic routing. If a particular sensor generates a large, continuous stream of traffic, that traffic may only be transmitted over one spoke of the network to the motherboard 402. The motherboard 402 can, for example, marshal that data and condense it to a smaller data format for retransmission for storage in a cloud service 410. Additionally or alternatively, the motherboard 402 can generate a single, small, command message to be sent down a different spoke of the network in response to the large stream. For example, if the large stream of data is a pressure reading that is transmitted from the sensor array 406 a few times a second, the motherboard 402 can respond with a single command message to the controller array to increase the pressure in an air chamber. In this case, the single command message can be orders of magnitude smaller than the stream of pressure readings.

As another advantage, a hub-and-spoke network configuration can allow for an extensible network that can accommodate components being added, removed, failing, etc. This can allow, for example, more, fewer, or different sensors in the sensor array 406, controllers in the controller array 408, computing devices 414, and/or cloud services 410. For example, if a particular sensor fails or is deprecated by a newer version of the sensor, the system 400 can be configured such that only the motherboard 402 needs to be updated about the replacement sensor. This can allow, for example, product differentiation where the same motherboard 402 can support an entry level product with fewer sensors and controllers, a higher value product with more sensors and controllers, and customer personalization where a customer can add their own selected components to the system 400.

Additionally, a line of air bed products can use the system 400 with different components. In an application in which every air bed in the product line includes both a central logic unit and a pump, the motherboard 402 (and optionally the daughterboard 404) can be designed to fit within a single, universal housing. Then, for each upgrade of the product in the product line, additional sensors, controllers, cloud services, etc., can be added. Design, manufacturing, and testing time can be reduced by designing all products in a product line from this base, compared to a product line in which each product has a bespoke logic control system.

Each of the components discussed above can be realized in a wide variety of technologies and configurations. Below, some examples of each component will be further discussed. In some alternatives, two or more of the components of the system 400 can be realized in a single alternative component; some components can be realized in multiple, separate components; and/or some functionality can be provided by different components.

Figure 4B:
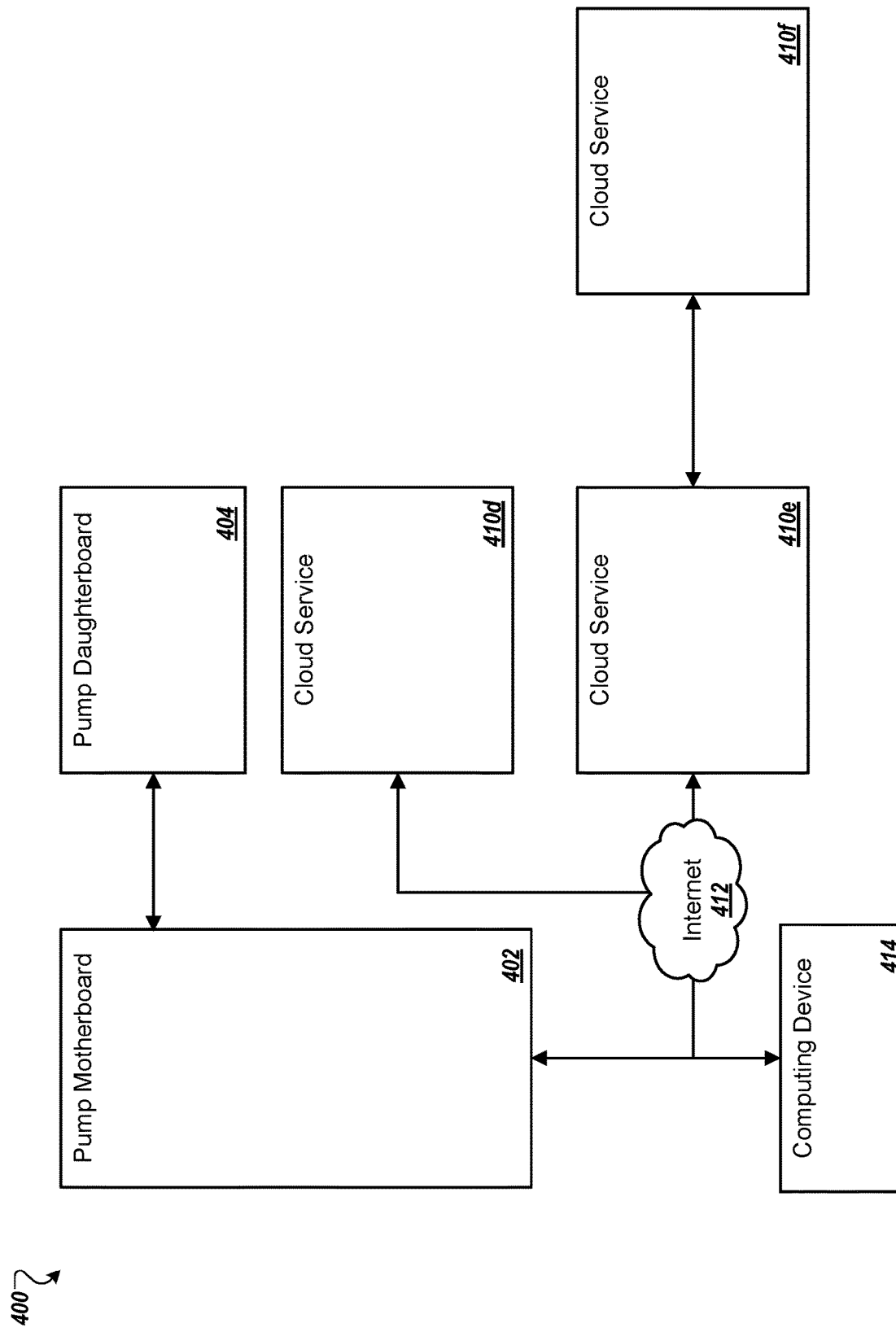

FIG. 4B is a block diagram showing some communication paths of the data processing system 400. As previously described, the motherboard 402 and the pump daughterboard 404 may act as a hub for peripheral devices and cloud services of the system 400. In cases in which the pump daughterboard 404 communicates with cloud services or other components, communications from the pump daughterboard 404 may be routed through the pump motherboard 402. This may allow, for example, the bed to have only a single connection with the internet 412. The computing device 414 may also have a connection to the internet 412, possibly through the same gateway used by the bed and/or possibly through a different gateway (e.g., a cell service provider).

Previously, a number of cloud services 410 were described. As shown in FIG. 4B, some cloud services, such as cloud services 410*d* and 410*e*, may be configured such that the pump motherboard 402 can communicate with the cloud service directly—that is the motherboard 402 may communicate with a cloud service 410 without having to use another cloud service 410 as an intermediary. Additionally or alternatively, some cloud services 410, for example cloud service 410f, may only be reachable by the pump motherboard 402 through an intermediary cloud service, for example cloud service 410e. While not shown here, some cloud services 410 may be reachable either directly or indirectly by the pump motherboard 402.

Additionally, some or all of the cloud services 410 may be configured to communicate with other cloud services. This communication may include the transfer of data and/or remote function calls according to any technologically appropriate format. For example, one cloud service 410 may request a copy for another cloud service's 410 data, for example, for purposes of backup, coordination, migration, or for performance of calculations or data mining. In another example, many cloud services 410 may contain data that is indexed according to specific users tracked by the user account cloud 410c and/or the bed data cloud 410a. These cloud services 410 may communicate with the user account cloud 410c and/or the bed data cloud 410a when accessing data specific to a particular user or bed.

Figure 5:
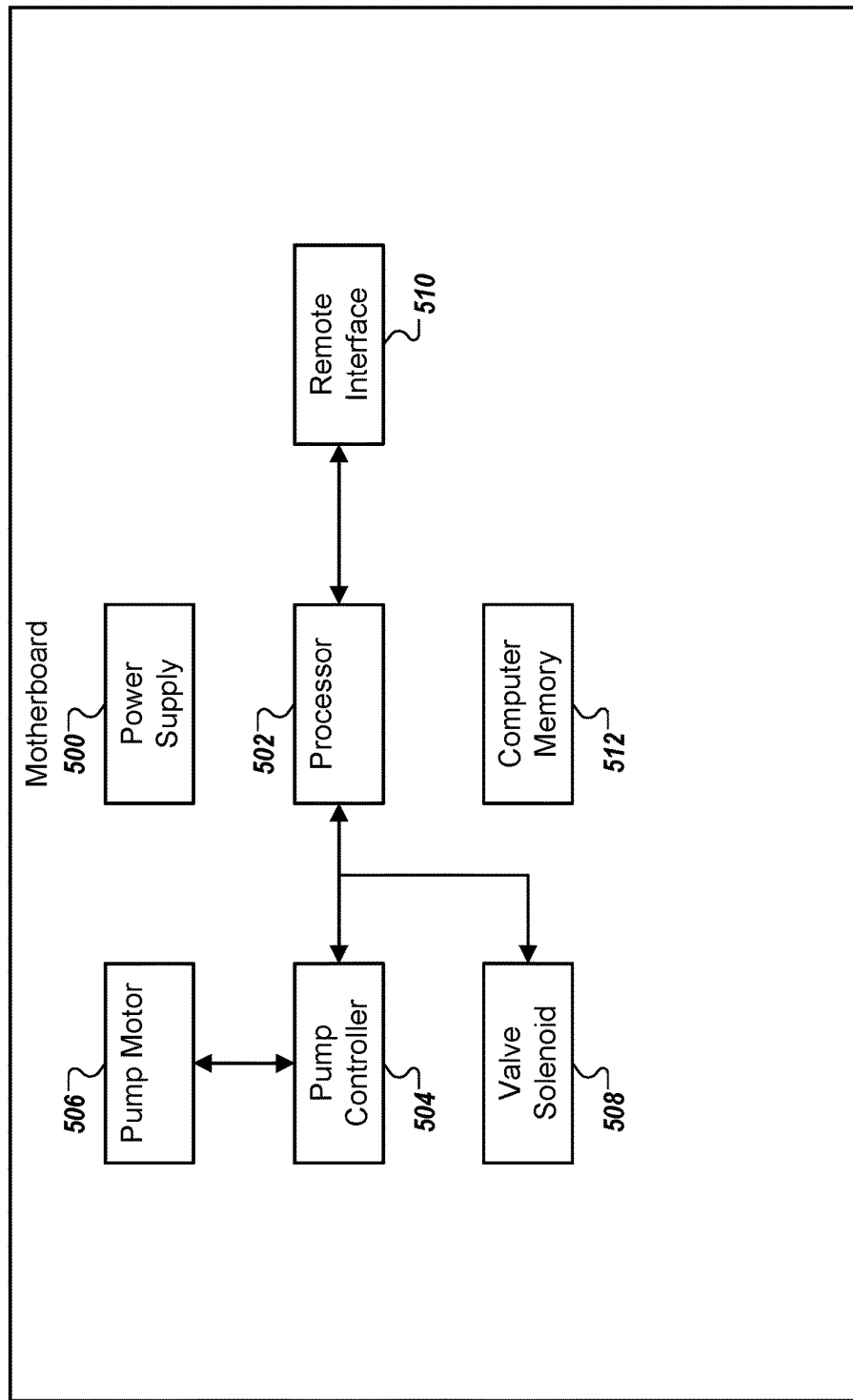
FIGS. 5 and 6 are block diagrams of examples of motherboards that can be used in a data processing system that can be associated with a bed.

FIG. 5 is a block diagram of an example of a motherboard 402 that can be used in a data processing system that can be associated with a bed system, including those described above with respect to FIGS. 1-3. In this example, compared to other examples described below, this motherboard 402 consists of relatively fewer parts and can be limited to provide a relatively limited feature set.

The motherboard includes a power supply 500, a processor 502, and computer memory 512. In general, the power supply includes hardware used to receive electrical power from an outside source and supply it to components of the motherboard 402. The power supply can include, for example, a battery pack and/or wall outlet adapter, an AC to DC converter, a DC to AC converter, a power conditioner, a capacitor bank, and/or one or more interfaces for providing power in the current type, voltage, etc., needed by other components of the motherboard 402.

The processor 502 is generally a device for receiving input, performing logical determinations, and providing output. The processor 502 can be a central processing unit, a microprocessor, general purpose logic circuitry, application-specific integrated circuitry, a combination of these, and/or other hardware for performing the functionality needed.

The memory 512 is generally one or more devices for storing data. The memory 512 can include long term stable data storage (e.g., on a hard disk), short term unstable (e.g., on Random Access Memory) or any other technologically appropriate configuration.

The motherboard 402 includes a pump controller 504 and a pump motor 506. The pump controller 504 can receive commands from the processor 502 and, in response, control the function of the pump motor 506. For example, the pump controller 504 can receive, from the processor 502, a command to increase the pressure of an air chamber by 0.3 pounds per square inch (PSI). The pump controller 504, in response, engages a valve so that the pump motor 506 is configured to pump air into the selected air chamber, and can engage the pump motor 506 for a length of time that corresponds to 0.3 PSI or until a sensor indicates that pressure has been increased by 0.3 PSI. In an alternative configuration, the message can specify that the chamber should be inflated to a target PSI, and the pump controller 504 can engage the pump motor 506 until the target PSI is reached.

A valve solenoid 508 can control which air chamber a pump is connected to. In some cases, the solenoid 508 can be controlled by the processor 502 directly. In some cases, the solenoid 508 can be controlled by the pump controller 504.

A remote interface 510 of the motherboard 402 can allow the motherboard 402 to communicate with other components of a data processing system. For example, the motherboard 402 can be able to communicate with one or more daughterboards, with peripheral sensors, and/or with peripheral controllers through the remote interface 510. The remote interface 510 can provide any technologically appropriate communication interface, including but not limited to multiple communication interfaces such as WiFi, Bluetooth, and copper wired networks.

Figure 6:
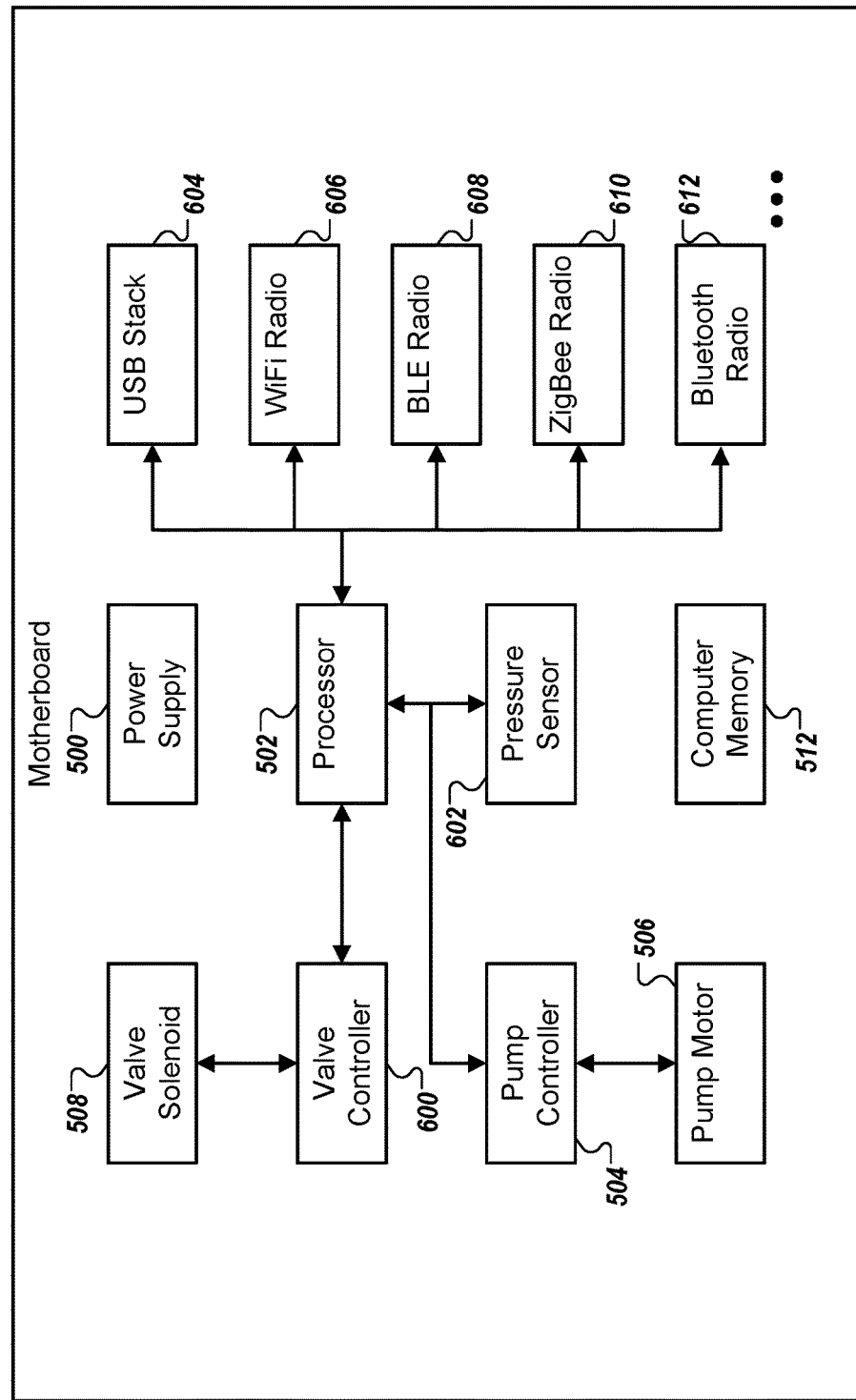

FIG. 6 is a block diagram of an example of a motherboard 402 that can be used in a data processing system that can be associated with a bed system, including those described above with respect to FIGS. 1-3. Compared to the motherboard 402 described with reference to FIG. 5, the motherboard in FIG. 6 can contain more components and provide more functionality in some applications.

In addition to the power supply 500, processor 502, pump controller 504, pump motor 506, and valve solenoid 508, this motherboard 402 is shown with a valve controller 600, a pressure sensor 602, a universal serial bus (USB) stack 604, a WiFi radio 606, a Bluetooth Low Energy (BLE) radio 608, a ZigBee radio 610, a Bluetooth radio 612 and a computer memory 512.

Similar to the way that the pump controller 504 converts commands from the processor 502 into control signals for the pump motor 506, the valve controller 600 can convert commands from the processor 502 into control signals for the valve solenoid 508. In one example, the processor 502 can issue a command to the valve controller 600 to connect the pump to a particular air chamber out of the group of air chambers in an air bed. The valve controller 600 can control the position of the valve solenoid 508 so that the pump is connected to the indicated air chamber.

The pressure sensor 602 can read pressure readings from one or more air chambers of the air bed. The pressure sensor 602 can also preform digital sensor conditioning.

The motherboard 402 can include a suite of network interfaces, including but not limited to those shown here. These network interfaces can allow the motherboard to communicate over a wired or wireless network with any number of devices, including but not limited to peripheral sensors, peripheral controllers, computing devices, and devices and services connected to the Internet 412.

Figure 7:
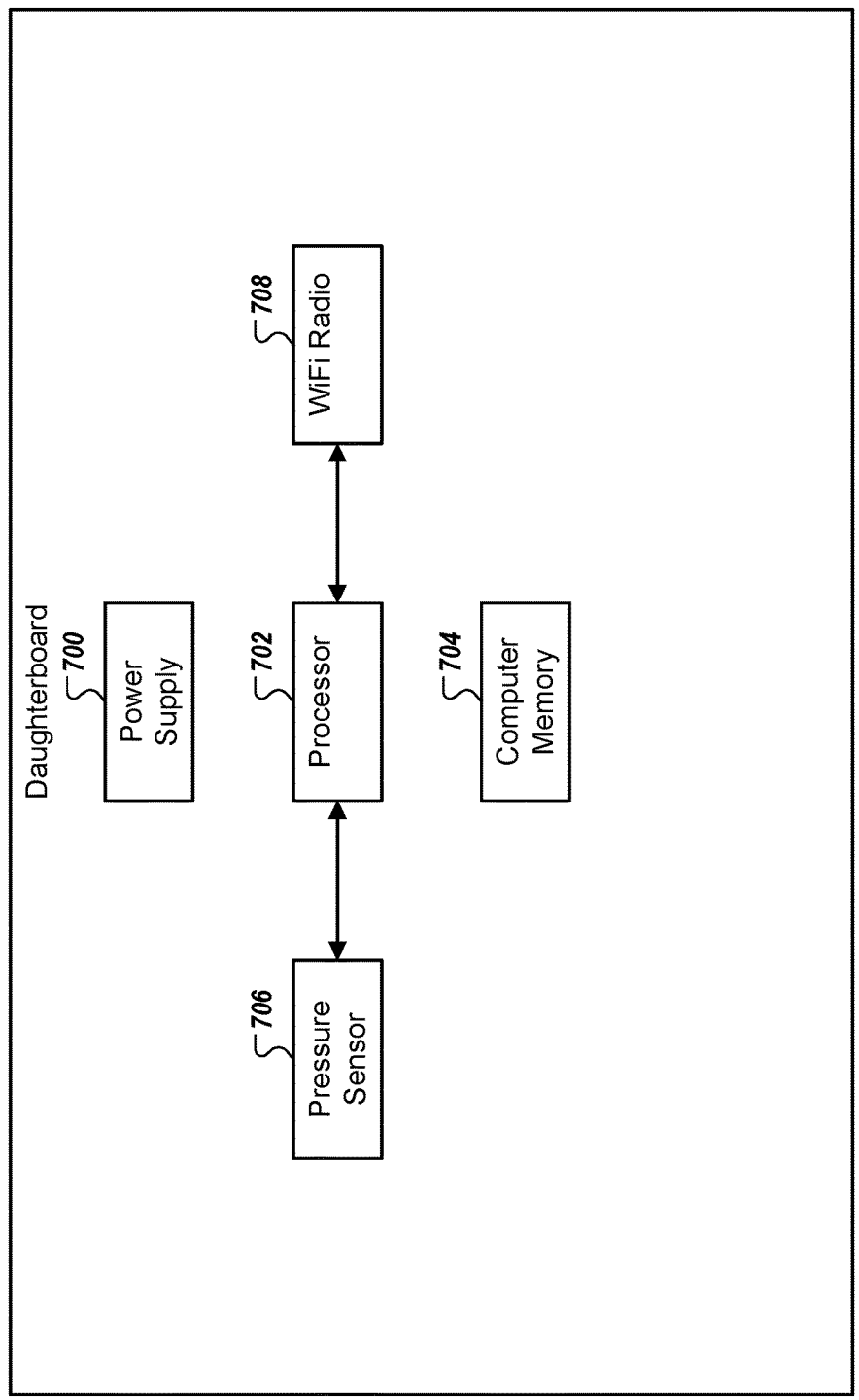
FIG. 7 is a block diagram of an example of a daughterboard that can be used in a data processing system that can be associated with a bed.

FIG. 7 is a block diagram of an example of a daughterboard 404 that can be used in a data processing system that can be associated with a bed system, including those described above with respect to FIGS. 1-3. In some configurations, one or more daughterboards 404 can be connected to the motherboard 402. Some daughterboards 404 can be designed to offload particular and/or compartmentalized tasks from the motherboard 402. This can be advantageous, for example, if the particular tasks are computationally intensive, proprietary, or subject to future revisions. For example, the daughterboard 404 can be used to calculate a particular sleep data metric. This metric can be computationally intensive, and calculating the sleep metric on the daughterboard 404 can free up the resources of the motherboard 402 while the metric is being calculated. Additionally and/or alternatively, the sleep metric can be subject to future revisions. To update the system 400 with the new sleep metric, it is possible that only the daughterboard 404 that calculates that metric need be replaced. In this case, the same motherboard 402 and other components can be used, saving the need to perform unit testing of additional components instead of just the daughterboard 404.

The daughterboard 404 is shown with a power supply 700, a processor 702, computer readable memory 704, a pressure sensor 706, and a WiFi radio 708. The processor can use the pressure sensor 706 to gather information about the pressure of the air chamber or chambers of an air bed. From this data, the processor 702 can perform an algorithm to calculate a sleep metric. In some examples, the sleep metric can be calculated from only the pressure of air chambers. In other examples, the sleep metric can be calculated from one or more other sensors. In an example in which different data is needed, the processor 702 can receive that data from an appropriate sensor or sensors. These sensors can be internal to the daughterboard 404, accessible via the WiFi radio 708, or otherwise in communication with the processor 702. Once the sleep metric is calculated, the processor 702 can report that sleep metric to, for example, the motherboard 402.

Figure 8:
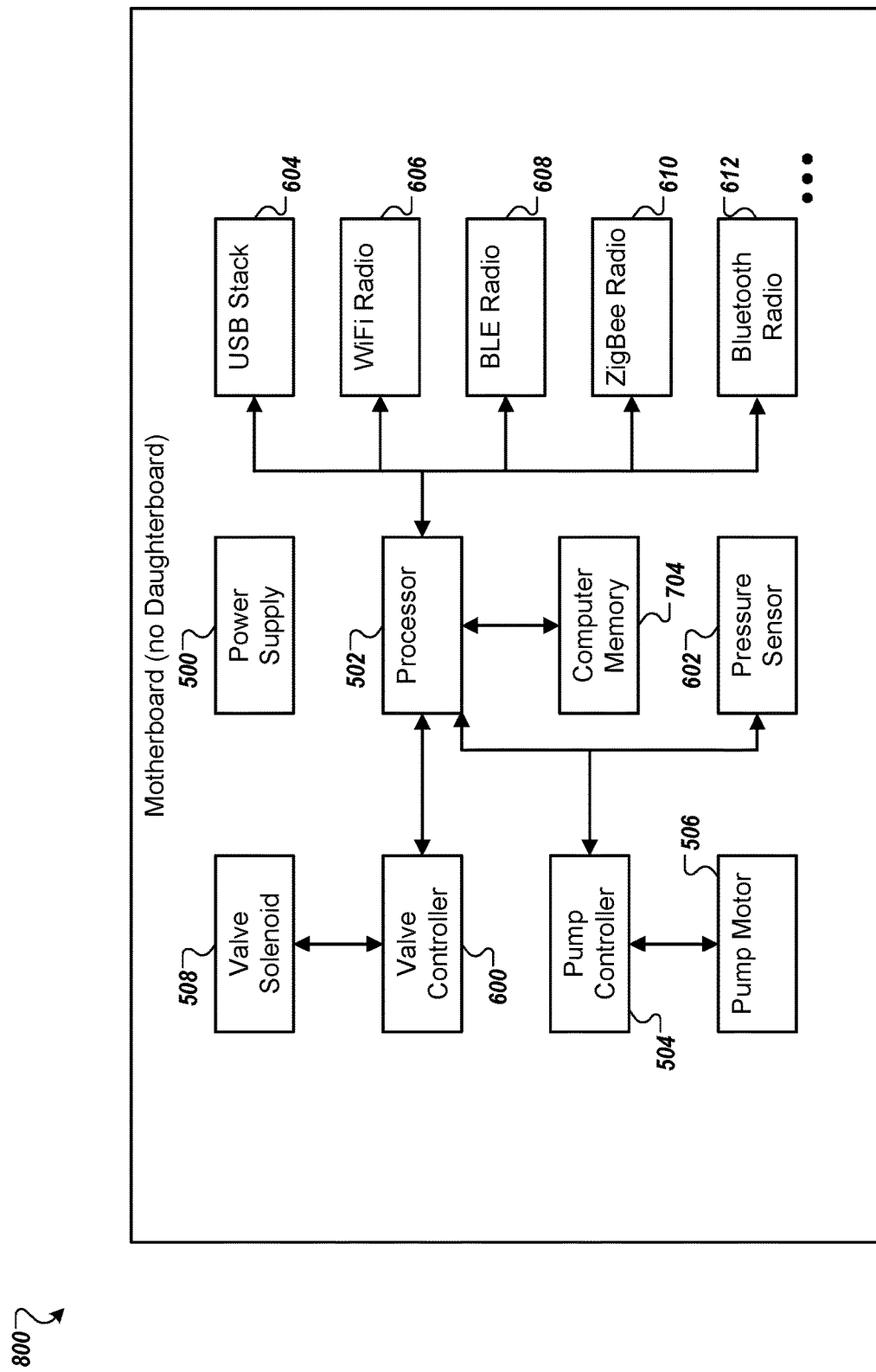
FIG. 8 is a block diagram of an example of a motherboard with no daughterboard that can be used in a data processing system that can be associated with a bed.

FIG. 8 is a block diagram of an example of a motherboard 800 with no daughterboard that can be used in a data processing system that can be associated with a bed system, including those described above with respect to FIGS. 1-3. In this example, the motherboard 800 can perform most, all, or more of the features described with reference to the motherboard 402 in FIG. 6 and the daughterboard 404 in FIG. 7.

Figure 9:
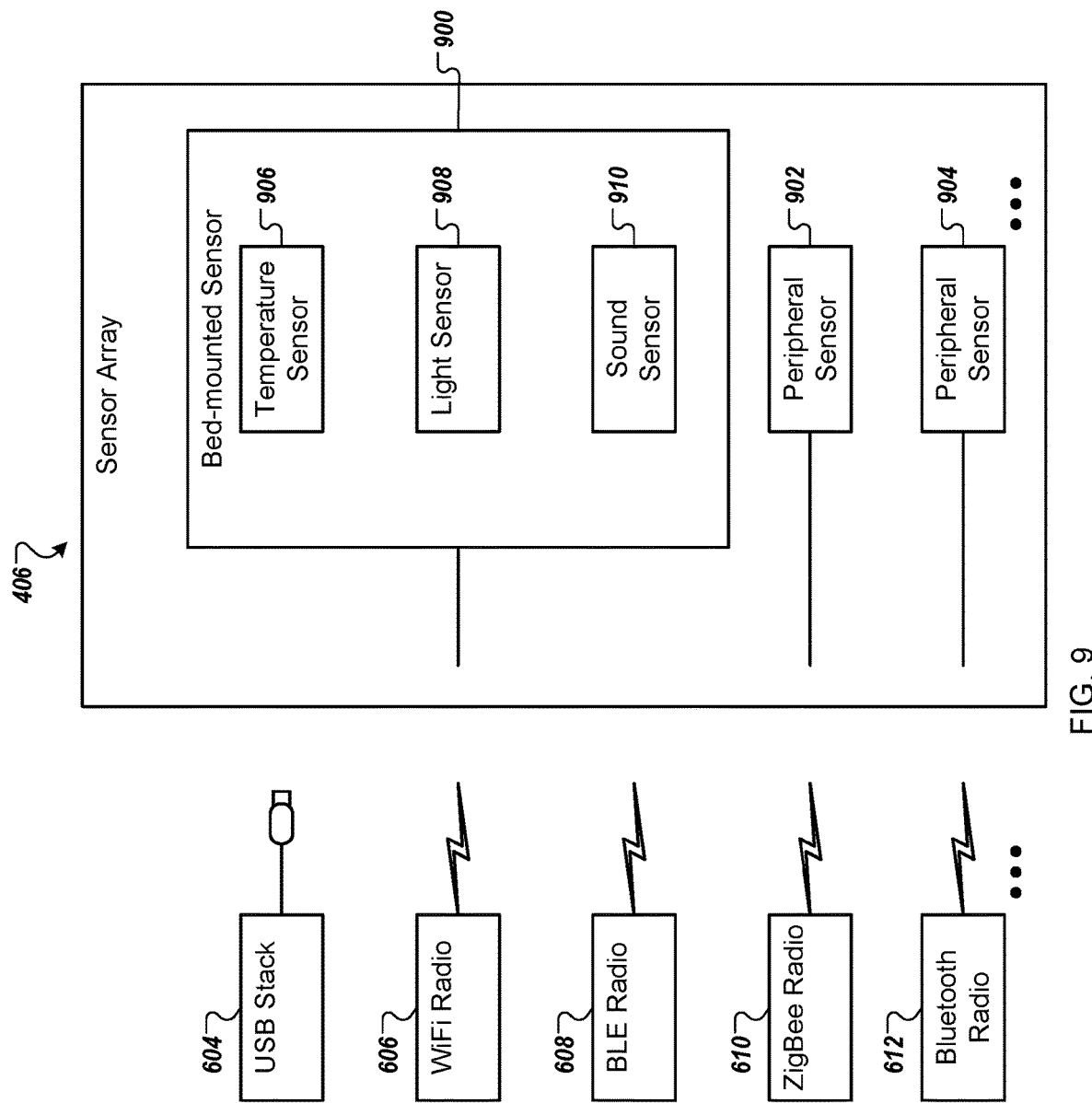
FIG. 9 is a block diagram of an example of a sensory array that can be used in a data processing system that can be associated with a bed.

FIG. 9 is a block diagram of an example of a sensory array 406 that can be used in a data processing system that can be associated with a bed system, including those described above with respect to FIGS. 1-3. In general, the sensor array 406 is a conceptual grouping of some or all the peripheral sensors that communicate with the motherboard 402 but are not native to the motherboard 402.

The peripheral sensors of the sensor array 406 can communicate with the motherboard 402 through one or more of the network interfaces of the motherboard, including but not limited to the USB stack 604, a WiFi radio 606, a Bluetooth Low Energy (BLE) radio 608, a ZigBee radio 610, and a Bluetooth radio 612, as is appropriate for the configuration of the particular sensor. For example, a sensor that outputs a reading over a USB cable can communicate through the USB stack 604.

Some of the peripheral sensors 900 of the sensor array 406 can be bed mounted 900. These sensors can be, for example, embedded into the structure of a bed and sold with the bed, or later affixed to the structure of the bed. Other peripheral sensors 902 and 904 can be in communication with the motherboard 402, but optionally not mounted to the bed. In some cases, some or all of the bed mounted sensors 900 and/or peripheral sensors 902 and 904 can share networking hardware, including a conduit that contains wires from each sensor, a multi-wire cable or plug that, when affixed to the motherboard 402, connect all of the associated sensors with the motherboard 402. In some embodiments, one, some, or all of sensors 902, 904, 906, 908, and 910 can sense one or more features of a mattress, such as pressure, temperature, light, sound, and/or one or more other features of the mattress. In some embodiments, one, some, or all of sensors 902, 904, 906, 908, and 910 can sense one or more features external to the mattress. In some embodiments, pressure sensor 902 can sense pressure of the mattress while some or all of sensors 902, 904, 906, 908, and 910 can sense one or more features of the mattress and/or external to the mattress.

Figure 10:
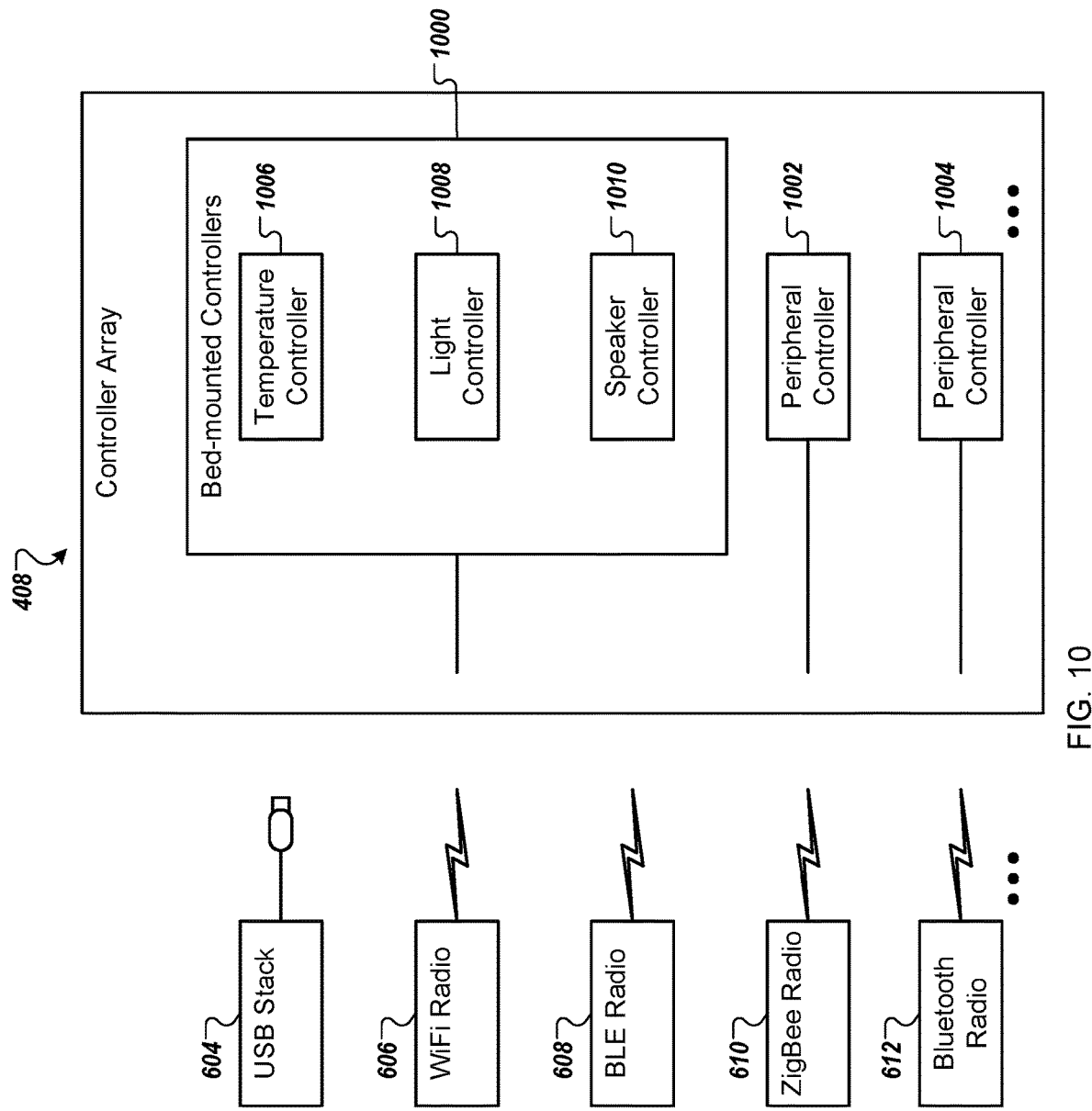
FIG. 10 is a block diagram of an example of a control array that can be used in a data processing system that can be associated with a bed

FIG. 10 is a block diagram of an example of a controller array 408 that can be used in a data processing system that can be associated with a bed system, including those described above with respect to FIGS. 1-3. In general, the controller array 408 is a conceptual grouping of some or all peripheral controllers that communicate with the motherboard 402 but are not native to the motherboard 402.

The peripheral controllers of the controller array 408 can communicate with the motherboard 402 through one or more of the network interfaces of the motherboard, including but not limited to the USB stack 604, a WiFi radio 606, a Bluetooth Low Energy (BLE) radio 608, a ZigBee radio 610, and a Bluetooth radio 612, as is appropriate for the configuration of the particular sensor. For example, a controller that receives a command over a USB cable can communicate through the USB stack 604.

Some of the controllers of the controller array 408 can be bed mounted 1000. These controllers can be, for example, embedded into the structure of a bed and sold with the bed, or later affixed to the structure of the bed. Other peripheral controllers 1002 and 1004 can be in communication with the motherboard 402, but optionally not mounted to the bed. In some cases, some or all of the bed mounted controllers 1000 and/or peripheral controllers 1002 and 1004 can share networking hardware, including a conduit that contains wires for each controller, a multi-wire cable or plug that, when affixed to the motherboard 402, connects all of the associated controllers with the motherboard 402.

Figure 11:
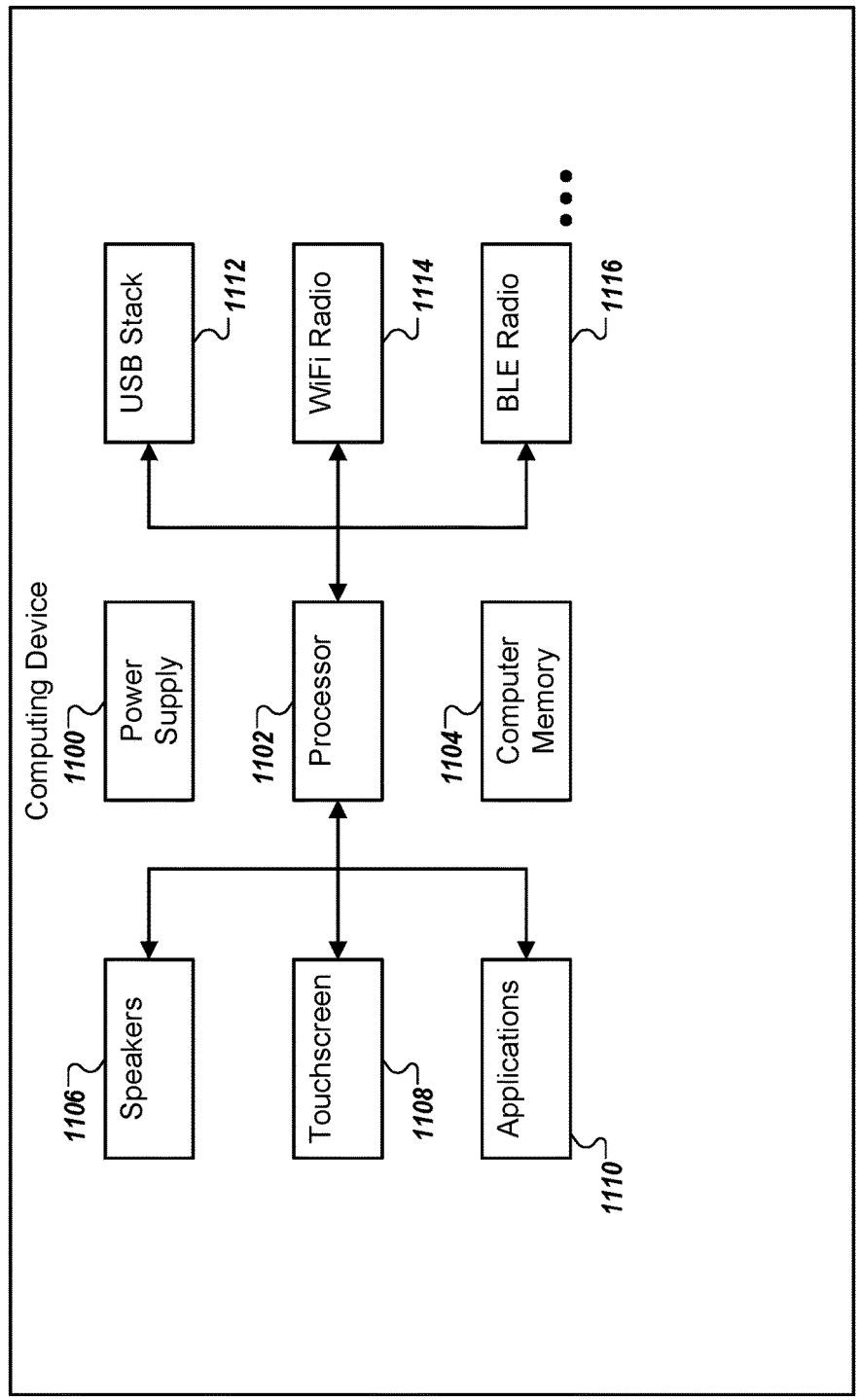
FIG. 11 is a block diagram of an example of a computing device that can be used in a data processing system that can be associated with a bed.

FIG. 11 is a block diagram of an example of a computing device 412 that can be used in a data processing system that can be associated with a bed system, including those described above with respect to FIGS. 1-3. The computing device 412 can include, for example, computing devices used by a user of a bed. Example computing devices 412 include, but are not limited to, mobile computing devices (e.g., mobile phones, tablet computers, laptops) and desktop computers.

The computing device 412 includes a power supply 1100, a processor 1102, and computer readable memory 1104. User input and output can be transmitted by, for example, speakers 1106, a touchscreen 1108, or other not shown components such as a pointing device or keyboard. The computing device 412 can run one or more applications 1110. These applications can include, for example, application to allow the user to interact with the system 400. These applications can allow a user to view information about the bed (e.g., sensor readings, sleep metrics), or configure the behavior of the system 400 (e.g., set a desired firmness to the bed, set desired behavior for peripheral devices). In some cases, the computing device 412 can be used in addition to, or to replace, the remote control 122 described previously.

Figure 12:
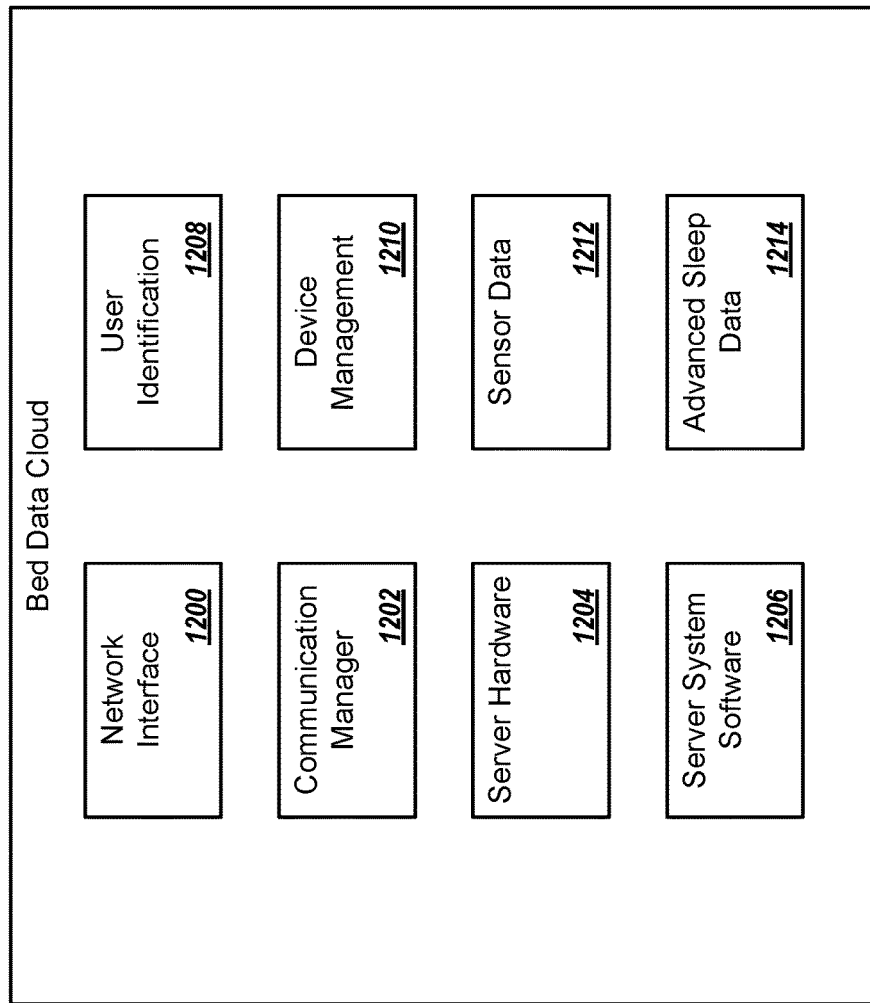
FIGS. 12-16 are block diagrams of example cloud services that can be used in a data processing system that can be associated with a bed.

FIG. 12 is a block diagram of an example bed data cloud service 410*a* that can be used in a data processing system that can be associated with a bed system, including those described above with respect to FIGS. 1-3. In this example, the bed data cloud service 410*a* is configured to collect sensor data and sleep data from a particular bed, and to match the sensor and sleep data with one or more users that use the bed when the sensor and sleep data was generated.

The bed data cloud service 410*a* is shown with a network interface 1200, a communication manager 1202, server hardware 1204, and server system software 1206. In addition, the bed data cloud service 410*a* is shown with a user identification module 1208, a device management 1210 module, a sensor data module 1210, and an advanced sleep data module 1214.

The network interface 1200 generally includes hardware and low level software used to allow one or more hardware devices to communicate over networks. For example the network interface 1200 can include network cards, routers, modems, and other hardware needed to allow the components of the bed data cloud service 410*a* to communicate with each other and other destinations over, for example, the Internet 412. The communication manger 1202 generally comprises hardware and software that operate above the network interface 1200. This includes software to initiate, maintain, and tear down network communications used by the bed data cloud service 410*a*. This includes, for example, TCP/IP, SSL or TLS, Torrent, and other communication sessions over local or wide area networks. The communication manger 1202 can also provide load balancing and other services to other elements of the bed data cloud service 410*a*.

The server hardware 1204 generally includes the physical processing devices used to instantiate and maintain bed data cloud service 410*a*. This hardware includes, but is not limited to processors (e.g., central processing units, ASICs, graphical processers), and computer readable memory (e.g., random access memory, stable hard disks, tape backup). One or more servers can be configured into clusters, multi-computer, or datacenters that can be geographically separate or connected.

The server system software 1206 generally includes software that runs on the server hardware 1204 to provide operating environments to applications and services. The server system software 1206 can include operating systems running on real servers, virtual machines instantiated on real servers to create many virtual servers, server level operations such as data migration, redundancy, and backup.

The user identification 1208 can include, or reference, data related to users of beds with associated data processing systems. For example, the users can include customers, owners, or other users registered with the bed data cloud service 410*a* or another service. Each user can have, for example, a unique identifier, user credentials, contact information, billing information, demographic information, or any other technologically appropriate information.

The device manager 1210 can include, or reference, data related to beds or other products associated with data processing systems. For example, the beds can include products sold or registered with a system associated with the bed data cloud service 410*a*. Each bed can have, for example, a unique identifier, model and/or serial number, sales information, geographic information, delivery information, a listing of associated sensors and control peripherals, etc. Additionally, an index or indexes stored by the bed data cloud service 410*a* can identify users that are associated with beds. For example, this index can record sales of a bed to a user, users that sleep in a bed, etc.

The sensor data 1212 can record raw or condensed sensor data recorded by beds with associated data processing systems. For example, a bed's data processing system can have a temperature sensor, pressure sensor, and light sensor. Readings from these sensors, either in raw form or in a format generated from the raw data (e.g. sleep metrics) of the sensors, can be communicated by the bed's data processing system to the bed data cloud service 410*a* for storage in the sensor data 1212. Additionally, an index or indexes stored by the bed data cloud service 410*a* can identify users and/or beds that are associated with the sensor data 1212.

The bed data cloud service 410*a* can use any of its available data to generate advanced sleep data 1214. In general, the advanced sleep data 1214 includes sleep metrics and other data generated from sensor readings. Some of these calculations can be performed in the bed data cloud service 410*a* instead of locally on the bed's data processing system, for example, because the calculations are computationally complex or require a large amount of memory space or processor power that is not available on the bed's data processing system. This can help allow a bed system to operate with a relatively simple controller and still be part of a system that performs relatively complex tasks and computations.

Figure 13:
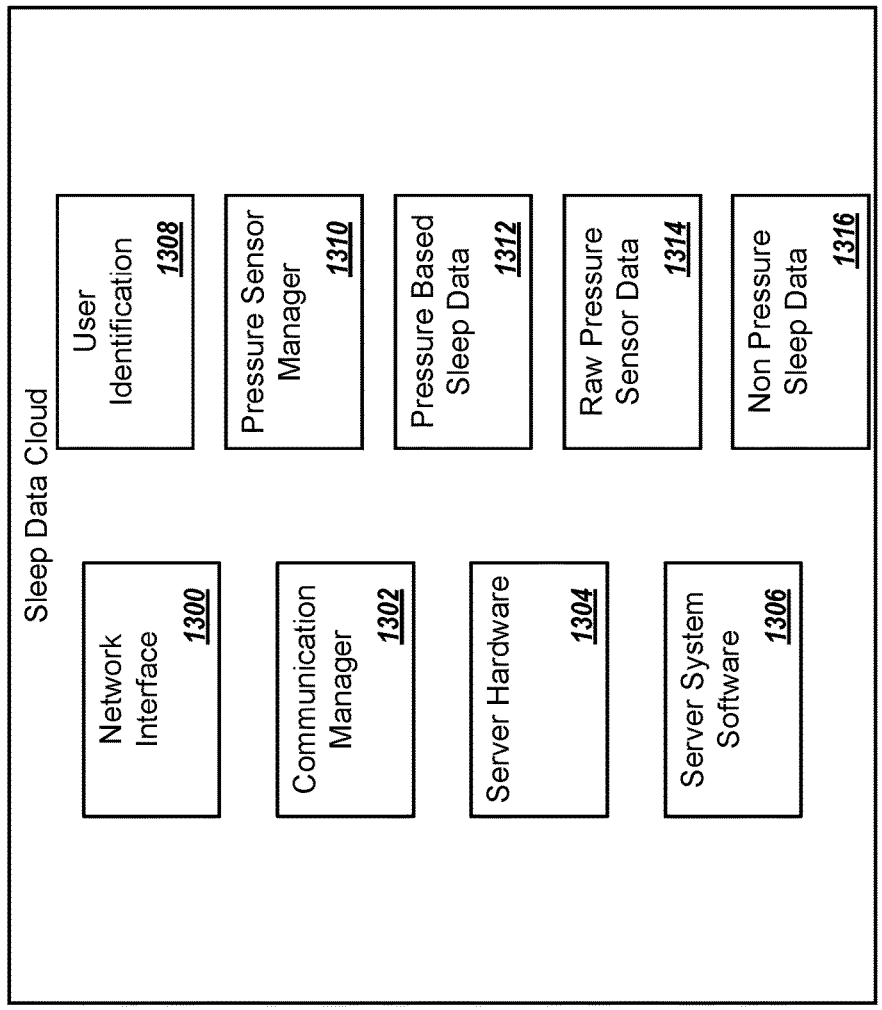

FIG. 13 is a block diagram of an example sleep data cloud service 410*b* that can be used in a data processing system that can be associated with a bed system, including those described above with respect to FIGS. 1-3. In this example, the sleep data cloud service 410*b* is configured to record data related to users' sleep experience.

The sleep data cloud service 410*b* is shown with a network interface 1300, a communication manager 1302, server hardware 1304, and server system software 1306. In addition, the sleep data cloud service 410*b* is shown with a user identification module 1308, a pressure sensor manager 1310, a pressure based sleep data module 1312, a raw pressure sensor data module 1314, and a non-pressure sleep data module 1316.

The pressure sensor manager 1310 can include, or reference, data related to the configuration and operation of pressure sensors in beds. For example, this data can include an identifier of the types of sensors in a particular bed, their settings and calibration data, etc.

The pressure based sleep data 1312 can use raw pressure sensor data 1314 to calculate sleep metrics specifically tied to pressure sensor data. For example, user presence, movements, weight change, heart rate, and breathing rate can all be determined from raw pressure sensor data 1314. Additionally, an index or indexes stored by the sleep data cloud service 410*b* can identify users that are associated with pressure sensors, raw pressure sensor data, and/or pressure based sleep data.

The non-pressure sleep data 1316 can use other sources of data to calculate sleep metrics. For example, user entered preferences, light sensor readings, and sound sensor readings can all be used to track sleep data. Additionally, an index or indexes stored by the sleep data cloud service 410*b* can identify users that are associated with other sensors and/or non-pressure sleep data 1316.

Figure 14:
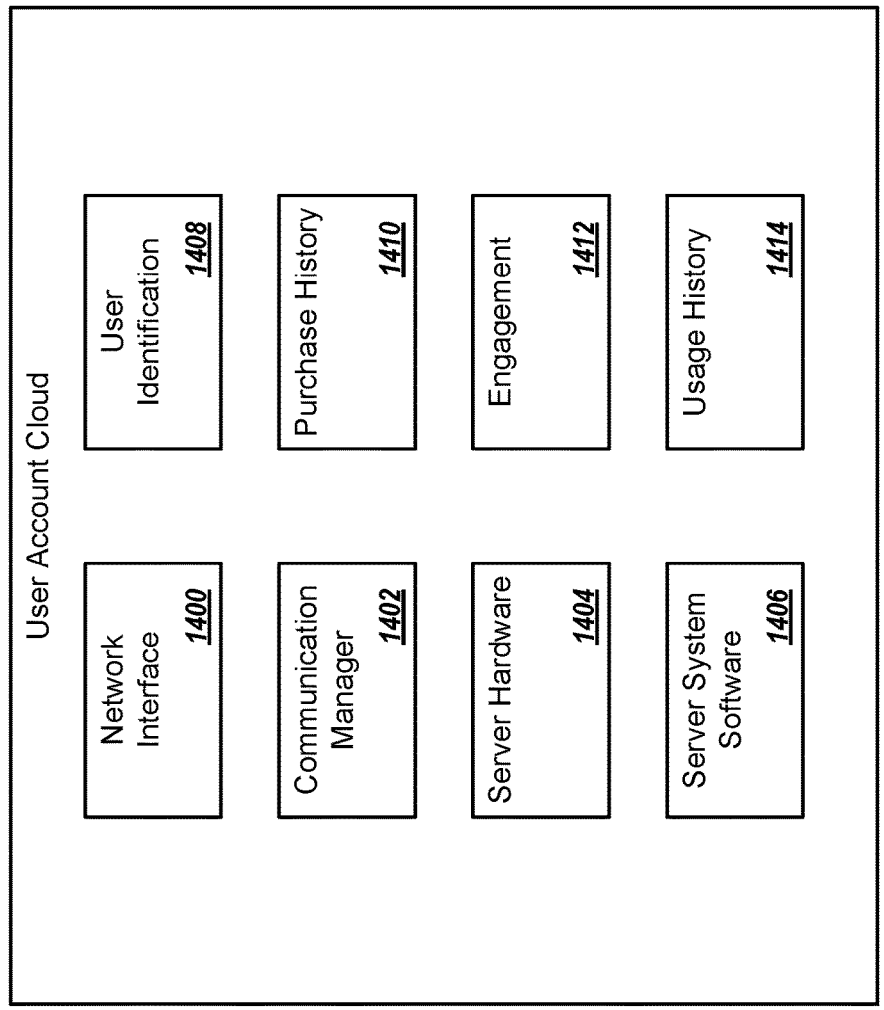

FIG. 14 is a block diagram of an example user account cloud service 410*c* that can be used in a data processing system that can be associated with a bed system, including those described above with respect to FIGS. 1-3. In this example, the user account cloud service 410*c* is configured to record a list of users and to identify other data related to those users.

The user account cloud service 410*c* is shown with a network interface 1400, a communication manager 1402, server hardware 1404, and server system software 1406. In addition, the user account cloud service 410*c* is shown with a user identification module 1408, a purchase history module 1410, an engagement module 1412, and an application usage history module 1414.

The user identification module 1408 can include, or reference, data related to users of beds with associated data processing systems. For example, the users can include customers, owners, or other users registered with the user account cloud service 410*a* or another service. Each user can have, for example, a unique identifier, and user credentials, demographic information, or any other technologically appropriate information.

The purchase history module 1410 can include, or reference, data related to purchases by users. For example, the purchase data can include a sale's contact information, billing information, and salesperson information. Additionally, an index or indexes stored by the user account cloud service 410c can identify users that are associated with a purchase.

The engagement 1412 can track user interactions with the manufacturer, vendor, and/or manager of the bed and or cloud services. This engagement data can include communications (e.g., emails, service calls), data from sales (e.g., sales receipts, configuration logs), and social network interactions.

The usage history module 1414 can contain data about user interactions with one or more applications and/or remote controls of a bed. For example, a monitoring and configuration application can be distributed to run on, for example, computing devices 412. This application can log and report user interactions for storage in the application usage history module 1414. Additionally, an index or indexes stored by the user account cloud service 410c can identify users that are associated with each log entry.

Figure 15:
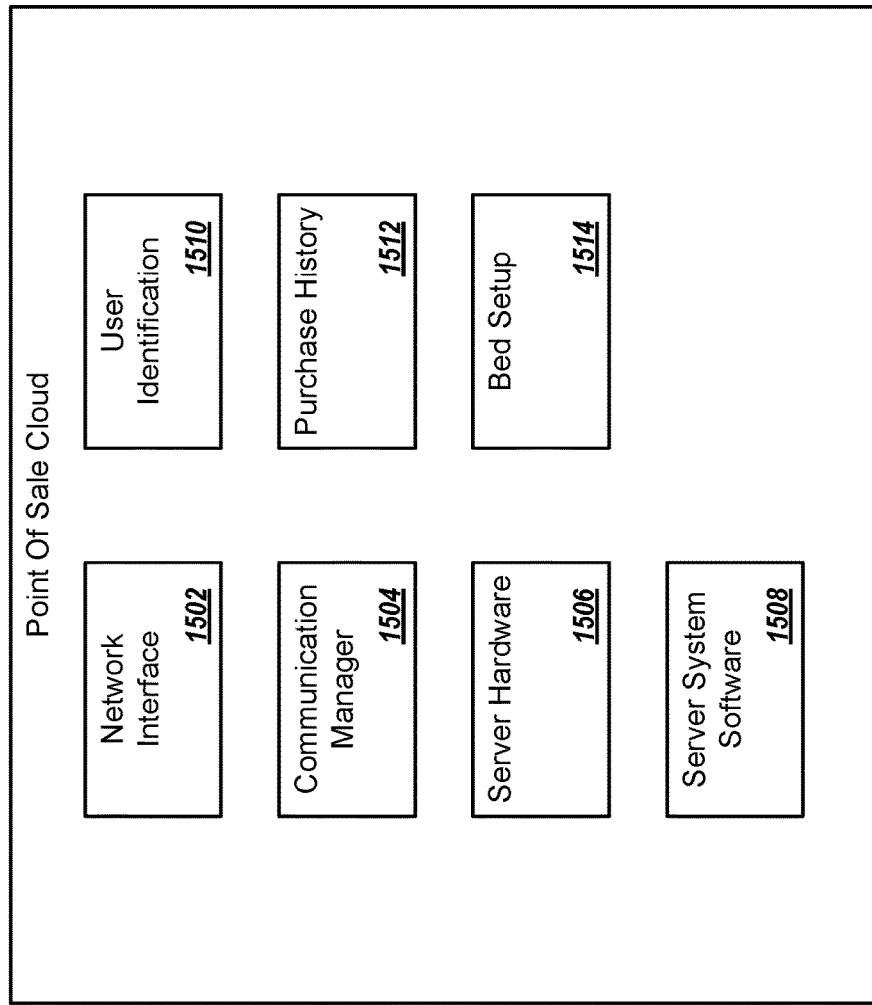

FIG. 15 is a block diagram of an example point of sale cloud service 1500 that can be used in a data processing system that can be associated with a bed system, including those described above with respect to FIGS. 1-3. In this example, the point of sale cloud service 1500 is configured to record data related to users' purchases.

The point of sale cloud service 1500 is shown with a network interface 1502, a communication manager 1504, server hardware 1506, and server system software 1508. In addition, the point of sale cloud service 1500 is shown with a user identification module 1510, a purchase history module 1512, and a setup module 1514.

The purchase history module 1512 can include, or reference, data related to purchases made by users identified in the user identification module 1510. The purchase information can include, for example, data of a sale, price, and location of sale, delivery address, and configuration options selected by the users at the time of sale. These configuration options can include selections made by the user about how they wish their newly purchased beds to be setup and can include, for example, expected sleep schedule, a listing of peripheral sensors and controllers that they have or will install, etc.

The bed setup module 1514 can include, or reference, data related to installations of beds that users' purchase. The bed setup data can include, for example, the date and address to which a bed is delivered, the person that accepts delivery, the configuration that is applied to the bed upon delivery, the name or names of the person or people who will sleep on the bed, which side of the bed each person will use, etc.

Data recorded in the point of sale cloud service 1500 can be referenced by a user's bed system at later dates to control functionality of the bed system and/or to send control signals to peripheral components according to data recorded in the point of sale cloud service 1500. This can allow a salesperson to collect information from the user at the point of sale that later facilitates automation of the bed system. In some examples, some or all aspects of the bed system can be automated with little or no user-entered data required after the point of sale. In other examples, data recorded in the point of sale cloud service 1500 can be used in connection with a variety of additional data gathered from user-entered data.

Figure 16:
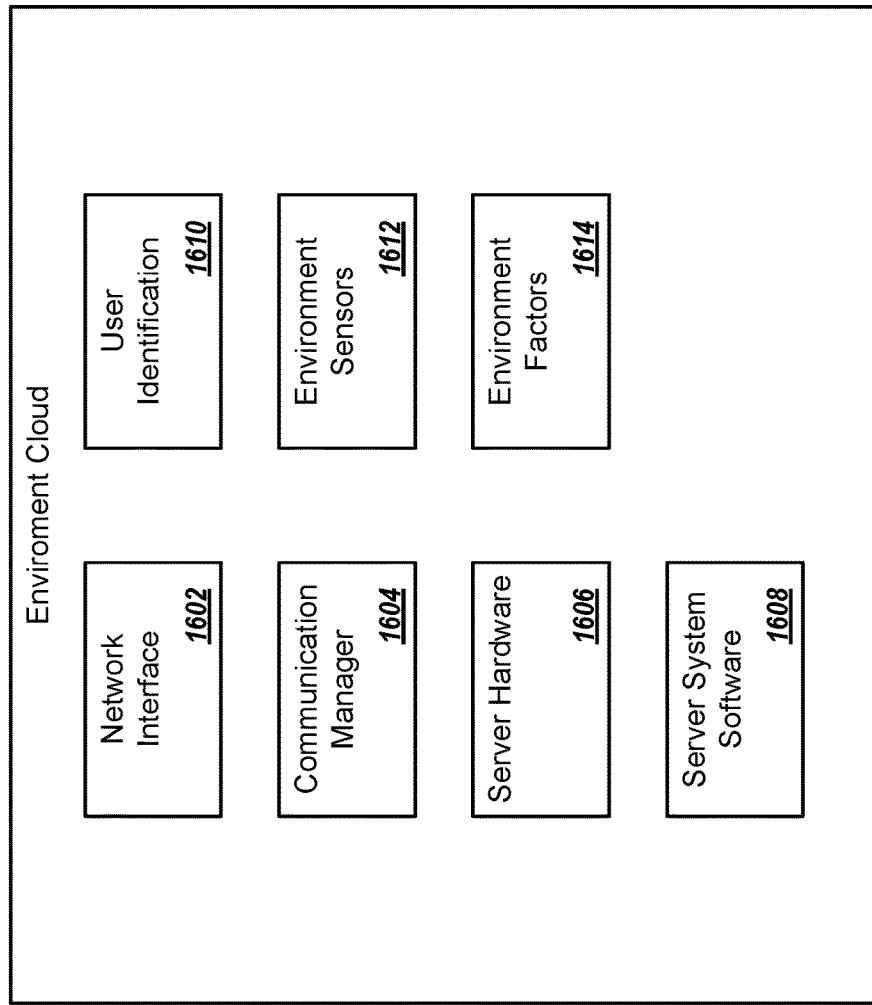

FIG. 16 is a block diagram of an example environment cloud service 1600 that can be used in a data processing system that can be associated with a bed system, including those described above with respect to FIGS. 1-3. In this example, the environment cloud service 1600 is configured to record data related to users' home environment.

The environment cloud service 1600 is shown with a network interface 1602, a communication manager 1604, server hardware 1606, and server system software 1608. In addition, the environment cloud service 1600 is shown with a user identification module 1610, an environmental sensor module 1612, and an environmental factors module 1614.

The environmental sensors module 1612 can include a listing of sensors that users' in the user identification module 1610 have installed in their bed. These sensors include any sensors that can detect environmental variables—light sensors, noise sensors, vibration sensors, thermostats, etc. Additionally, the environmental sensors module 1612 can store historical readings or reports from those sensors.

The environmental factors module 1614 can include reports generated based on data in the environmental sensors module 1612. For example, for a user with a light sensor with data in the environment sensors module 1612, the environmental factors module 1614 can hold a report indicating the frequency and duration of instances of increased lighting when the user is asleep.

In the examples discussed here, each cloud service 410 is shown with some of the same components. In various configurations, these same components can be partially or wholly shared between services, or they can be separate. In some configurations, each service can have separate copies of some or all of the components that are the same or different in some ways. Additionally, these components are only supplied as illustrative examples. In other examples each cloud service can have different number, types, and styles of components that are technically possible.

Figure 17:
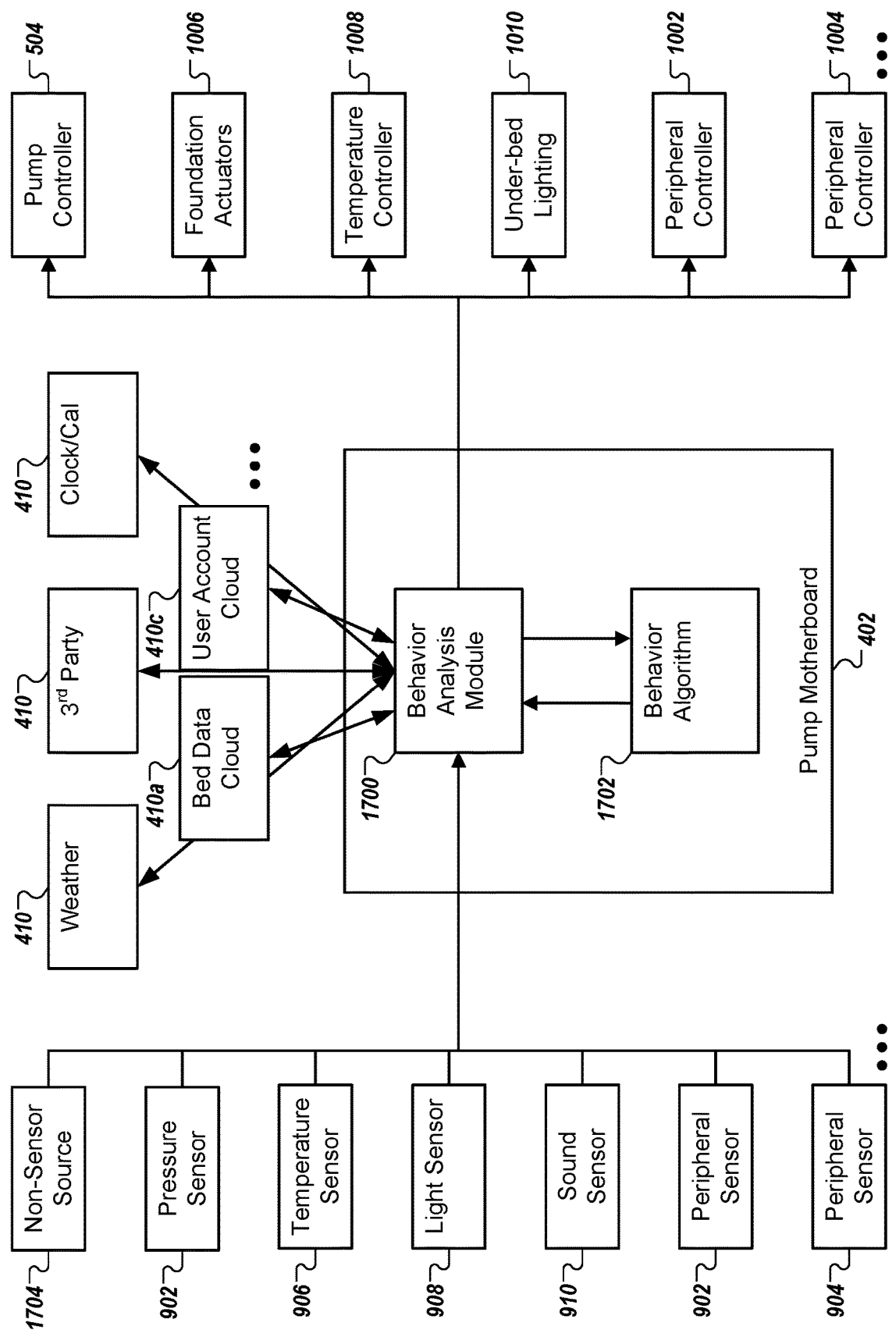
FIG. 17 is a block diagram of an example of using a data processing system that can be associated with a bed to automate peripherals around the bed.

FIG. 17 is a block diagram of an example of using a data processing system that can be associated with a bed (such as a bed of the bed systems described herein) to automate peripherals around the bed. Shown here is a behavior analysis module 1700 that runs on the pump motherboard 402. For example, the behavior analysis module 1700 can be one or more software components stored on the computer memory 512 and executed by the processor 502. In general, the behavior analysis module 1700 can collect data from a wide variety of sources (e.g., sensors, non-sensor local sources, cloud data services) and use a behavioral algorithm 1702 to generate one or more actions to be taken (e.g., commands to send to peripheral controllers, data to send to cloud services). This can be useful, for example, in tracking user behavior and automating devices in communication with the user's bed.

The behavior analysis module 1700 can collect data from any technologically appropriate source, for example, to gather data about features of a bed, the bed's environment, and/or the bed's users. Some such sources include any of the sensors of the sensor array 406. For example, this data can provide the behavior analysis module 1700 with information about the current state of the environment around the bed. For example, the behavior analysis module 1700 can access readings from the pressure sensor 902 to determine the pressure of an air chamber in the bed. From this reading, and potentially other data, user presence in the bed can be determined. In another example, the behavior analysis module can access a light sensor 908 to detect the amount of light in the bed's environment.

Similarly, the behavior analysis module 1700 can access data from cloud services. For example, the behavior analysis module 1700 can access the bed cloud service 410a to access historical sensor data 1212 and/or advanced sleep data 1214. Other cloud services 410, including those not previously described can be accessed by the behavior analysis module 1700. For example, the behavior analysis module 1700 can access a weather reporting service, a 3$^{rd}$ party data provider (e.g., traffic and news data, emergency broadcast data, user travel data), and/or a clock and calendar service.

Similarly, the behavior analysis module 1700 can access data from non-sensor sources 1704. For example, the behavior analysis module 1700 can access a local clock and calendar service (e.g., a component of the motherboard 402 or of the processor 502).

The behavior analysis module 1700 can aggregate and prepare this data for use by one or more behavioral algorithms 1702. The behavioral algorithms 1702 can be used to learn a user's behavior and/or to perform some action based on the state of the accessed data and/or the predicted user behavior. For example, the behavior algorithm 1702 can use available data (e.g., pressure sensor, non-sensor data, clock and calendar data) to create a model of when a user goes to bed every night. Later, the same or a different behavioral algorithm 1702 can be used to determine if an increase in air chamber pressure is likely to indicate a user going to bed and, if so, send some data to a third-party cloud service 410 and/or engage a peripheral controller 1002.

In the example shown, the behavioral analysis module 1700 and the behavioral algorithm 1702 are shown as components of the motherboard 402. However, other configurations are possible. For example, the same or a similar behavioral analysis module and/or behavior algorithm can be run in one or more cloud services, and the resulting output can be sent to the motherboard 402, a controller in the controller array 408, or to any other technologically appropriate recipient.

Figure 18:
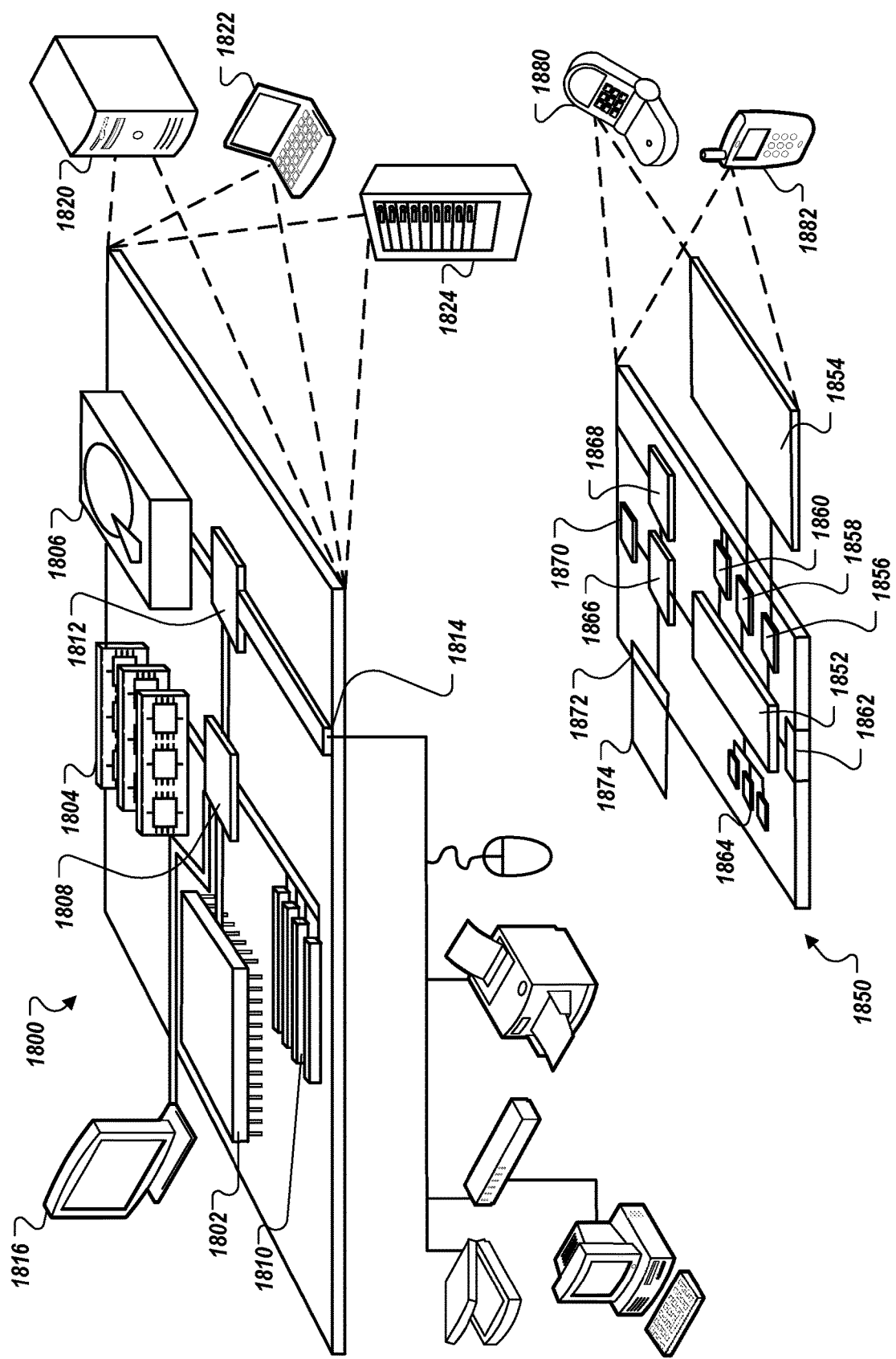
FIG. 18 is a schematic diagram that shows an example of a computing device and a mobile computing device.

FIG. 18 shows an example of a computing device 1800 and an example of a mobile computing device that can be used to implement the techniques described here. The computing device 1800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and can be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1804 stores information within the computing device 1800. In some implementations, the memory 1804 is a volatile memory unit or units. In some implementations, the memory 1804 is a non-volatile memory unit or units. The memory 1804 can also be another form of computer-readable medium, such as a magnetic or optical disk.

The storage device 1806 is capable of providing mass storage for the computing device 1800. In some implementations, the storage device 1806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1804, the storage device 1806, or memory on the processor 1802.

The high-speed interface 1808 manages bandwidth-intensive operations for the computing device 1800, while the low-speed interface 1812 manages lower bandwidth-intensive operations. Such allocation of functions is exemplary only. In some implementations, the high-speed interface 1808 is coupled to the memory 1804, the display 1816 (e.g., through a graphics processor or accelerator), and to the high-speed expansion ports 1810, which can accept various expansion cards (not shown). In the implementation, the low-speed interface 1812 is coupled to the storage device 1806 and the low-speed expansion port 1814. The low-speed expansion port 1814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1800 can be implemented in a number of different forms, as shown in the figure. For example, it can be implemented as a standard server 1820, or multiple times in a group of such servers. In addition, it can be implemented in a personal computer such as a laptop computer 1822. It can also be implemented as part of a rack server system 1824. Alternatively, components from the computing device 1800 can be combined with other components in a mobile device (not shown), such as a mobile computing device 1850. Each of such devices can contain one or more of the computing device 1800 and the mobile computing device 1850, and an entire system can be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 can also be provided with a storage device, such as a micro-drive or other device, to provide additional storage. Each of the processor 1852, the memory 1864, the display 1854, the communication interface 1866, and the transceiver 1868, are interconnected using various buses, and several of the components can be mounted on a common motherboard or in other manners as appropriate.

The processor 1852 can execute instructions within the mobile computing device 1850, including instructions stored in the memory 1864. The processor 1852 can be implemented as a chipset of chips that include separate and multiple analog and digital processors. The processor 1852 can provide, for example, for coordination of the other components of the mobile computing device 1850, such as control of user interfaces, applications run by the mobile computing device 1850, and wireless communication by the mobile computing device 1850.

The processor 1852 can communicate with a user through a control interface 1858 and a display interface 1856 coupled to the display 1854. The display 1854 can be, for example, a TFT (Thin-Film-Transistor Liquid Crystal Display) display or an OLED (Organic Light Emitting Diode) display, or other appropriate display technology. The display interface 1856 can comprise appropriate circuitry for driving the display 1854 to present graphical and other information to a user. The control interface 1858 can receive commands from a user and convert them for submission to the processor 1852. In addition, an external interface 1862 can provide communication with the processor 1852, so as to enable near area communication of the mobile computing device 1850 with other devices. The external interface 1862 can provide, for example, for wired communication in some implementations, or for wireless communication in other implementations, and multiple interfaces can also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 can also be provided and connected to the mobile computing device 1850 through an expansion interface 1872, which can include, for example, a SIMM (Single In Line Memory Module) card interface. The expansion memory 1874 can provide extra storage space for the mobile computing device 1850, or can also store applications or other information for the mobile computing device 1850. Specifically, the expansion memory 1874 can include instructions to carry out or supplement the processes described above, and can include secure information also. Thus, for example, the expansion memory 1874 can be provide as a security module for the mobile computing device 1850, and can be programmed with instructions that permit secure use of the mobile computing device 1850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1864, the expansion memory 1874, or memory on the processor 1852. In some implementations, the computer program product can be received in a propagated signal, for example, over the transceiver 1868 or the external interface 1862.

The mobile computing device 1850 can communicate wirelessly through the communication interface 1866, which can include digital signal processing circuitry where necessary. The communication interface 1866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1868 using a radio-frequency. In addition, short-range communication can occur, such as using a Bluetooth, WiFi, or other such transceiver (not shown). In addition, a GPS (Global Positioning System) receiver module 1870 can provide additional navigation- and location-related wireless data to the mobile computing device 1850, which can be used as appropriate by applications running on the mobile computing device 1850.

The mobile computing device 1850 can also communicate audibly using an audio codec 1860, which can receive spoken information from a user and convert it to usable digital information. The audio codec 1860 can likewise generate audible sound for a user, such as through a speaker, e.g., in a handset of the mobile computing device 1850. Such sound can include sound from voice telephone calls, can include recorded sound (e.g., voice messages, music files, etc.) and can also include sound generated by applications operating on the mobile computing device 1850.

The mobile computing device 1850 can be implemented in a number of different forms, as shown in the figure. For example, it can be implemented as a cellular telephone 1880. It can also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Figure 19:
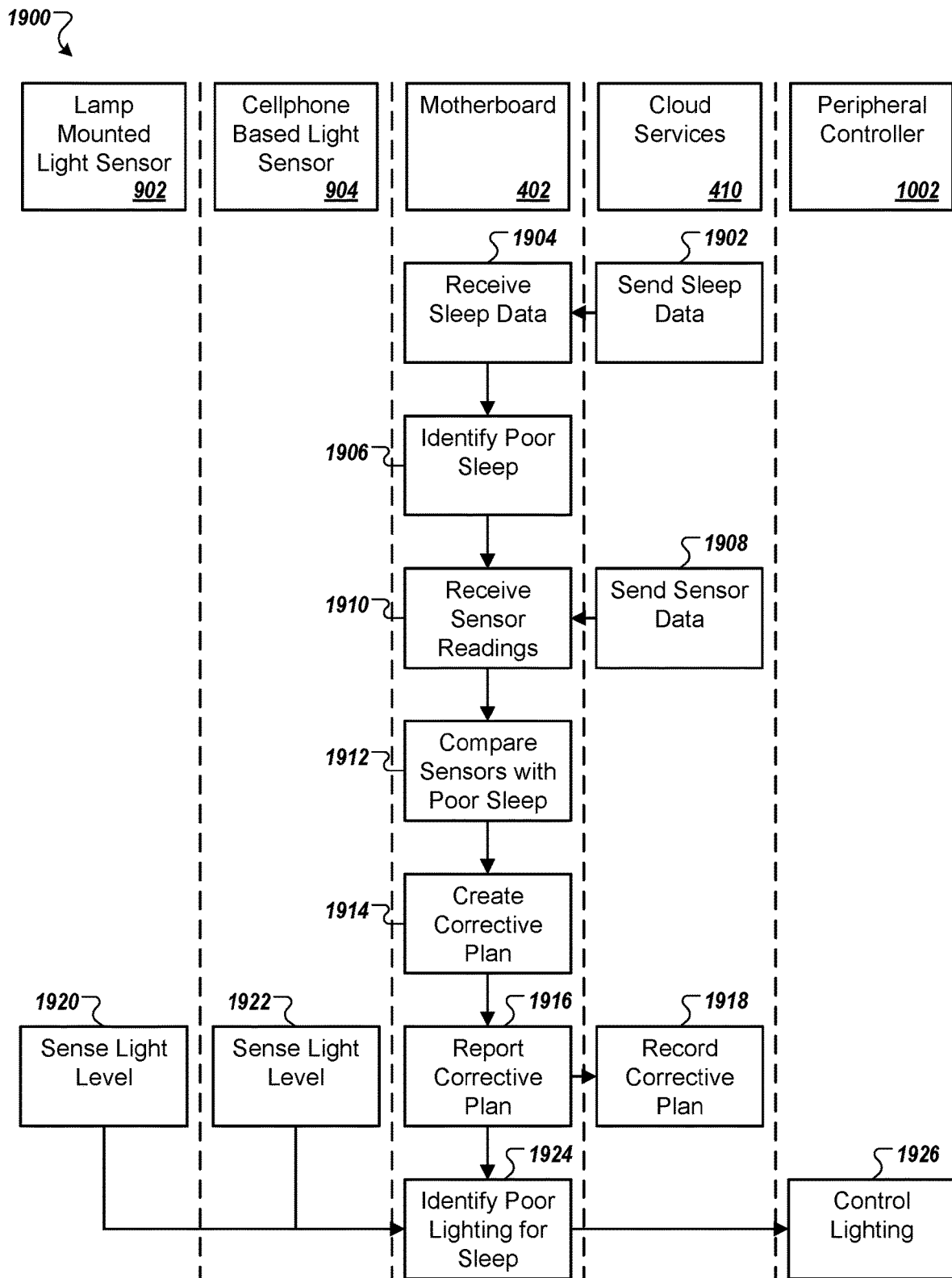
FIG. 19 is a swimlane diagram of an example process for determining a single phenomenon from sensors of the same type.

FIG. 19 is a swimlane diagram of an example process 1900 for responding to low quality sleep of a user. For clarity, the process 1900 is being described with reference to components of the data processing system 400. However, other system or systems can be used to perform the same or a similar process.

In the process 1900, a user is sleeping a bed equipped with a data processing system such as those described in this document. The user's bed is in the user's bedroom, which is equipped with a number of sensors and automated devices. These include a lamp with a light sensor connected to the data processing system and window blinds that can be opened and closed by the data processing system. Further, the user's cellular phone is in communication with the data processing system. Unbeknownst to the user in the process 1900, lights outside the user's window occasionally come on. These lights partially illuminate the user's bedroom and disturb the user's sleep without waking the user fully awake. To correct for this, the user's bed is able to identify these periods of restlessness, identify the problem with the illumination, and take a corrective action that will result in better sleep for the user.

The process 1900 can begin, for example, when cloud services 410 send 1902 sleep data to a receiving 1904 motherboard 402. For example, cloud services 410 such as the user account cloud 410c and/or sleep data cloud 410b can track the user's sleep data reported by the motherboard 402. Once enough data is collected, or on a different schedule (e.g., once a week or when computing resources are not otherwise assigned), the motherboard 402 can retrieve this sleep data that contains historical sleep metrics that represent a sleep quality of a user while the user was sleeping in a bed. For example, the sleep data may include biological readings (e.g., heartrate, breathing, and movement), aggregate readings (e.g., sleep quality on a numeric scale) or other appropriate metrics.

The motherboard 402 can identify 1906 periods of poor sleep quality. For example, the metrics may include a sleep quality values along with associated timestamps, and the motherboard 402 can identify incidences of low sleep quality values and their associated time stamps. Examples of user behavior that can be indicative low sleep quality include, but are not limited to, excessive motion, increased heart rate, and an increase in respiration rate.

The cloud services 410 can send 1908 sensor data to the motherboard 402 and the motherboard 402 can receive 1910 the sensor data. For example, in order to identify environmental factors that might be causing the periods of low sleep quality, the motherboard 402 can request historical sensor data that describes the environment the user is sleeping in during these periods. This historical sensor data may be stored in, and served by, the bed data cloud 410a, the sleep data cloud 410b, the environment cloud 1600, and/or other cloud services.

With this data, the motherboard 402 can compare 1912 the sensor data during periods of poor sleep against periods of better sleep. As has been previously described, the user's sleep is being disturbed by a light outside the window. This environmental phenomenon may be embodied in the sensor data received from, for example, a light sensor 902 on the user's lamp and a light sensor on the user's cellular phone 904. As such, the motherboard 402 may determine that in periods of poor sleep, the light sensor 902 may be reporting greater levels of illumination and the cellular phone 904 may be reporting a change in the color of illumination.

This determination may be made by the motherboard 402 without any specific user input and/or without the user's knowledge. For example, the motherboard 402 may routinely perform these kinds of comparisons to identify opportunities for improved user sleep. If no such opportunities are found, the motherboard 402 need not report anything to the user. As will be shown below, when this opportunity is found, the result may or may not be reported to the user and/or the system may make adjustments without needing user input.

The motherboard 402 can create 1914 a corrective plan to improve the user's sleep quality. In this example, the motherboard 402 may determine that a cause of the user's sleep quality problems is the illumination in the user's environment. The motherboard 402 may examine, for example, historical records of the illumination devices controlled by the motherboard 402 to determine if these devices are the cause of the problematic illumination. For example, the motherboard 402 can access these historical records from local memory (e.g., computer memory 512) and/or from cloud services (e.g., bed data cloud 410a).

In this case, the motherboard 402 does not determine that the devices are causing the problematic illumination. However, the motherboard 402 may determine that the user's window blinds are open at night, allowing light to enter the user's environment. As such, the motherboard can create a corrective plan that includes computer-operable instructions to 1) close the blinds when the user falls asleep, 2) close the blinds when sensed illumination increases above a threshold value, 3) closes the blinds when the user's sleep quality falls below a threshold, and/or 4) closes the blinds at times of the day when the lights have historically illuminated the user's environment. For example, the corrective plan can include a file (e.g., an XML, file or other structured file format) containing computer-readable data (e.g., binary, ASCII characters) with instructions to perform one or all of the described remedies.

Additionally or alternatively, the corrective plan can include human-readable text generated to describe to the user 1) that they are experiencing low-quality sleep, 2) the identified cause of the low quality sleep (i.e., the illumination), 3) steps the user can take to improve their sleep (e.g., closing the blinds themselves, moving their bed away from the window), and/or 4) a description of the computer-readable instructions that will be used by the motherboard 402 to automate the user's devices to improve the user's sleep.

This report can be communicated to the user through any technologically appropriate scheme. For example, an application or web-browser on the users cellular phone may show the report, the report may be emailed to the user's email address, or the report can be added to a daily report given to the user upon waking (e.g., such a report may also include the day's weather prediction, traffic warnings, and/or calendar agenda).

The motherboard 402 can report 1916 the corrective plan to a receiving 1918 cloud service 410. For example, the motherboard 402 may transmit the report, or elements (e.g., just the computer-readable elements) to a cloud service 410 such as the bed data cloud 410a and/or the sleep data cloud 410b. This report may then be analyzed and/or made available for further analysis. For example, if the user shares the bed with another user, or if there is another user in a different room of the same house, the sleep data cloud 410b can analyze the other user's sleep history to determine if the other user has experienced low quality sleep at the same time and if the other user is likely to benefit from corrective plan. Additionally, the corrective plan may be made available by the cloud services 410 if, for example, the user replaces their current bed with a new bed having a new data processing system.

Going forward, the motherboard 402 may operate with the corrective plan in place. For example, if the corrective plan calls for closing the blinds at a particular time or in response to a detection that the user is asleep, the motherboard 402 may close the blinds at the designated time. Described here is a case in which the user prefers to fall asleep with soft under-bed lighting lit and the blinds open.

The lamp-mounted light sensor and the cellular phone based light sensor 904 can sense light levels 1920 and 1922, and report these light levels to the motherboard. For example, the lamp mounted light sensor 902 may be in generally constant communication with the motherboard, and the cellular phone may report light readings when the cellular phone is connected to the same WiFi network as the motherboard 402. When the user goes to sleep, having the blinds open and the under-bed lighting lit, the light levels reported by the light sensors 902 and 904 to the motherboard 402 may be below the threshold at which the corrective plan indicates poor sleep by the user.

Later, the light outside of the user's window may come on, and the sensors 902 and 904 may report the increased illumination and change in illumination color to the motherboard 402. The motherboard 402 may then identify 1924 that the lighting threshold value has been crossed. In order to control 1926 the lighting in the room, the motherboard 1926 may take one or more corrective actions. In this example, the motherboard 402 may issue a command to an environmental control system, such as the peripheral controller 1002 to close the blinds, and another command to the same or a different environmental control system, such as a lighting controller (not shown) to turn off or turn down the under-bed lighting. In general environmental control systems may include one or more of the peripheral controllers 1000-1006 and/or any other technologically appropriate device that can receive commands to affect the environment in which a user is sleeping.

While a particular number, type, and order of operations have been shown, it will be understood that different numbers, types, and orders of operations may be used. For example, after the system has been configured to use the corrective plan, the user may add or remove one or more peripheral controller or sensor to the system. In the case of a new light sensor being added, this new light sensor may be included in the identification 1924 of illumination levels that can cause low quality sleep. In another case of a new automated lighting system being added, the corrective plan can be updated include instructions to, or responded to by the motherboard 402, by turning off the new lighting system.

In some cases, more or less data may be communicated to the cloud services 410. For example, the sleep data 1902 and sensor data 1908 may be stored by the motherboard 402 and/or the corrective plan 1918 may never need be reported to the cloud services 410. In some cases, this may support the use of beds that are completely separated from the Internet and not able to access any cloud services.

Figure 20:
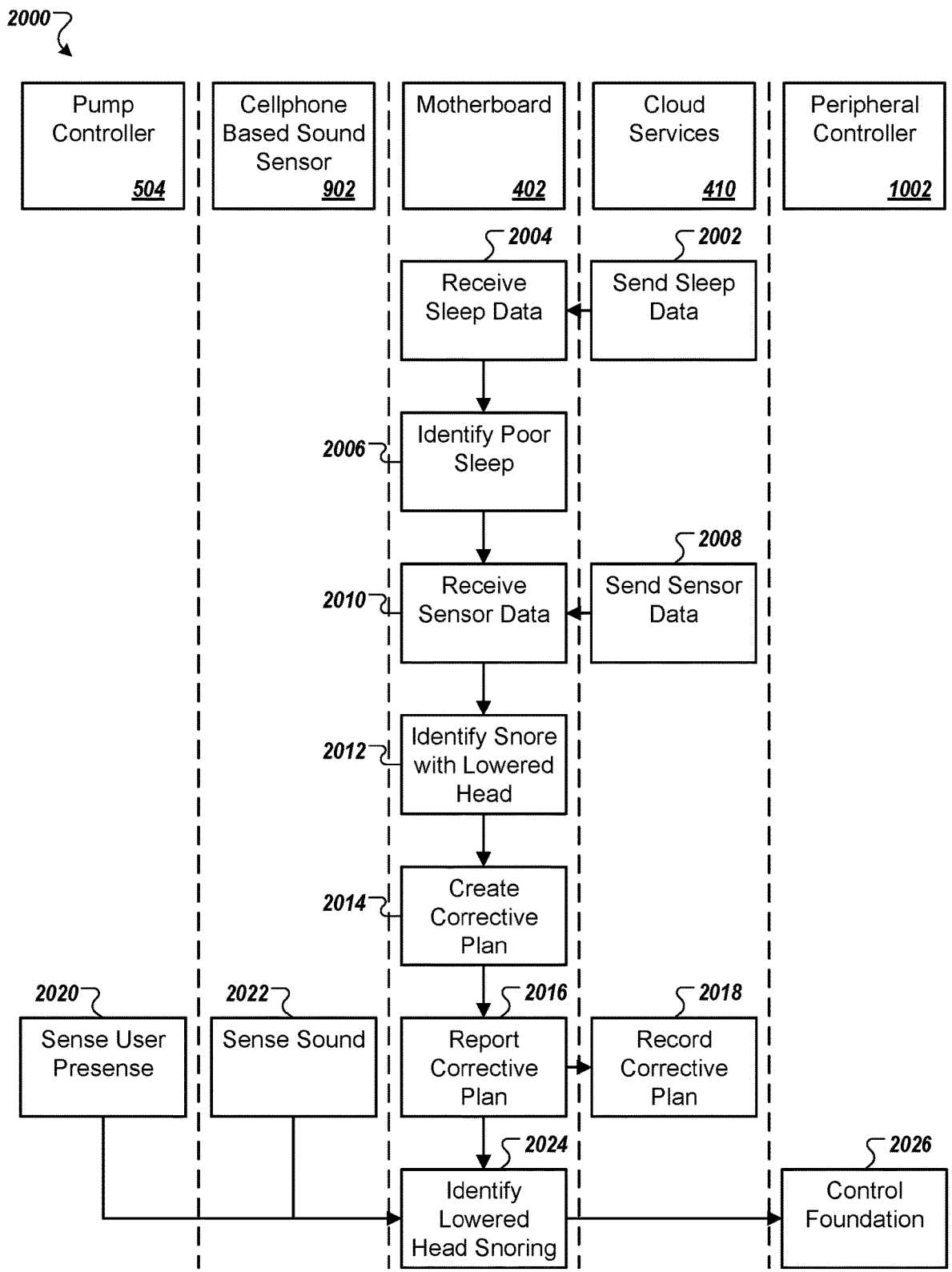
FIG. 20 is a swimlane diagram of an example process for determining a single phenomenon from sensors of different types.

FIG. 20 is a swimlane diagram of an example process 2000 for responding to low quality sleep of a user. For clarity, the process 2000 is being described with reference to components of the data processing system 400. However, other system or systems can be used to perform the same or a similar process.

In the process 2000, the user of a bed is experiencing reduced sleep quality due to snoring. For some users, snoring may be reduced or eliminated by elevating the user's head. Additionally, many users are not aware of the duration and intensity of their snoring, as it occurs when they are sleep. The process 2000 includes both a response by the automated bed to elevate the users head, as well as a report to the user informing the user of their snoring issue. The user may then respond to this notification as appropriate, including but not limited to changing their sleeping habits and/or seeking medical advice related to their snoring.

The process 2000 can begin, for example, when cloud services 410 send 2002 sleep data to a receiving 2004 motherboard 402. For example, cloud services 410 such as the user account cloud 410c and/or sleep data cloud 410b can track the user's sleep data reported by the motherboard 402. Once enough data is collected, or on a different schedule (e.g., once a week or when computing resources are not otherwise assigned), the motherboard 402 can retrieve this sleep data that contains historical sleep metrics that represent a sleep quality of a user while the user was sleeping in a bed. For example, the sleep data may include biological readings (e.g., heartrate, breathing, and movement), aggregate readings (e.g., sleep quality on a numeric scale) or other appropriate metrics.

The motherboard 402 can identify 2006 periods of poor sleep quality. For example, the metrics may include a sleep quality values along with associated timestamps, and the motherboard 402 can identify incidences of low sleep quality values and their associated time stamps.

The cloud services 410 can send 2008 sensor data to the motherboard 402 and the motherboard 402 can receive 2010 the sensor data. For example, in order to identify environmental factors that might be causing the periods of low sleep quality, the motherboard 402 can request historical sensor data that describes the environment the user is sleeping in during these periods. This historical sensor data may be stored in, and served by, the bed data cloud 410a, the sleep data cloud 410b, the environment cloud 1600, and/or other cloud services.

With this data, the motherboard 402 can compare 2012 the sensor data during periods of poor sleep against periods of better sleep. As has been previously described, the user's sleep is being disturbed by a periods of heavy snoring. This phenomenon may be embodied in the sensor data received from, for example, sound sensor 902 on the user's cellular phone. As such, the motherboard 402 may determine that in periods of poor sleep, the sound sensor 902 may be reporting sound data that is consistent with the sound of the user snoring. For example, if the motherboard 402 detects low frequency sound of frequency of approximately 500 hz, the motherboard 402 can identify that sound as user snoring.

This determination may be made by the motherboard 402 without any specific user input and/or without the user's knowledge. For example, the motherboard 402 may routinely perform these kinds of comparisons to identify opportunities for improved user sleep. If no such opportunities are found, the motherboard 402 need not report anything to the user. As will be shown below, when this opportunity is found, the result may or may not be reported to the user and/or the system may make adjustments without needing user input.

The motherboard 402 can create 2014 a corrective plan to improve the user's sleep quality. In this example, the motherboard 402 may determine that a cause of the user's sleep quality problems is the user's snoring. The motherboard 402 may examine, for example, historical records of the pump controller 504 and the sound sensor 902 to identify that when the user is present in bed—based on pressure readings from the pump controller 504—and when the sound of snoring is detected—based on input from the sound sensor 902—the user is experiencing reduced sleep quality.

As such, the motherboard 402 can create a corrective plan that includes computer-operable instructions to elevate the head portion of the bed's foundation when the user is detected in bed and sleep. In one alternative, the motherboard 402 can create a corrective plan that includes computer-operable instructions to elevate the head portion when the user is detect in bed, asleep, and generating sounds constant with snoring. For example, the corrective plan can include a file (e.g., an XML, file or other structured file format) containing computer-readable data (e.g., binary, ASCII characters) with instructions to perform one or all of the described remedies.

Additionally or alternatively, the corrective plan can include human-readable text generated to describe to the user 1) that they are experiencing low-quality sleep, 2) the identified cause of the low quality sleep (i.e., snoring), 3) steps the user can take to improve their sleep (e.g., sleeping with an elevated head, seeking medical advice), and/or 4) a description of the computer-readable instructions that will be used by the motherboard 402 to automate the user's devices to improve the user's sleep.

This report can be communicated to the user through any technologically appropriate scheme. For example, an application or web-browser on the users cellular phone may show the report, the report may be emailed to the user's email address, or the report can be added to a daily report given to the user upon waking (e.g., such a report may also include the day's weather prediction, traffic warnings, and/or calendar agenda).

The motherboard 402 can report 2016 the corrective plan to a receiving 2018 cloud service 410. For example, the motherboard 402 may transmit the report, or elements (e.g., just the computer-readable elements) to a cloud service 410 such as the bed data cloud 410a and/or the sleep data cloud 410b. This report may then be analyzed and/or made available for further analysis. For example, if the user shares the bed with another user the sleep data cloud 410b can analyze the other user's sleep history to determine if the other user has experienced low quality sleep when the first user is snoring. Additionally, the corrective plan may be made available by the cloud services 410 if, for example, the user replaces their current bed with a new bed having a new data processing system.

Going forward, the motherboard 402 may operate with the corrective plan in place. For example, if the corrective plan calls for elevating the head portion of the bed's foundation when the user is in the bed and asleep, the motherboard 402 may elevate the head portion of the foundation when these conditions are met.

The pump controller 504 can sense user presence 2020 and report to the motherboard 402. For example, the pump controller 504 may have one or more pressure sensors that read when pressure in the bed increased, for example from a user laying in the bed. The pump controller 504 can then report these presence events to the motherboard 402. Additionally or alternatively, the pump controller 504 can report the pressure readings to the motherboard 402, and the motherboard 402 can determine if those readings indicate the user is present in the bed. In addition to presence, other phenomena may be sensed by the pump controller 504. For example, the pump controller 504 may sense pressure changes due to user breathing and/or heartbeat. These readings may be used to, for example, determine if the user is asleep, and determine the sleep state or quality of sleep that the user is experiencing.

Similarly, the sound sensor 902 can sense 2022 sound in the user's environment and report that reading to the motherboard 402. Using this reading, the motherboard 402 (or other technologically appropriate element) can examine the sound reading to detect user snoring.

If the motherboard 402 identifies 2024 that the user is in the bed, asleep, and if snoring sounds are detected when the bed's foundation is flat, the motherboard may react according to the corrective plan. In this case, the motherboard 402 can engage the peripheral controller 1002 that controls the bed's foundation to control 2026 the foundation and elevate the bed's head component. By doing so, the motherboard 402 may thus elevate the user's head, reducing or eliminating the user's snoring or the effects of the snoring.

While a particular number, type, and order of operations have been shown, it will be understood that different numbers, types, and orders of operations may be used. For example, in a bed without an articulated foundation, other peripheral controllers or other output devices may be engaged in an attempt to alleviate the user's snoring. For example, the firmness of the mattress may be changed to encourage the user to roll and/or a humidifier may be engaged to increase the humidity in the user's environment, and/or the foundation may move through a series of positions and elevations in an attempt to find a position that stops the snoring.

In some cases, more or less data may be communicated to the cloud services 410. For example, the sleep data 2002 and sensor data 2008 may be stored by the motherboard 402 and/or the corrective plan 2018 may never need be reported to the cloud services 410. In some cases, this may support the use of beds that are completely separated from the Internet and not able to access any cloud services.

In some cases, two users may share a bed and only one of the two users may snore. In such a case, the motherboard 402 can detect which of the two users is snoring and apply the corrective plan only to that user. In one configuration, each of the two users has a cellar phone that they plug in to charge on a nightstand on each of their respective sides of the bed. This configuration creates a system in which there are two sound sensors, each closer to one user and farther from the other. To determine which user is the one that is snoring, the motherboard may compare the magnitude of the sound readings from the two cellular phones to determine which is greater. Then, the motherboard 402 may determine the user with the cellular phone reporting louder snoring is the user that is snoring. Additionally or alternatively, the motherboard 402 may compare the sound input to the pressure readings from the pump controller 504. As snoring is caused by user breathing, the motherboard 402 can examine the pressure readings and the sound readings to identify snoring sounds and breathing-based pressure changes that are occur with the same frequency. The motherboard 402 may then determine that the user whose breathing matches the snoring is the user that is snoring. In such as case, the motherboard 402 may apply the corrective action only to the user that is snoring and not to the other user.

Example Foot Warming System

Figure 21:
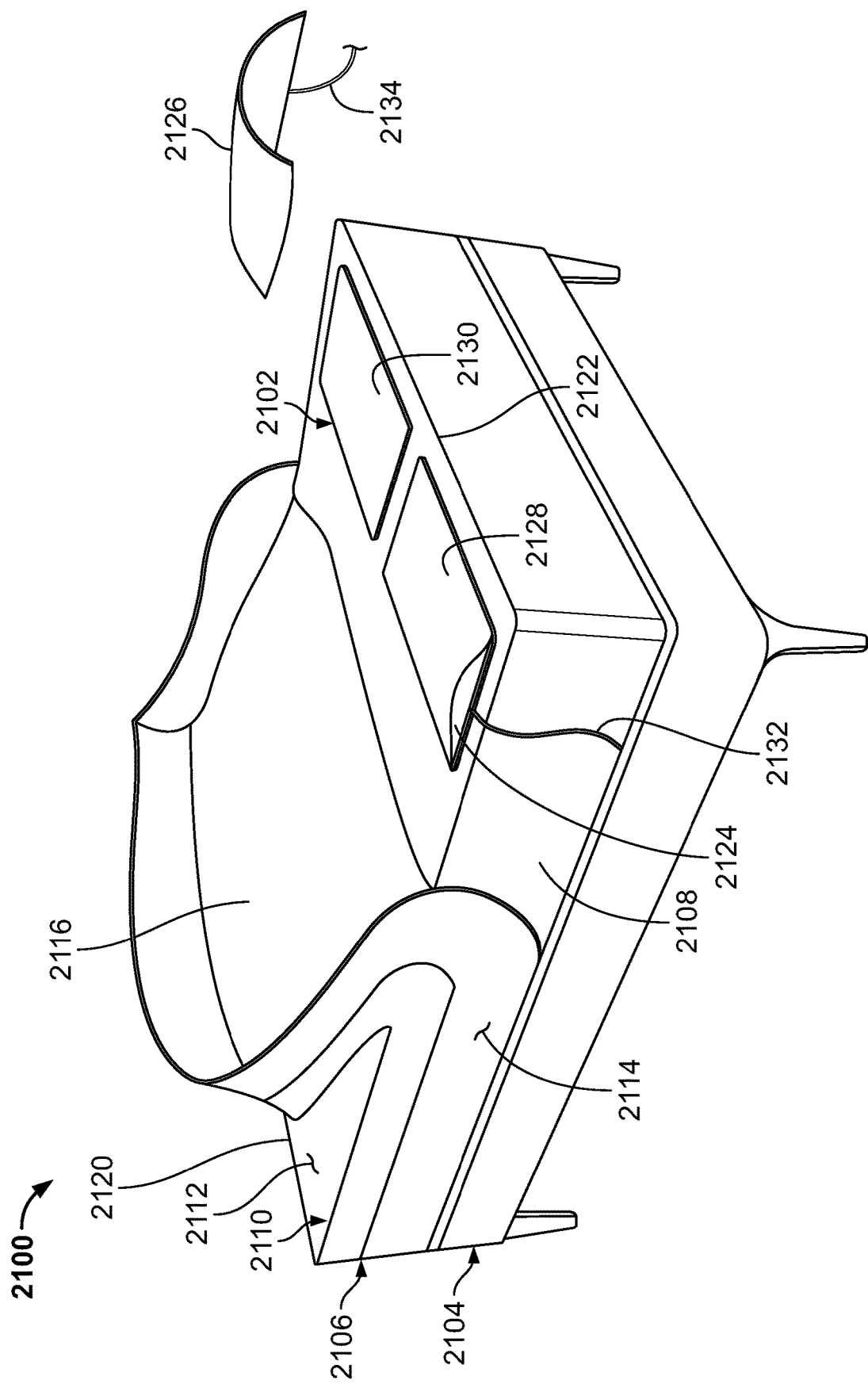
FIG. 21 is a perspective view of an example bed having a foot warming system.

FIG. 21 is a perspective view of an example bed 2100 having a foot warming system 2102. The bed 2100 can have a foundation 2104 and a mattress 2106 supported by the foundation 2104. In some embodiments, the bed 2100 can be an air bed system such as the air bed system 100 shown in FIG. 1 and having one, more than one, or all of the features described above with respect to FIGS. 1-20. In other embodiments, the bed 2100 can be another type of bed suitable for the application, such as a bed having foam and/or springs without inflatable air chambers. In some embodiments, the foundation 2104 can be an articulable foundation. In other embodiments, the foundation 2104 need not be articulable. In some embodiments, the bed 2100 need not include any foundation at all.

In the embodiment shown in FIG. 21, the mattress 2106 includes a support structure 2108 and a cover 2110 configured to cover the support structure 2108. The cover 2110 has a top portion 2112 positioned on a top of the support structure 2108, side portions 2114 extending around the outside of the support structure 2108, and a bottom portion (not shown) so as to substantially enclose the support structure 2108. The support structure 2108 is configured to support a user sleeping or otherwise resting on the mattress 2106, and can include foam, springs, inflatable air chambers, and/or one or more other suitable mattress components. The cover 2110 can also include an additional padding layer 2116 at the top portion 2112, such as a pillow top layer, a ticking layer, and/or other material suitable for the application.

The mattress 2106 can include a head 2120 and a foot 2122. The foot warming system 2102 can be positioned at or near the foot 2122 of the mattress 2106 in a location configured for warming feet of a user laying on the mattress 2106. As shown in FIG. 21, the foot warming system 2102 can include one or more heating units 2124 and 2126, envelopes 2128 and 2130, electrical connectors 2132 and 2134 (such as one or more cables or wires), and one or more power sources (shown in FIG. 27). In some embodiments, the power source can be a pump controller (such as control box 124 shown in FIGS. 1 and 2) or an articulation controller (such as for controlling articulation of an adjustable base). In other embodiments, the power source can be another controller or power source suitable for the application.

The heating units 2124 and 2126 can be positioned inside the mattress 2106. In some embodiments, the heating units 2124 and 2126 can comprise an electrically conductive fabric, such as a carbon-filled polymer material, for generating heat. In other embodiments, the heating units 2124 and 2126 can comprise another electrical assembly suitable for the application, such as resistance wiring and fabrics. The heating units 2124 and 2126 can be positioned inside the mattress cover 2110 and on top of the support structure 2108 so as to be between the support structure 2108 and the mattress cover 2110. The electrically conductive fabric can be relatively flexible and can heat relatively evenly, to provide a positive foot warming experience for the user with little to no adverse impact on the softness and overall comfort of the mattress 2106.

In some embodiments, the heating units 2124 and 2126 can be attached to the support structure 2108. For example, FIG. 21 shows the heating unit 2124 attached to the support structure 2108 via the envelope 2128. The heating unit 2124 can be positioned inside the envelope 2128, which can be affixed to a top of the support structure 2108 via adhesive, thread, or another mechanism suitable for the application.

In the illustrated example, the heating unit 2124 is removably attached to the support structure because it is removably inserted into the envelope 2128. For example, the heating unit 2126 is shown removed from its corresponding envelope 2130. Accordingly, the envelopes 2128 and 2130 allow for the heating units 2124 and 2126 to be held in place with respect to the mattress 2106 while also being removable for repair or replacement.

In some embodiments, the envelopes 2128 and 2130 can be omitted. For example, in some embodiments the heating units 2124 and 2126 can be affixed to the support structure 2108 without the envelopes 2128 and 2130. In other embodiments, the heating units 2124 and 2126 can be attached to the cover 2110, the fire resistant cap 2136, or other layer inside the mattress 2106. Such attachments can be via adhesive, stitching, or other fastening mechanism suitable for the application.

While FIG. 21 shows the mattress 2106 with the cover 2110 partially removed to show internal components, the cover 2110 would be closed during normal operation of the mattress 2106, substantially concealing the foot warming system 2102.

The power source can be electrically connected to the heating units 2124 and 2126 so as to selectively drive (or power) the heating units 2124 and 2126 to heat the mattress 2106 at or near the foot 2122 of the mattress 2106. This can warm the mattress 2106 at a user's feet, for example, to improve comfort and/or help induce sleep more rapidly.

Figure 22:
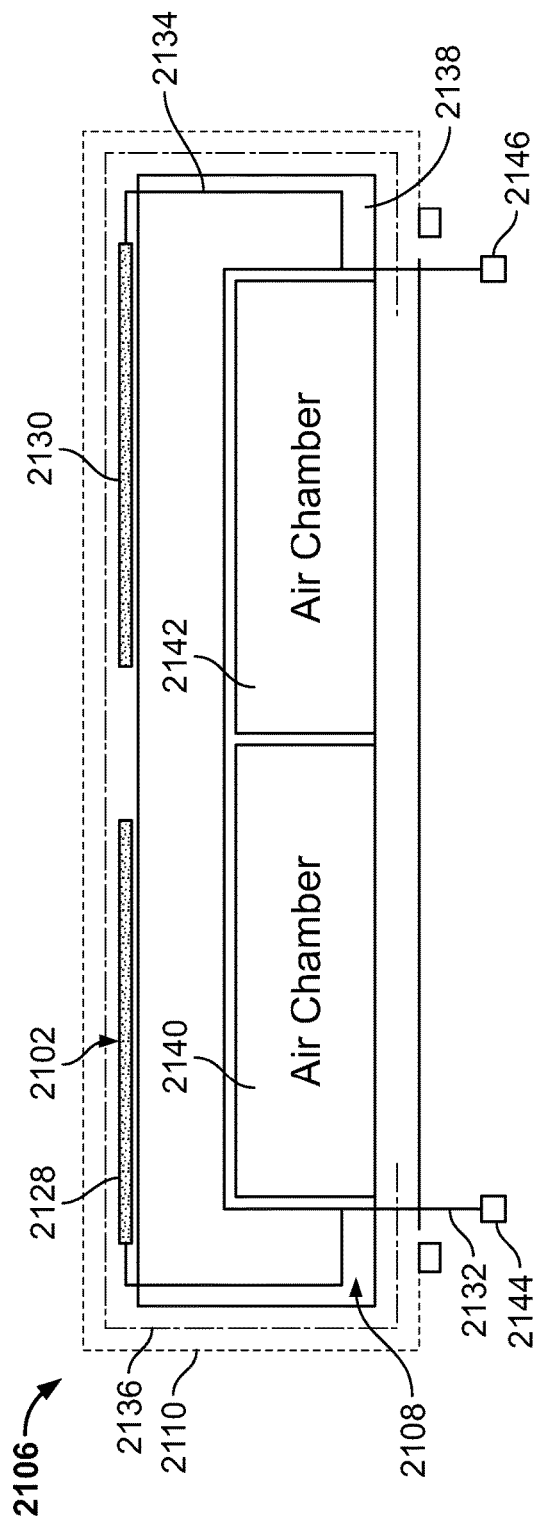
FIG. 22 is a schematic end view of a mattress having a foot warming system.
Figure 23:
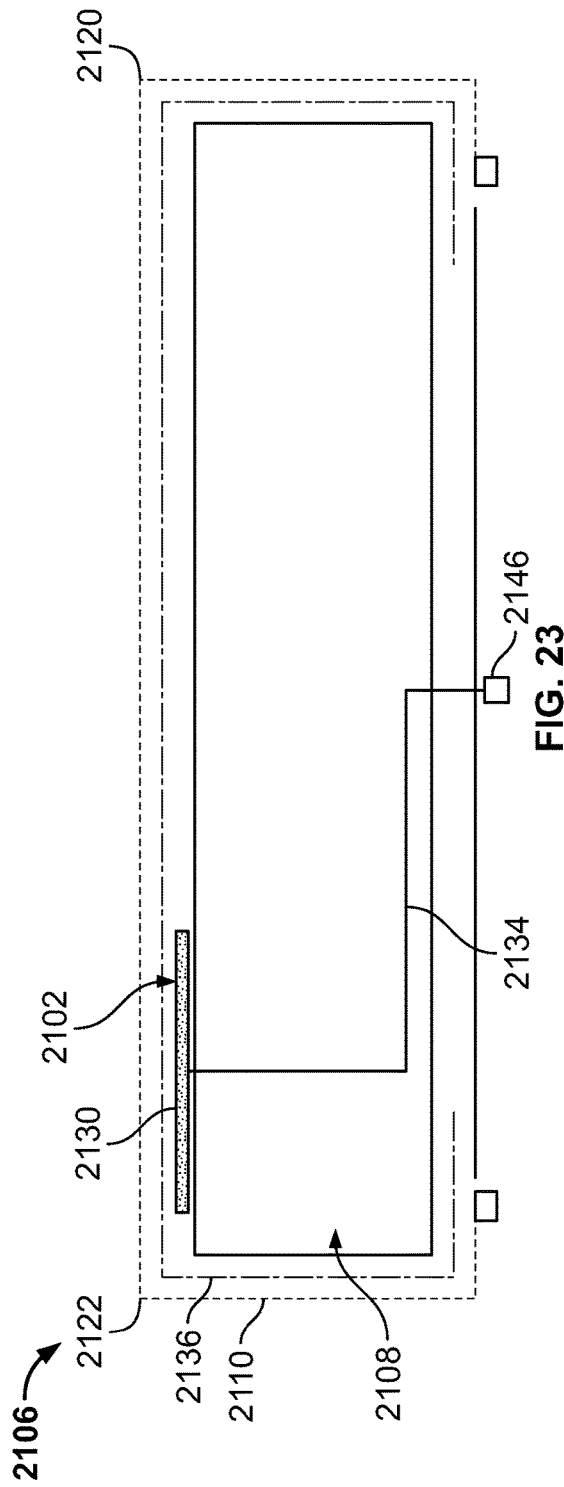
FIG. 23 is a schematic side view of the mattress of FIG. 22.

FIG. 22 is a schematic end view of the mattress 2106 and the foot warming system 2102. FIG. 23 is a schematic side view of the mattress 2106 and the foot warming system 2102. As shown in FIGS. 22 and 23, the mattress 2106 can include a fire resistant cap 2136 positioned inside the cover 2110. The fire resistant cap 2136 can cover internal components of the mattress, including the support structure 2108 and components of the foot warming system 2102 (including the envelopes 2128 and 2130 and the heating units 2124 positioned therein). In some embodiments, the fire resistant cap 2136 can include a 4 ounce jersey knit material. In other embodiments, the fire resistant cap 2136 can include one or more other materials suitable for the application. In still other embodiments, the fire resistant cap 2136 can be omitted.

FIG. 22 also shows an embodiment with the support structure 2108 including foam 2138 and air chambers 2140 and 2142. In the embodiment shown, the foam 2138 is an upside-down foam tub covering the air chambers 2140 and 2142. The air chambers 2140 and 2142 are adjustably inflatable air chambers each sized for supporting first and second users respectively, and can be the same as or similar to the air chambers 114A and 114B described above. The envelopes 2128 and 2130 can be adhered or otherwise attached to the foam 2138, with the heating units 2124 and 2126 positioned inside.

FIGS. 22 and 23 also show an example embodiment of positioning of the electrical connectors 2132 and 2134. As shown in FIG. 22, the electrical connectors 2132 and 2134 include wires extending along the sides of the mattress 2106, partially through the foam 2138. The foam 2138 can define pathways allowing the electrical connectors 2132 to be routed through. In one embodiment, the electrical connector 2132 can be routed through a slit in cut in the foam 2138. In another embodiment, the electrical connector 2132 can be routed through a hole bored through the foam 2138. The electrical connectors 2132 and 2134 can terminate at connector ends 2144 and 2146, which can connect to one or more power sources (not shown in FIGS. 22 and 23) for powering the heating units 2124 and 2126.

FIG. 23 shows the connector 2134 from a side view, extending from the envelope 2130 (with the heating unit 2126 positioned inside) near the foot 2122 of the mattress 2106 to the connector end 2146 positioned near a longitudinal center of the mattress 2106. By positioning the connector end 2146 near the longitudinal center of the mattress 2106, the mattress 2106 can be used with adjustable foundations to raise and lower the head 2120 and foot 2122 of the mattress 2106 while allowing the connector end 2146 to remain relatively stationary during articulation. This can allow the heating units 2124 and 2126 to be raised and lowered with the mattress 2106 while being connected to and powered by a power source that is relatively stationary during articulation.

FIGS. 24A-24C are top perspective views of a portion of the foot warming system 2102, including the heating unit 2124 and the envelope 2128. In some embodiments, the envelope 2128 can include an envelope top 2148 and an envelope bottom 2150. The envelope top 2148 can be attached to the envelope bottom 2150 around substantially all of their perimeters except for a portion to define an opening 2152. The opening 2152 can allow for insertion and removal of the heating unit 2124. In some embodiments, the opening 2152 can be sized smaller than the heating unit 2124. The heating unit 2124 can comprise an electrically conductive fabric that is flexible so as to allow the heating unit 2124 to be compressed to fit through the opening 2152 and then expanded to lay flat within the envelope 2128. In some embodiments, the opening 2152 can remain open while in other embodiments the opening 2152 can be closed. For example, the envelope 2128 can include a closure mechanism, such as a zipper, hook-and-loop fasteners (commonly called "VELCRO" after the VELCRO brand fasteners), or other suitable mechanism, to partially or totally close the opening 2152 such that the heating unit 2124 can be encapsulated inside. In other embodiments, the opening 2152 can be omitted and the heating unit 2124 can instead be sealed inside the envelope 2128 substantially permanently.

FIG. 24A shows the heating unit 2124 being inserted through the opening 2152. FIG. 24B shows the heating unit 2124 positioned inside the envelope 2128 and laying substantially flat. FIG. 24C shows the fire resistant cap 2136 in the process of being draped over the envelope 2128 and the heating unit 2124.

In some embodiments, both the fire resistant cap 2136 and the envelope 2128 can include fire resistant material. For example, in some embodiments both the envelope top 2148 and the envelope bottom 2150 can include fire resistant material. In such embodiments, the envelope 2128 can provide fire protection from both the top and the bottom. In other embodiments, the envelope bottom 2150 can include fire resistant material while the envelope top 2148 can omit fire resistant material. For example, the envelope top 2148 can be a breathable mesh with little or no fire resistance. In such embodiments, the fire resistant cap 2136 can be relied on to provide fire protection from the top and the envelope bottom 2150 can be relied on to provide fire protection from the bottom. In some embodiments, the envelope 2128 can include fire resistant material and the fire resistant cap 2136 can be omitted.

FIGS. 25A and 25B are top perspective views of envelopes 2528 and 2530. In the embodiment shown, the envelopes 2528 and 2530 are similar to the envelopes 2128 and 2130 shown in FIGS. 21-24C, except that the envelopes 2528 and 2530 include attachment mechanism 2560. The attachment mechanism 2560 can connect the envelope 2528 to the envelop 2530 along respective edges thereof. In such embodiments, the attachment mechanism 2560 can help hold each of the envelopes 2528 and 2530 in place, by allowing each to support the other. In some of such embodiments, the electrical connectors 2132 and 2134 can be positioned to provide further support for holding the envelopes 2528 and 2530 in place in conjunction with the attachment mechanism 2560. In some of such embodiments, the envelopes 2528 and 2530 can be held in place without attaching the envelopes 2528 and 2530 directly to the support structure 2108.

In some embodiments, the attachment mechanism 2560 can include hook-and-loop fasteners (commonly called "VELCRO" after the VELCRO brand fasteners). In other embodiments, the attachment mechanism can be another mechanism suitable for the application.

FIG. 26 is a perspective view of a bottom of the envelope 2128, showing an adhesive backing 2662. The adhesive backing 2662 can adhere the envelope 2128 to the support structure 2108 or cover 2110 of the mattress 2106. In some embodiments, the adhesive backing 2662 can cover all or substantially all of one side of the envelope 2128. In other embodiments, the adhesive backing 2662 can cover less than all of one side of the envelope 2128. For example, in one embodiment the adhesive backing 2662 can be positioned in four corners of the envelope 2128, with space in-between. In such embodiments, the envelope 2128 can be adhered, for example, to the support structure 2108 of the mattress 2106 only at corners of the envelope 2128.

Figure 27:
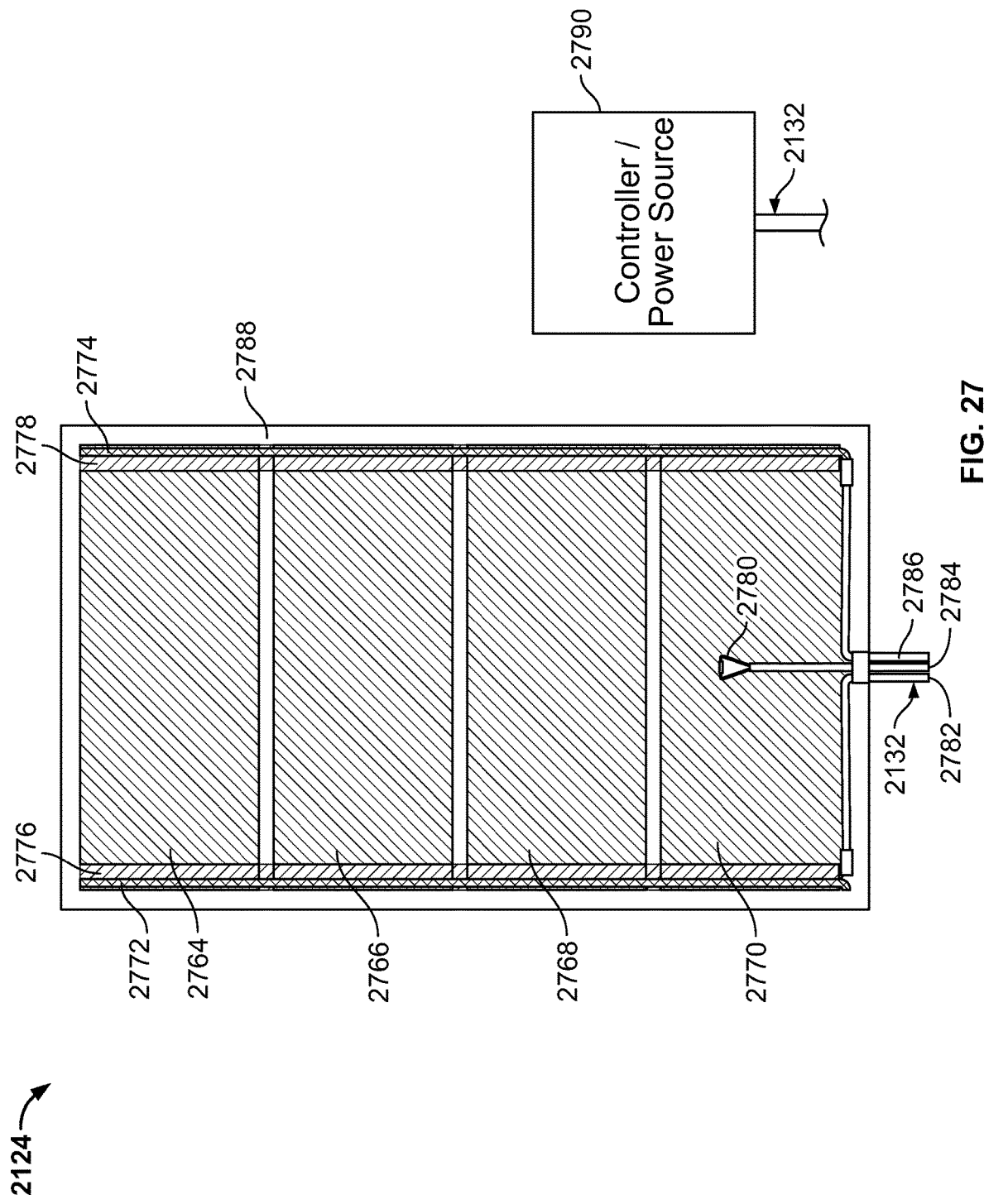
FIG. 27 is a top view of components of a foot warming system.

FIG. 27 is a top view of components of the foot warming system 2102. In the embodiment shown in FIG. 27, the heating unit 2124 includes electrically conductive fabric heating elements (heating elements 2764, 2766, 2768, and 2770), bus bars 2772 and 2774, reinforcing tape 2776 and 2778, temperature sensor 2780, wires 2782, 2784, and 2786, and bonding film 2788. The connector 2132 can be a wire harness that includes the wires 2782, 2784, and 2786. The wire 2782 electrically connects the bus bar 2772 to a controller (power source) 2790 and the wire 2786 electrically connects the bus bar 2774 to the controller 2790. The wire 2784 electrically connects the temperature sensor 2780 to the controller 2790, which can receive temperature signals from the temperature sensor 2780 and power the heating unit 2124 as a function of the received temperature signals. While only one wire 2784 is shown connecting to the temperature sensor 2780, multiple wires can be used. In some embodiments, the controller 2790 can be a pump controller (such as control box 124 shown in FIGS. 1 and 2) or an articulation controller (such as for controlling articulation of an adjustable base). In some of such embodiments, the controller 2790 can perform none, some, or all of the functions described above with respect to those controllers. In other embodiments, the controller 2790 can be another controller or power source suitable for the application. For example, the controller 2790 can be a controller dedicated to operating the foot warming system 2102 alone, or operating the foot warming system 2102 in conjunction with one or more other systems.

In some embodiments, multiple electrically conductive fabric heating elements can extend from bus bar 2772 to bus bar 2774. In the illustrated embodiment, four separate fabric heating elements (the heating elements 2764, 2766, 2768, and 2770) are included. Gaps are shown spacing adjacent ones of the heating elements 2764, 2766, 2768, and 2770. In some embodiments, gaps between adjacent ones of the heating elements 2764, 2766, 2768, and 2770 can be about 0.5 inch. In some embodiments, gaps between adjacent ones of the heating elements 2764, 2766, 2768, and 2770 can be between 0.2 inch and 0.8 inch. In other embodiment, more or fewer heating elements can be used.

In some embodiments, the heating elements 2764, 2766, 2768, and 2770 can comprise carbon-based electrically conductive fabric, which can conduct electricity between the bus bars 2772 and 2774 and which has a suitable resistance to generate heat. The heating elements 2764, 2766, 2768, and 2770 can operate at relatively low power and heat relatively uniformly, thus warming a mattress with reduced risk of fire. For example, in some embodiments the power for the heating unit 2124 can be about 0.085-0.095 W/inch$^2$.

In some embodiments, the bus bars 2772 and 2774 can be tinned copper bus wires having a relatively thin diameter so as to allow for repeated bending when the mattress is in use. In some of such embodiments, the bus bars 2772 and 2774 can comprise wire braids. In other embodiments, the bus bars 2772 and 2774 can comprise conductive ink. In other embodiments, the bus bars 2772 and 2774 can have a different configuration as suitable for the application.

The temperature sensor 2780 can sense temperature at and around the heating unit 2124, to provide feedback to the controller 2790 for powering the heating unit 2124. In some embodiments, the temperature sensor 2780 can be placed proximate the heating element 2770. In some of such embodiments, the temperature sensor 2780 can be proximate to but slightly spaced from the heating element 2770 via a layer of material, such as a layer of polyimide film. In various embodiments, the temperature sensor 2780 can be a thermistor, a thermocouple, or another suitable temperature sensor.

The reinforcing tape 2776 and 2778 can be placed along edges of the heating elements 2764, 2766, 2768, and 2770 and the bus bars 2772 and 2774 to reinforce the heating unit 2124. The bonding film 2788 can include top and bottom layers of film that enclose the heating elements 2764, 2766, 2768, and 2770, the bus bars 2772 and 2774, the reinforcing tape 2776 and 2778, the temperature sensor 2780, and part of the wires 2782, 2784, and 2786. The bonding film 2788 can protect components contained therein from moisture and tampering. In some examples, the bonding film 2788 can be polyurethane or another polymer material suitable to encase the flexible heating elements 2764, 2766, 2768, and 2770.

The heating unit 2124 can be a relatively thin layer sized and configured for being positioned inside a mattress for warming feet of a user of the mattress. In some embodiments, the heating unit 2124 can be sized and positioned for heating only a limited portion of the mattress including the feet of the user but not the head and torso of the user. In some embodiments, the heating unit 2124 can have a width of between 21 inches and 31 inches and a depth of between 10 inches and 20 inches. In some embodiments, the heating unit 2124 can have a width of between 25 inches and 28 inches and a depth of between 14 inches and 18 inches. In other embodiments, the size and position of the heating unit 2124 can be varied as suitable for the application.

In operation, the controller 2790 can selectively power the heating unit 2124 (and/or the heating unit 2126) to generate heat and warm the mattress 2106. The foot warming system 2102 can be controlled automatically, via inputs from a user interface (such as a mobile device or other remote control), or both. Automatic control can be performed as a function of a number of sensed events, such as the user entering or leaving the bed and/or the user falling asleep or waking.

The controller 2790 can have intelligence to allow for benefits such as preheating, timed shut off, temperature regulation via the temperature sensor 2780, or other features that may enhance the user experience.

For example, the foot warming system 2102 can be controlled as a function of when the user goes to sleep. In one example, the user can identify an earliest time that they go to sleep. The controller 2790 can then drive the heating unit 2124 to warm for a predetermined time prior to this sleep time (e.g., 30 minutes) so that the mattress 2106 is warm when the user enters the mattress 2106.

In another example, the foot warming system 2102 may be turned on via an instruction from the user through a user interface indicating the intent of user going to bed. Upon the user entering the mattress 2106, the foot warming system 2102 can shut off automatically based on sensing the user entered in the mattress 2106, or can continue to run for a given amount of time. In another example, the foot warming system 2102 can run until the user falls asleep as determined by one or more sensors.

During this operation, the warming system 2102 can maintain a constant temp level or adjust to a preset level in response to one or more timed or sensed events. The foot warming system 2102 can operate at different power levels as appropriate for the situation. For example, the foot warming system 2102 can operate a high power level in order to initially heat the mattress 2106 quickly, and then to operate at a lower power to maintain a target temperature, such as operating via pulse wave modulation.

In another example, the controller 2790 can determine an expected bed time for a user of the bed. This determination can be made as a function of user inputs regarding bed time. Alternatively, this determination can be made automatically by the controller 2790 as a function of a learned sleep schedule that is based on sensed data of the user historically entering bed night after night. Based on this information, the controller 2790 can drive the foot warming system 2102 to heat the foot of the mattress 2106 to reach a target temperature prior to the expected bed time.

In some of such applications, the controller 2790 can reduce power upon a sensor detecting the user enters the mattress 2106. For example, the controller 2790 can cut power immediately such that the foot warming system 2102 only warms before the user enters the bed. Alternatively, the controller 2790 could slowly reduce power or reduce power after a given time period after the user enters the mattress 2106.

In another example, the controller 2790 can determine whether the user is asleep as a function of sensed data and then drive the foot warming system 2102 as a function of whether the user is determined to be asleep. For example, the foot warming system 2102 can be driven until the user falls asleep and shut off in response to determining that the user is asleep based on sensed data.

In another example, the controller 2790 can drive the foot warming system 2102 automatically in order to improve sleep quality. For example, the controller 2790 can access historical sleep metrics that represent sleep quality of a user while the user was sleeping in the bed and/or access historical sensor data that represent sensor readings that measure environmental conditions affecting the user while the user was sleeping in the bed, such as sensed temperature. The controller 2790 can identify in the historical sleep metrics incidences of low quality sleep experienced by the user and incidences of high quality sleep by the user and then generate a corrective plan that specifies a change to the foot warming system to improve sleep quality based on historical sleep metric incidences associated with high quality sleep. The controller 2790 can then drive the foot warming system 2102 according to the generated corrective plan. The corrective plan can be based on the user's own sleep data and/or aggregate sleep data from other individuals.

In another example the controller 2790 can achieve a desired temperature as a function of sensed temperature, as sensed by the temperature sensor 2780. The controller 2790 can drive the heating unit 2124 as a function of a difference between the sensed temperature and a target temperature such that the controller 2790 supplies more power to the electrically conductive fabric in response to determining a relatively large difference between the sensed temperature and the target temperature and the controller 2790 supplies less power to the heating unit 2124 in response to determining a relatively small difference between the sensed temperature and the target temperature.

In various embodiments, the foot warming system 2102 can be operated to improve user comfort and/or to induce rapid sleep onset. By warming the users feet upon entering the bed, some users have been shown to fall asleep more quickly, thus improving sleep quality. The foot warming system 2102 can be integrated into a mattress at a location suitable for a particular user with little or no negative impact on the comfort of the mattress. The foot warming system 2102 can actively monitor microclimate to maintain appropriate temperature. The foot warming system 2102 can be automatically controlled via sensed data, reducing or removing the need for user inputs. Various embodiments described herein can achieve one or more of these benefits, among others.

A number of embodiments of the invention have been described. Nevertheless, it will be understood that various modifications may be made without departing from the spirit and scope of the invention. For example, the heating units 2124 and 2126 can have different shapes, orientations, and construction than that illustrated and described. Moreover, one, more than one, or all of the features of the various systems described above can be combined as suitable for a given application. Similarly, one or more features present on one or more of the various embodiments can be considered optional, and need not necessarily be included in all embodiments. Accordingly, other embodiments are within the scope of the following claims.

What is claimed is:

1. A bed system comprising:
   a mattress cover;
   a first layer having a top surface and an opposite bottom surface, the top surface covered by the mattress cover, the first layer configured to permit airflow through the first layer;
   an air chamber positioned under the first layer and covered by the mattress cover;
   a heating unit between the top surface of the first layer and the mattress cover, the heating unit being electrically controlled to increase a temperature at a foot portion of the bed system;
   a pad positioned on top of the air chamber and configured to permit airflow therethrough; and
   an air controller configured to move air through the pad to thereby control a temperature at a portion of the top surface of the first layer that corresponds to the pad.

2. The bed system of claim 1, further comprising:
   a power source configured to supply electrical power to the heating unit; and
   a controller configured to:
   selectively power the heating unit to generate heat;
   monitor a sleeping routine of a user over multiple days via one or more sensors to determine a learned sleep schedule; and
   drive the heating unit to heat the foot portion of the bed system as a function of the learned sleep schedule.

3. The bed system of claim 1, further comprising:
   a power source configured to supply electrical power to the heating unit; and
   a controller configured to:
   selectively power the heating unit to generate heat;
   determine whether a user is asleep as a function of sensed data; and
   drive the heating unit as a function of whether the user is determined to be asleep.

4. The bed system of claim 3, wherein the sensed data comprises at least one of sleep tracking data and user entering and leaving the bed data.

5. The bed system of claim 1, further comprising:
   a power source configured to supply electrical power to the heating unit; and
   a controller configured to:
   selectively power the heating unit to generate heat,
   determine an expected bed time for a user of the bed, and
   drive the heating unit to heat the foot portion of the bed system to reach a target temperature prior to the expected bed time.

6. The bed system of claim 5, further comprising:
   a sensor configured to detect the user laying on the bed system, wherein the sensor is in communication with the controller and wherein the controller is further configured to reduce power to the heating unit upon the sensor detecting the user laying on the mattress.

7. A bed system comprising:
   a mattress cover;
   a first layer having a top surface and an opposite bottom surface, the top surface covered by the mattress cover, the first layer configured to permit airflow through the first layer;
   a heating unit between the top surface of the first layer and the mattress cover, the heating unit being electrically controlled to increase a temperature at a foot portion of the bed system;
   a pad positioned and configured to permit airflow therethrough; and
   an air controller configured to move air through the pad to thereby control a temperature at a portion of the top surface of the first layer that corresponds to the pad, wherein the heating unit is positioned only at the foot portion of the bed system such that no heating units are positioned at a middle portion of the bed system and no heating units are positioned at a head portion of the bed system.

8. The bed system of claim 7, wherein the heating unit is configured to increase the temperature at the foot portion of the bed system while the pad is configured to decrease a temperature at a portion of the bed system that corresponds to the pad.

9. The bed system of claim 7, wherein the air controller is configured to draw ambient air from the pad to decrease a temperature at a portion of the bed system that corresponds to the pad, while the heating unit is configured to increase the temperature at the foot portion of the bed system.

10. The bed system of claim 7, wherein the air controller is configured to supply ambient air to the pad to decrease a temperature at a portion of the bed system that corresponds to the pad, while the heating unit is configured to increase the temperature at the foot portion of the bed system.

11. The bed system of claim 10, wherein the air controller is configured to heat or cool the ambient air.

12. A bed comprising:
a mattress comprising:
  a mattress cover;
  a support structure that is positioned under and covered by the mattress cover, wherein the support structure of the mattress comprises a first air chamber sized for supporting a first user, a second air chamber sized for supporting a second user, and a foam layer positioned above the first and second air chambers; and
  a foot warming system, wherein the foot warming system comprises:
    a first heating unit positioned at a foot portion of the mattress between the support structure and the mattress cover, the first heating unit connected to the foam layer above the first air chamber;
    a second heating unit positioned at the foot portion of the mattress between the support structure and the mattress cover, the second heating unit connected to the foam layer above the second air chamber;
    a power source; and
    electrical connectors electrically connecting the first heating unit and the second heating unit to the power source,
    wherein at least one of the first heating unit or the second heating unit is attached to the foam layer via an envelope having an envelope opening, wherein the at least one of the first heating unit or the second heating unit is removable through the envelope opening.

13. The bed of claim 12, further comprising:
a pad disposed on top of at least one of the first air chamber or the second air chamber and configured to permit airflow therethrough; and
an air controller configured to move air through the pad to control a temperature at a portion of the support structure that corresponds to the pad.

14. The bed of claim 12, wherein the at least one of the first heating unit or the second heating unit comprises a flexible layer of electrically conductive fabric.

15. The bed of claim 14, wherein the flexible layer of electrically conductive fabric allows the at least one of the first heating unit or the second heating unit to be compressed within the envelope, wherein the at least one of the first heating unit or the second heating unit is positioned inside the envelope between an envelope top and an envelope bottom, and wherein the at least one of the first heating unit or the second heating unit and the envelope are positioned at the foot portion of the mattress under the mattress cover.

16. The bed of claim 15, wherein the at least one of the first heating unit or the second heating unit is configured to lay flat within the envelope.

17. The bed of claim 12, wherein the at least one of the first heating unit or the second heating unit comprises a plurality of fabric heating elements spaced apart at specified gaps.

18. The bed of claim 17, wherein the specified gaps are between 0.2 and 0.7 inches.

19. The bed of claim 12, wherein the support structure defines a pathway through which the electrical connectors extend between the at least one of the first heating unit or the second heating unit and the power source.

20. A bed comprising:
a mattress comprising:
  a mattress cover;
  a support structure that is positioned under and covered by the mattress cover;
  a foam layer positioned above the support structure and below the mattress cover; and
  a foot warming system, wherein the foot warming system comprises:
    a first heating unit positioned at a foot portion of the mattress between the support structure and the mattress cover, the first heating unit connected to and above the foam layer;
    a second heating unit positioned at the foot portion of the mattress between the support structure and the mattress cover, the second heating unit connected to and above the foam layer; and
    an envelope attached to the foam layer, the envelope having an envelope opening, wherein the at least one of the first heating unit or the second heating unit is contained within and removable through the envelope opening.

21. A bed system comprising:
a mattress cover;
a first layer having a top surface and an opposite bottom surface, the top surface covered by the mattress cover, the first layer configured to permit airflow through the first layer;
a heating unit between the top surface of the first layer and the mattress cover, the heating unit being electrically controlled to increase a temperature at a foot portion of the bed system;
a pad positioned and configured to permit airflow therethrough;
an air controller configured to move air through the pad to thereby control a temperature at a portion of the top surface of the first layer that corresponds to the pad, wherein the heating unit is positioned only at the foot portion of the bed system; and
an envelope having an envelope opening, wherein the heating unit is attached to the first layer via the envelope, wherein the heating unit is removable through the envelope opening.

* * * * *